(12) United States Patent
Greve et al.

(10) Patent No.: US 10,851,116 B2
(45) Date of Patent: Dec. 1, 2020

(54) BICYCLIC AMINES AS NOVEL JAK KINASE INHIBITORS

(71) Applicant: LEO Pharma A/S, Ballerup (DK)

(72) Inventors: Daniel Rodriguez Greve, Ballerup (DK); Tue Heesgaard Jepsen, Ballerup (DK); Mogens Larsen, Ballerup (DK); Andreas Ritzen, Ballerup (DK)

(73) Assignee: LEO Pharma A/S, Ballerup (DK)

( * ) Notice: Subject to any disclaimer, the term of this patent is extended or adjusted under 35 U.S.C. 154(b) by 0 days.

(21) Appl. No.: 16/479,375

(22) PCT Filed: Jan. 19, 2018

(86) PCT No.: PCT/EP2018/051305
§ 371 (c)(1),
(2) Date: Jul. 19, 2019

(87) PCT Pub. No.: WO2018/134352
PCT Pub. Date: Jul. 26, 2018

(65) Prior Publication Data
US 2019/0382418 A1  Dec. 19, 2019

(30) Foreign Application Priority Data
Jan. 20, 2017 (EP) .................................... 17152447

(51) Int. Cl.
*C07D 519/00* (2006.01)
*A61K 31/519* (2006.01)

(52) U.S. Cl.
CPC .......... *C07D 519/00* (2013.01); *A61K 31/519* (2013.01)

(58) Field of Classification Search
CPC .......................... A61K 31/519; C07D 487/04
USPC ........................................ 514/265.1; 544/280
See application file for complete search history.

(56) References Cited

FOREIGN PATENT DOCUMENTS

| CN | 105732636 A | 7/2016 |
|---|---|---|
| EP | 2 460 806 A1 | 6/2012 |
| WO | WO 2012/054364 A2 | 4/2012 |
| WO | WO 2015//083028 A1 | 6/2015 |

OTHER PUBLICATIONS

Database Registry, Chemical Abstracts Service, XP002780198 (2016).
O'Shea, John J. et al., "Cytokine Signaling in 2002: New Surprises in the Jak/Stat Pathway," Cell., vol. 109, pp. S121-S131 (2002).
O'Shea, J.J., "Targeting the Jak/STAT pathway for immunosuppression," Ann. Rheum. Dis., vol. 63 (Suppl. 2:ii67), (2004).
O'Shea, John J., M.D., "JAKs and STATs in Immunity, Immunodeficiency, and Cancer," The New England Journal of Medicine, vol. 368, No. 2, pp. 161-170 (2013).
Schindler, Christian W., "Series Introduction: JAK-STAT signaling in human disease," J. Clin. Invest., vol. 109, No. 9, pp. 1133-1137 (2002).
Schindler, Christian et al., "JAK-STAT Signaling: From Interferons to Cytokines," Journal of Biological Chemistry, vol. 282, No. 28, pp. 20059-20063 (2007).
Schwartz, Daniella M. et al., "Type I/II cytokines, JAKs, and new strategies for treating autoimmune diseases," Nat. Rev. Rheumatol., vol. 12, No. 1, pp. 25-36 (2016).
International Search Report for International Application No. PCT/EP2018/051305, dated May 2, 2018. (3 pages).
Written Opinion of the International Searching Authority for International Application No. PCT/EP2018/051305. (5 pages).

*Primary Examiner* — Jeffrey H Murray
(74) *Attorney, Agent, or Firm* — Finnegan, Henderson, Farabow, Garrett & Dunner, LLP

(57) ABSTRACT

The present invention relates to a compound according to formula I

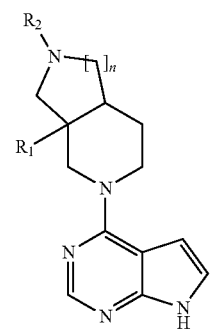

wherein $R_1$ is alkyl; n is 1 or 2; $R_2$ is selected from the group consisting of hydrogen, cyano, —$SO_2R_a$, —$SO_2NR_bR_c$, —$C(O)R_b$, phenyl and 5- and 6-membered heteroaryl or pharmaceutically acceptable salts, hydrates, or solvates thereof. The invention relates further to pharmaceutical compositions comprising said compounds, and to methods of treating proliferative or inflammatory skin disorders with said compounds.

20 Claims, 1 Drawing Sheet

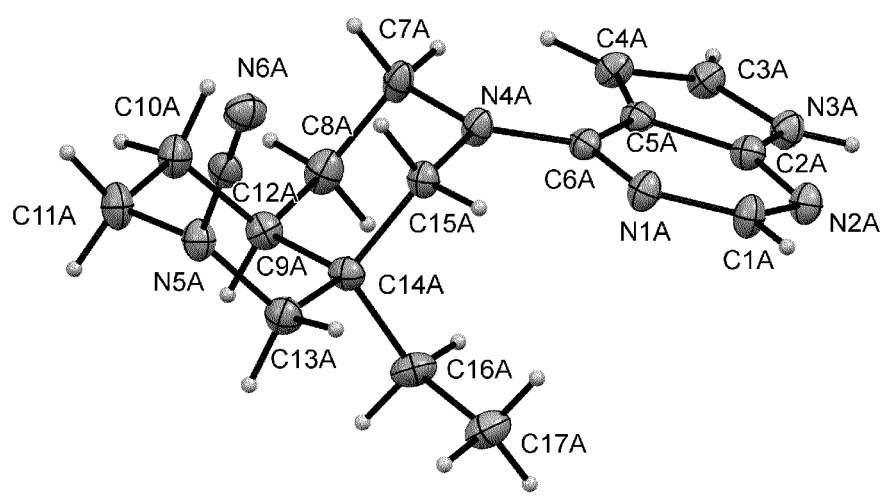

BICYCLIC AMINES AS NOVEL JAK KINASE INHIBITORS

This application is a national stage filing under 35 U.S.C. § 371 of International Application No. PCT/EP2018/051305, filed on Jan. 19, 2018, which claims priority of European Patent Application No. 17152447.3, filed on Jan. 20, 2017. The contents of these applications are each incorporated herein by reference.

FIELD OF THE INVENTION

This invention relates to compounds which are inhibitors of protein tyrosine kinases, such as the Janus kinases, to said compounds for use in therapy, to pharmaceutical compositions comprising said compounds and to methods of treating diseases with said compounds.

BACKGROUND OF THE INVENTION

This invention relates to novel compounds which are inhibitors of protein tyrosine kinases such as the Janus kinases, JAK1, JAK2, JAK3 and TYK2.

Protein tyrosine kinases are a family of enzymes catalyzing the transfer of the terminal phosphate of adenosine triphosphate to tyrosine residues in protein substrates. Phosphorylation of tyrosine residues on protein substrates leads to transduction of intracellular signals which regulate a wide variety of processes such as cell growth differentiation and activation, metabolism, hematopoiesis, host defense and immuno-regulation. As the elucidation of the molecular mechanisms in a number of inflammatory conditions and other disorders of the immune system (e.g. autoimmune diseases), highlighted the critical role of these intracellular signal pathways modulation of the activity of protein tyrosine kinases appears to be an attractive route to the management of inflammatory diseases. A large number of protein tyrosine kinases have been identified which may be receptor protein tyrosine kinases, e.g. the insulin receptor, or non-receptor protein tyrosine kinases.

The protein tyrosine kinases JAK1, JAK2, JAK3 and TYK2 selectively associate with the cytoplasmic domains of various cytokine receptor chains and have essential roles in cytokine-dependent regulation of tissue homeostasis, initiation of innate immunity, shaping adaptive immune responses and inflammatory processes. They are critical in signal transduction in response to their activation via tyrosine phosphorylation by stimulation of cytokine receptors. (1) Schindler C. et al. JAK-STAT signaling: from interferons to cytokines. J. Biol. Chem 2007; 282(28):20059; (2) O'Shea J. J. Targeting the Jak/STAT pathway for immunosuppression; Ann. Rheum. Dis. 2004; 63 Suppl 2:ii67; (3) Schindler C. Series introduction. JAK-STAT signaling in human disease; J. Clin. Invest. 2002; 109(9):1133); (4) O'Shea et. Al. Cell, Vol. 109, S121-S131, 2002; (5) Schwartz D. M. et al. Nat. Rev. Rheumatol., 2016; 12(1): 25-36; (6) O'Shea et al. New. Eng. J. Med. 2013; 368(2): 161-170.

While JAK1, JAK2 and TYK2 are ubiquitously expressed JAK3 is predominantly expressed in hematopoietic cells.

JAK1 plays a critical role in mediation of biological responses and JAK1 is widely expressed and associated with several major cytokine receptor families. It is involved in signaling by members of the IL-2 receptor γ subunit family (IL-2, IL-4, IL-7R, IL-9R, IL-15R and IL-21R), the IL-4 receptor family (IL-4R, IL-13R), the gp130 receptor family and class II cytokine receptors comprising of IL-10 receptor family and both type I and type II IFN receptor family.

JAK2 is implicated in signaling by several single chain receptors (including Epo-R, GHR, PRL-R), the IL-3 receptor family, the gp130 receptor family, the IL-12 receptor family (IL-12 and IL-23) and some Class II receptor cytokine family. Thus, JAK2 plays a critical role in transducing signals for Epo, IL-3, GM-CSF, IL-5 and IFNγ. JAK2 knockout mice exhibit an embryonic lethal phenotype.

JAK3 is involved in signal transduction by receptors that employ the common gamma chain of the type I cytokine receptor family also known as IL-2 receptor family (e.g. IL-2, IL-4, IL-7, IL-9, IL-15 and IL-21). XSCID patient populations have been identified with reduced levels of JAK3 protein or with genetic defects to the common gamma chain, suggesting that immune suppression should result from blocking signaling through the JAK3 pathway. Animal studies have suggested that JAK3 not only plays a critical role in B and T lymphocyte maturation, but that JAK3 is constitutively required to maintain T cell function. Modulation of immune activity through this novel mechanism can prove useful in the treatment of T cell proliferative disorders such as immune system diseases, in particular autoimmune diseases.

TYK2 is implicated in type I interferons, IL-6, IL-10, IL-12 and IL-23 signaling. A human patient with a TYK2 deficiency has been described and this patient had a primary immunodeficiency disorder characterized as a hyper-IgE-like syndrome with many opportunistic infections by virus, bacteria and fungi. Because IL-23 has been found to play an important role in many chronic inflammatory conditions, a TYK2 inhibitor could conceivably be very effective in treating diseased influenced by IL-23.

Inhibitors of the Janus kinases are expected to show utility in the treatment of inflammatory and non-infectious autoimmune diseases wherein these kinases are involved. Recently the pan-JAK inhibitors Tofacitinib and Ruxolitinib have been launched for the treatment of rheumatoid arthritis and myelofibrosis, respectively.

Hence, JAK inhibitors may furthermore be useful in the treatment of diseases related to activity of Janus kinases, including, for example skin diseases like proliferative and inflammatory skin disorders, psoriasis, atopic dermatitis, scleroderma, rosacea, skin cancers, dermatis, dermatitis herpetiformis, dermatomyositis, vitiligo, alopecia areata, contact dermatitis, eczema, xerosis, urticaria and chronic idiophatic pruritus; respiratory diseases like asthma, chronic obstructive pulmonary disease, pulmonary fibrosis, cystic fibrosis, rhinitis, bronchiolitis, byssinosis, pneumoconiosis, bronchiectasis, hypersensitivity pneumonitis, lung cancers, mesothelioma and sarcoidosis; gastrointestinal diseases like inflammatory bowel disease, ulcerative colitis, Crohn's disease, retroperitoneal fibrosis, celiac disease and cancers; eye diseases like myasthenia gravis, Sjögren's syndrome, conjunctivitis, scleritis, uveitis, dry eye syndrome, keratitis, iritis; systemic indications like lupus, multiple sclerosis, rheumatoid arthritis, type I diabetes and complications from diabetes, cancers, ankylosing spondylitis and psoriatic arthritis; as well as other autoimmune diseases and indications where immunosuppression would be desirable for example in organ transplantation.

WO 2012/054364 discloses bicyclic amines as Janus Kinase Inhibitors.

EP 2460806 discloses nitrogen-containing spiro-ring compounds as JAK2 and JAK3 inhibitors.

WO 2015/083028 discloses pyrrolo[2,3-D]pyrimidinyl, pyrrolo[2,3-B]pyrazinyl and pyrrolo[2,3-D]pyridinyl acrylamides as Janus Kinase inhibitors.

SUMMARY OF THE INVENTION

It is an object of the present invention to provide novel compounds which exhibit a high inhibitory activity on one or more of the Janus kinase receptors JAK1, JAK2, JAK3 and TYK2.

Compounds of the present invention may have advantageous properties such as improved metabolic stability properties and metabolic elimination properties, dermal stability and delivery properties, systemic exposure characteristics after local delivery, all of which may make them especially suitable to be used as active pharmaceutical ingredients in topical drug formulations.

A particular advantage of some compounds of the present invention is that they display stability in keratinocytes, while displaying high clearance in human liver microsomes or human hepatocytes, thus indicating both stability of the compounds in skin and high systemic clearance of the compounds, thereby indicating reduced risk of adverse side effects upon topical administration while retaining efficacy in skin.

Compounds of the present invention may have favorable solubility properties.

Compounds of the present invention may furthermore have advantageous safety properties, such as highly selective JAK inhibitory activity compared to other kinases and/or advantageous cytotoxic, phototoxic and genotoxic properties.

Accordingly, the invention relates to compounds of general formula I:

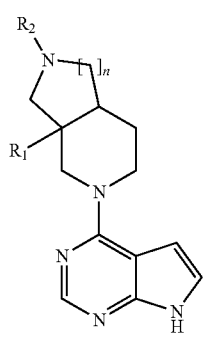

I wherein
$R_1$ represents methyl or ethyl;
n is 1 or 2;
$R_2$ is selected from the group consisting of hydrogen, cyano, —$SO_2R_a$, —$SO_2NR_bR_c$, —$C(O)R_b$, phenyl and
5- and 6-membered heteroaryl, wherein said phenyl, 5- and 6-membered heteroaryl are optionally substituted with one or more substituents independently selected from $R_3$,
$R_3$ represents the group consisting of hydroxyl, cyano, halogen, ($C_1$-$C_4$)alkyl, hydroxyl($C_1$-$C_4$)alkyl, halo($C_1$-$C_4$)alkyl, cyano($C_1$-$C_4$)alkyl, ($C_1$-$C_4$)alkoxy, halo($C_1$-$C_4$)alkoxy, —$SO_2R_a$ and —$SO_2NR_bR_c$;
$R_a$ is selected from ($C_1$-$C_4$)alkyl, ($C_3$-$C_6$)cycloalkyl, halo($C_1$-$C_4$)alkyl and cyano($C_1$-$C_4$)alkyl;
$R_b$ and $R_c$ are each independently selected from hydrogen, ($C_1$-$C_4$)alkyl, halo($C_1$-$C_4$)alkyl cyano($C_1$-$C_4$)alkyl, ($C_3$-$C_6$)cycloalkyl, halo($C_3$-$C_6$)cycloalkyl and cyano($C_3$-$C_6$)cycloalkyl;

or pharmaceutically acceptable salts, hydrates or solvates thereof.

In a further aspect the invention relates to a compound according to general formula I above for use as a medicament.

In another aspect the invention relates to a compound according to general formula I above for use in the prophylaxis and/or treatment of diseases of the immune system such as autoimmune diseases, or of diseases related to deregulation of the immune system.

In yet another aspect the invention relates to a pharmaceutical composition comprising a compound according to general formula I above together with a pharmaceutically acceptable vehicle or excipient or pharmaceutically acceptable carrier(s).

BRIEF DESCRIPTION OF THE DRAWINGS

FIG. 1 shows the ORTEP drawing of the absolute crystal structure of compound 22. The structure has two molecules in the asymmetric unit cell.

DETAILED DESCRIPTION OF THE INVENTION

Definitions

The term "($C_a$-$C_b$)alkyl" is intended to indicate a radical obtained when one hydrogen atom is removed from a branched or linear hydrocarbon. Said ($C_a$-$C_b$)alkyl comprises 1-6, preferably 1-4, such as 1-3, such as 2-3 or such as 1-2 carbon atoms. The term includes the subclasses normal alkyl (n-alkyl), secondary and tertiary alkyl, such as methyl, ethyl, n-propyl, isopropyl, n-butyl, isobutyl, sec.-butyl, tert.-butyl, n-pentyl, isopentyl, neopentyl, n-hexyl and isohexyl. The number of carbon atoms in "($C_a$-$C_b$)alkyl" is indicated by the prefix "($C_a$-$C_b$)", wherein a is the minimum number and b is the maximum number of carbons in the hydrocarbon radical. Thus, for example ($C_1$-$C_4$)alkyl is intended to indicate an alkyl radical comprising from 1 to 4 carbon atoms.

The terms "($C_a$-$C_b$)alkyloxy" and "($C_a$-$C_b$)alkoxy" are intended to indicate a radical of the formula —OR', wherein R' is ($C_a$-$C_b$)alkyl as indicated herein, wherein the ($C_a$-$C_b$) alkyl group is appended to the parent molecular moiety through an oxygen atom, e.g. methoxy (—$OCH_3$), ethoxy (—$OCH_2CH_3$), n-propoxy, isopropoxy, butoxy, tert-butoxy, and the like.

The term "aryl" is intended to indicate a radical of aromatic carbocyclic rings comprising 6-13 carbon atoms, such as 6-9 carbon atoms, such as 6 carbon atoms, in particular 5- or 6-membered rings, e.g. phenyl.

The term "cyano" is intended to indicate a —CN group attached to the parent molecular moiety through the carbon atom.

The term "cyano($C_a$-$C_b$)alkyl" is intended to indicate a ($C_a$-$C_b$)alkyl group as defined herein substituted with one or more cyano atoms as defined herein, such as cyanomethyl or cyanoethyl.

The term "($C_a$-$C_b$)cycloalkyl" is intended to indicate a saturated cycloalkane hydrocarbon radical, comprising ($C_a$-$C_b$) carbon atoms, such as 3-7 carbon atoms, preferably 3-6 carbon atoms, such as 3-5 carbon atoms or such as 3-4 carbon atoms, e.g. cyclopropyl, cyclobutyl, cyclopentyl, cyclohexyl, or cycloheptyl.

The term "halo($C_a$-$C_b$)alkyl" is intended to indicate a ($C_a$-$C_b$)alkyl group as defined herein substituted with one or more halogen atoms as defined herein, e.g. fluoro or chloro, such as difluoromethyl or trifluoromethyl.

The terms "halo($C_a$-$C_b$)alkyloxy" and "halo($C_a$-$C_b$)alkoxy" are intended to indicate an halo($C_a$-$C_b$)alkyl group as defined herein which is appended to the parent molecular moiety through an oxygen atom, such as difluoromethoxy or trifluoromethoxy.

The term "halogen" is intended to indicate a substituent from the $7^{th}$ main group of the periodic table, such as fluoro, chloro and bromo.

The term "5-membered-heteroaryl" and "6-membered-heteroaryl" is intended to indicate radicals of monocyclic heteroaromatic rings comprising a 5- or 6-membered ring which contains from 1-5 carbon atoms and from 1-4 heteroatoms selected from oxygen, sulphur and nitrogen, such as 5 carbon atoms and 1 heteroatom, such as 4 carbon atoms and 2 heteroatoms, such as 4 carbon atoms and 1 heteroatom, such as 3 carbon atoms and 2 heteroatoms, such as 2 carbon atoms and 3 heteroatoms. The heteroaryl radical may be connected to the parent molecular moiety through a carbon atom or a nitrogen atom contained anywhere within the heteroaryl group. Representative examples of 5-membered and 6-membered heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, tetrazolyl, thiadiazolyl, thiazolyl, thienyl and triazolyl.

The number of carbon atoms in a hydrocarbon radical (e.g. alkyl, cycloalkyl, and aryl) is indicated by the prefix "($C_a$-$C_b$)", wherein a is the minimum number and b is the maximum number of carbons in the hydrocarbon radical. Thus, for example ($C_1$-$C_4$)alkyl is intended to indicate an alkyl radical comprising from 1 to 4 carbon atoms, and ($C_3$-$C_5$)cycloalkyl is intended to indicate a cycloalkyl radical comprising from 3 to 5 carbon ring atoms.

The term "hydroxy" or "hydroxyl" is intended to indicate an OH radical.

The term "hydroxy($C_a$-$C_b$)alkyl" or "hydroxyl($C_a$-$C_b$)alkyl" is intended to indicate a ($C_a$-$C_b$)alkyl group as defined above substituted with one or more hydroxy, e.g. hydroxymethyl, hydroxyethyl, hydroxypropyl.

The term "oxo" is intended to indicate an oxygen atom which is connected to the parent molecular moiety via a double bond (=O).

The group C(O) is intended to represent a carbonyl group (C=O).

The group S(O) is intended to represent a sulfoxide group (S=O).

The group $S(O)_2$ or $SO_2$ is intended to represent a sulfone group (O=S=O).

If substituents are described as being independently selected from a group, each substituent is selected independent of the other. Each substituent may therefore be identical of different from the other substituent(s).

The term "optionally substituted" means "unsubstituted or substituted", and therefore the general formulas described herein encompasses compounds containing the specified optional substituent(s) as well as compounds that do not contain the optional substituent(s).

The term "pharmaceutically acceptable salt" is intended to indicate salts prepared by reacting a compound of formula I, which comprise a basic moiety, with a suitable inorganic or organic acid, such as hydrochloric, hydrobromic, hydroiodic, sulfuric, nitric, phosphoric, formic, acetic, 2,2-dichloroaetic, adipic, ascorbic, L-aspartic, L-glutamic, galactaric, lactic, maleic, L-malic, phthalic, citric, propionic, benzoic, glutaric, gluconic, D-glucuronic, methanesulfonic, salicylic, succinic, malonic, tartaric, benzenesulfonic, ethane-1,2-disulfonic, 2-hydroxy ethanesulfonic acid, toluenesulfonic, sulfamic or fumaric acid. Pharmaceutically acceptable salts of compounds of formula I comprising an acidic moiety may also be prepared by reaction with a suitable base such as sodium hydroxide, potassium hydroxide, magnesium hydroxide, calcium hydroxide, silver hydroxide, ammonia or the like, or suitable non-toxic amines, such as lower alkylamines, hydroxy-lower alkylamines, cycloalkylamines, or benzylamines, or L-arginine or L-lysine. Further examples of pharmaceutical acceptable salts are listed in Berge, S. M.; J. Pharm. Sci.; (1977), 66(1), 1-19, which is incorporated herein by reference.

The term "solvate" is intended to indicate a species formed by interaction between a compound, e.g. a compound of formula I, and a solvent, e.g. alcohol, glycerol or water, wherein said species are in a crystalline form. When water is the solvent, said species is referred to as a hydrate.

The term "treatment" as used herein means the management and care of a patient for the purpose of combating a disease, disorder or condition. The term is intended to include the delaying of the progression of the disease, disorder or condition, the amelioration, alleviation or relief of symptoms and complications, and/or the cure or elimination of the disease, disorder or condition. The term also includes prevention of the condition, wherein prevention is to be understood as the management and care of a patient for the purpose of combating the disease, condition or disorder and includes the administration of the active compounds to prevent the onset of the symptoms or complications. Nonetheless, prophylactic (preventive) and therapeutic (curative) treatments are two separate aspects.

All references, including publications, patent applications and patents, cited herein are hereby incorporated by reference in their entirety and to the same extent as if each reference were individually and specifically indicated to be incorporated by reference, regardless of any separately provided incorporation of particular documents made elsewhere herein.

EMBODIMENTS OF THE INVENTION

In an embodiment the invention provides a compound according to general formula I(a)

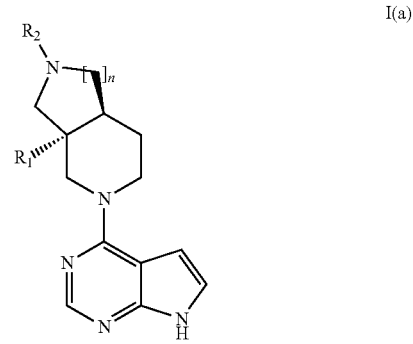

I(a)

Wherein n, $R_1$ and $R_2$ are as described above for general formula I

In an embodiment the invention provides a compound according to general formula I or I(a) wherein n is 2.

In an embodiment the invention provides a compound according to general formula I or I(a) wherein $R_1$ represents methyl and n is 2.

In an embodiment the invention provides a compound according to general formula I or I(a) wherein $R_1$ represents ethyl and n is 2.

In an embodiment the invention provides a compound according to general formula I or I(a) wherein $R_2$ is selected from the group consisting of hydrogen, cyano, —$SO_2R_a$, —$SO_2NR_bR_c$, —$C(O)R_b$, phenyl, pyridyl, pyrimidinyl, pyrazinyl, pyridazinyl, thiazolyl and thiadiazolyl, wherein said phenyl, pyridyl, pyrimidinyl, pyrazinyl, pyridazinyl, thiazolyl and thiadiazolyl are optionally substituted with one or more substituents independently selected from $R_3$.

In an embodiment the invention provides a compound according to general formula I or I(a) wherein $R_2$ is selected from the group consisting of hydrogen, cyano, —$SO_2R_a$ and —$SO_2NR_bR_c$.

In an embodiment the invention provides a compound according to general formula I or I(a) wherein $R_2$ is selected from the group consisting of cyano and —$SO_2NH_2$.

In an embodiment the invention provides a compound according to general formula I or I(a) wherein $R_3$ represents the group consisting of cyano, halogen, methyl, hydroxymethyl and —$SO_2CH_3$.

In an embodiment the invention provides a compound according to general formula I or I(a) wherein $R_a$ is selected from methyl and trifluoroethyl.

In an embodiment the invention provides a compound according to general formula I or I(a) wherein $R_b$ and $R_c$ each independently are selected from hydrogen, methyl and cyanomethyl.

In an embodiment the invention provides a compound according to general formula I or selected from
(4aR,8aS)-8a-methyl-7-(7H-pyrrolo[2,3-d]pyrimidin-4-yl)-3,4,4a,5,6,8-hexahydro-1H-2,7-naphthyridine-2-carbonitrile,
(4aR*,8aS*)-8a-methyl-7-(7H-pyrrolo[2,3-d]pyrimidin-4-yl)-3,4,4a,5,6,8-hexahydro-1H-2,7-naphthyridine-2-carbonitrile,
(4aS,8aR)-8a-methyl-7-(7H-pyrrolo[2,3-d]pyrimidin-4-yl)-3,4,4a,5,6,8-hexahydro-1H-2,7-naphthyridine-2-carbonitrile,
5-[(4aR*,8aS*)-8a-methyl-7-(7H-pyrrolo[2,3-d]pyrimidin-4-yl)-3,4,4a,5,6,8-hexahydro-1H-2,7-naphthyridin-2-yl]pyrazine-2-carbonitrile,
6-[(4aR*,8aS*)-8a-methyl-7-(7H-pyrrolo[2,3-d]pyrimidin-4-yl)-3,4,4a,5,6,8-hexahydro-1H-2,7-naphthyridin-2-yl]pyridine-3-carbonitrile,
6-[(4aR*,8aS*)-8a-methyl-7-(7H-pyrrolo[2,3-d]pyrimidin-4-yl)-3,4,4a,5,6,8-hexahydro-1H-2,7-naphthyridin-2-yl]pyridazine-3-carbonitrile,
2-[(4aR*,8aS*)-8a-methyl-7-(7H-pyrrolo[2,3-d]pyrimidin-4-yl)-3,4,4a,5,6,8-hexahydro-1H-2,7-naphthyridin-2-yl]pyrimidine-5-carbonitrile,
6-[(4aS*,8aR*)-8a-methyl-7-(7H-pyrrolo[2,3-d]pyrimidin-4-yl)-3,4,4a,5,6,8-hexahydro-1H-2,7-naphthyridin-2-yl]-4-methyl-pyridine-3-carbonitrile,
(4aR*,8aS*)-8a-methyl-7-(7H-pyrrolo[2,3-d]pyrimidin-4-yl)-3,4,4a,5,6,8-hexahydro-1H-2,7-naphthyridine-2-sulfonamide,
6-[(4aS*,8aR*)-8a-methyl-7-(7H-pyrrolo[2,3-d]pyrimidin-4-yl)-3,4,4a,5,6,8-hexahydro-1H-2,7-naphthyridin-2-yl]-2-methyl-pyridine-3-carbonitrile,
6-[(4aS*,8aR*)-8a-methyl-7-(7H-pyrrolo[2,3-d]pyrimidin-4-yl)-3,4,4a,5,6,8-hexahydro-1H-2,7-naphthyridin-2-yl]-5-methyl-pyridine-3-carbonitrile,
(4aS*,8aR*)-2-(5-bromo-4-methyl-2-pyridyl)-8a-methyl-7-(7H-pyrrolo[2,3-d]pyrimidin-4-yl)-3,4,4a,5,6,8-hexahydro-1H-2,7-naphthyridine,
(4aR*,8aS*)-8a-methyl-2-methylsulfonyl-7-(7H-pyrrolo[2,3-d]pyrimidin-4-yl)-3,4,4a,5,6,8-hexahydro-1H-2,7-naphthyridine,
(4aS*,8aR*)-2-(5-bromo-6-methyl-2-pyridyl)-8a-methyl-7-(7H-pyrrolo[2,3-d]pyrimidin-4-yl)-3,4,4a,5,6,8-hexahydro-1H-2,7-naphthyridine,
1-[(4aR*,8aS*)-8a-ethyl-7-(7H-pyrrolo[2,3-d]pyrimidin-4-yl)-3,4,4a,5,6,8-hexahydro-1H-2,7-naphthyridin-2-yl]ethanone,
(4aR*,8aS*)-8a-ethyl-7-(7H-pyrrolo[2,3-d]pyrimidin-4-yl)-3,4,4a,5,6,8-hexahydro-1H-2,7-naphthyridine-2-carbaldehyde,
(4aR*,8aS*)-8a-ethyl-7-(7H-pyrrolo[2,3-d]pyrimidin-4-yl)-3,4,4a,5,6,8-hexahydro-1H-2,7-naphthyridine-2-sulfonamide,
(4aR,8aS)-8a-ethyl-7-(7H-pyrrolo[2,3-d]pyrimidin-4-yl)-3,4,4a,5,6,8-hexahydro-1H-2,7-naphthyridine-2-sulfonamide,
(4aS,8aR)-8a-ethyl-7-(7H-pyrrolo[2,3-d]pyrimidin-4-yl)-3,4,4a,5,6,8-hexahydro-1H-2,7-naphthyridine-2-sulfonamide,
2-[(4aR*,8aS*)-8a-ethyl-7-(7H-pyrrolo[2,3-d]pyrimidin-4-yl)-3,4,4a,5,6,8-hexahydro-1H-2,7-naphthyridin-2-yl]-5-bromo-1,3,4-thiadiazole,
(4aS,8aR)-8a-ethyl-7-(7H-pyrrolo[2,3-d]pyrimidin-4-yl)-3,4,4a,5,6,8-hexahydro-1H-2,7-naphthyridine-2-carbonitrile,
(4aR,8aS)-8a-ethyl-7-(7H-pyrrolo[2,3-d]pyrimidin-4-yl)-3,4,4a,5,6,8-hexahydro-1H-2,7-naphthyridine-2-carbonitrile,
(4aR*,8aS*)-8a-ethyl-7-(7H-pyrrolo[2,3-d]pyrimidin-4-yl)-3,4,4a,5,6,8-hexahydro-1H-2,7-naphthyridine-2-carbonitrile,
8a-ethyl-7-(7H-pyrrolo[2,3-d]pyrimidin-4-yl)-1,2,3,4,4a,5,6,8-octahydro-2,7-naphthyridine,
2-[(4aR*,8aS*)-8a-ethyl-7-(7H-pyrrolo[2,3-d]pyrimidin-4-yl)-3,4,4a,5,6,8-hexahydro-1H-2,7-naphthyridin-2-yl]thiazole-4-carbonitrile,
4-[(3aS*,7aS*)-3a-methyl-2-methylsulfonyl-1,3,4,6,7,7a-hexahydropyrrolo[3,4-c]pyridin-5-yl]-7H-pyrrolo[2,3-d]pyrimidine,
(3aS*,7aS*)-3a-methyl-5-(7H-pyrrolo[2,3-d]pyrimidin-4-yl)-1,3,4,6,7,7a-hexahydropyrrolo[3,4-c]pyridine-2-sulfonamide,
(3aR,7aR)-3a-methyl-5-(7H-pyrrolo[2,3-d]pyrimidin-4-yl)-1,3,4,6,7,7a-hexahydropyrrolo[3,4-c]pyridine-2-carbonitrile,
(3aS,7aS)-3a-methyl-5-(7H-pyrrolo[2,3-d]pyrimidin-4-yl)-1,3,4,6,7,7a-hexahydropyrrolo[3,4-c]pyridine-2-carbonitrile,
(3aS*,7aS*)—N-(cyanomethyl)-3a-methyl-5-(7H-pyrrolo[2,3-d]pyrimidin-4-yl)-1,3,4,6,7,7a-hexahydropyrrolo[3,4-c]pyridine-2-sulfonamide,
4-[(3aS*,7aS*)-3a-methyl-2-(2,2,2-trifluoroethylsulfonyl)-1,3,4,6,7,7a-hexahydropyrrolo[3,4-c]pyridin-5-yl]-7H-pyrrolo[2,3-d]pyrimidine,
3-[(3aS*,7aS*)-3a-methyl-5-(7H-pyrrolo[2,3-d]pyrimidin-4-yl)-1,3,4,6,7,7a-hexahydropyrrolo[3,4-c]pyridin-2-yl]-3-oxo-propanenitrile,
6-[(3aS,7aS)-3a-methyl-5-(7H-pyrrolo[2,3-d]pyrimidin-4-yl)-1,3,4,6,7,7a-hexahydropyrrolo[3,4-c]pyridin-2-yl]pyridine-3-carbonitrile,
6-[(3aR,7aR)-3a-methyl-5-(7H-pyrrolo[2,3-d]pyrimidin-4-yl)-1,3,4,6,7,7a-hexahydropyrrolo[3,4-c]pyridin-2-yl]pyridine-3-carbonitrile, 4-[(3aS*,7aS*)-3a-methyl-2-(5-methylsulfonyl-2-pyridyl)-1,3,4,6,7,7a-hexahydropyrrolo[3,4-c]pyridin-5-yl]-7H-pyrrolo[2,3-d]pyrimidine,

[2-[(3aS*,7aS*)-3a-methyl-5-(7H-pyrrolo[2,3-d]pyrimidin-4-yl)-1,3,4,6,7,7a-hexahydropyrrolo[3,4-c]pyridin-2-yl]-3-pyridyl]methanol,

[2-[(3aS*,7aS*)-3a-methyl-5-(7H-pyrrolo[2,3-d]pyrimidin-4-yl)-1,3,4,6,7,7a-hexahydropyrrolo[3,4-c]pyridin-2-yl]-5-bromo-3-pyridyl]methanol, 4-[(3aR*,7aS*)-3a-methyl-2-(4-methylsulfonylphenyl)-1,3,4,6,7,7a-hexahydropyrrolo[3,4-c]pyridin-5-yl]-7H-pyrrolo[2,3-d]pyrimidine, 4-[(3aR*,7aS*)-3a-methyl-2-pyrimidin-4-yl-1,3,4,6,7,7a-hexahydropyrrolo[3,4-c]pyridin-5-yl]-7H-pyrrolo[2,3-d]pyrimidine, 6-[(3aR*,7aS*)-3a-methyl-5-(7H-pyrrolo[2,3-d]pyrimidin-4-yl)-1,3,4,6,7,7a-hexahydropyrrolo[3,4-c]pyridin-2-yl]-4-methyl-pyridine-3-carbonitrile, 2-[(3aS*,7aS*)-3a-methyl-5-(7H-pyrrolo[2,3-d]pyrimidin-4-yl)-1,3,4,6,7,7a-hexahydropyrrolo[3,4-c]pyridin-2-yl]pyrimidine-5-carbonitrile, 6-[(3aS*,7aS*)-3a-methyl-5-(7H-pyrrolo[2,3-d]pyrimidin-4-yl)-1,3,4,6,7,7a-hexahydropyrrolo[3,4-c]pyridin-2-yl]pyridazine-3-carbonitrile, 5-[(3aS*,7aS*)-3a-methyl-5-(7H-pyrrolo[2,3-d]pyrimidin-4-yl)-1,3,4,6,7,7a-hexahydropyrrolo[3,4-c]pyridin-2-yl]pyrazine-2-carbonitrile, 6-[(3aS*,7aS*)-3a-methyl-5-(7H-pyrrolo[2,3-d]pyrimidin-4-yl)-1,3,4,6,7,7a-hexahydropyrrolo[3,4-c]pyridin-2-yl]-5-methyl-pyridine-3-carbonitrile, 6-[(3aR*,7aS*)-3a-methyl-5-(7H-pyrrolo[2,3-d]pyrimidin-4-yl)-1,3,4,6,7,7a-hexahydropyrrolo[3,4-c]pyridin-2-yl]-2-methyl-pyridine-3-carbonitrile, 1-[(3aS*,7aS*)-3a-methyl-5-(7H-pyrrolo[2,3-d]pyrimidin-4-yl)-1,3,4,6,7,7a-hexahydropyrrolo[3,4-c]pyridine-2-carbonyl]cyclopentanecarbonitrile, 6-[(3aS*,7aS*)-3a-methyl-5-(7H-pyrrolo[2,3-d]pyrimidin-4-yl)-1,3,4,6,7,7a-hexahydropyrrolo[3,4-c]pyridin-2-yl]pyridine-3-carbonitrile or pharmaceutically acceptable salts, hydrates or solvates thereof.

In an embodiment the invention provides a compound according to general formula I selected from (4aR*,8aS*)-8a-ethyl-7-(7H-pyrrolo[2,3-d]pyrimidin-4-yl)-3,4,4a,5,6,8-hexahydro-1H-2,7-naphthyridine-2-sulfonamide or pharmaceutically acceptable salts, hydrates or solvates thereof.

In an embodiment the invention provides a compound according to general formula I selected from (4aR*,8aS*)-8a-ethyl-7-(7H-pyrrolo[2,3-d]pyrimidin-4-yl)-3,4,4a,5,6,8-hexahydro-1H-2,7-naphthyridine-2-carbonitrile or pharmaceutically acceptable salts, hydrates or solvates thereof.

In an embodiment the invention provides a compound according to general formula I selected from (4aR,8aS)-8a-ethyl-7-(7H-pyrrolo[2,3-d]pyrimidin-4-yl)-3,4,4a,5,6,8-hexahydro-1H-2,7-naphthyridine-2-sulfonamide or pharmaceutically acceptable salts, hydrates or solvates thereof.

In an embodiment the invention provides a compound according to general formula I selected from (4aS,8aR)-8a-ethyl-7-(7H-pyrrolo[2,3-d]pyrimidin-4-yl)-3,4,4a,5,6,8-hexahydro-1H-2,7-naphthyridine-2-sulfonamide or pharmaceutically acceptable salts, hydrates or solvates thereof.

In an embodiment the invention provides a compound according to general formula I selected from (4aS,8aR)-8a-ethyl-7-(7H-pyrrolo[2,3-d]pyrimidin-4-yl)-3,4,4a,5,6,8-hexahydro-1H-2,7-naphthyridine-2-carbonitrile or pharmaceutically acceptable salts, hydrates or solvates thereof.

In an embodiment the invention provides a compound according to general formula I selected from (4aR,8aS)-8a-ethyl-7-(7H-pyrrolo[2,3-d]pyrimidin-4-yl)-3,4,4a,5,6,8-hexahydro-1H-2,7-naphthyridine-2-carbonitrile or pharmaceutically acceptable salts, hydrates or solvates thereof.

In an embodiment the invention provides a compound according to general formula I wherein said compound is (4aR,8aS)-8a-ethyl-7-(7H-pyrrolo[2,3-d]pyrimidin-4-yl)-3,4,4a,5,6,8-hexahydro-1H-2,7-naphthyridine-2-sulfonamide.

In an embodiment the invention provides a compound according to general formula I wherein said compound is (4aR,8aS)-8a-ethyl-7-(7H-pyrrolo[2,3-d]pyrimidin-4-yl)-3,4,4a,5,6,8-hexahydro-1H-2,7-naphthyridine-2-carbonitrile.

In an embodiment the invention provides a compound according to general formula I selected from (4aR,8aS)-8a-ethyl-7-(7H-pyrrolo[2,3-d]pyrimidin-4-yl)-3,4,4a,5,6,8-hexahydro-1H-2,7-naphthyridine-2-sulfonamide or pharmaceutically acceptable salts thereof.

In an embodiment the invention provides a compound according to general formula I selected from (4aR,8aS)-8a-ethyl-7-(7H-pyrrolo[2,3-d]pyrimidin-4-yl)-3,4,4a,5,6,8-hexahydro-1H-2,7-naphthyridine-2-carbonitrile or pharmaceutically acceptable salts thereof.

In an embodiment the invention provides a compound according to general formula I selected from (4aR,8aS)-8a-ethyl-7-(7H-pyrrolo[2,3-d]pyrimidin-4-yl)-3,4,4a,5,6,8-hexahydro-1H-2,7-naphthyridine-2-sulfonamide or hydrates thereof.

In an embodiment the invention provides a compound according to general formula I selected from (4aR,8aS)-8a-ethyl-7-(7H-pyrrolo[2,3-d]pyrimidin-4-yl)-3,4,4a,5,6,8-hexahydro-1H-2,7-naphthyridine-2-carbonitrile or hydrates thereof.

In an embodiment the invention provides a compound according to general formula I selected from (4aR,8aS)-8a-ethyl-7-(7H-pyrrolo[2,3-d]pyrimidin-4-yl)-3,4,4a,5,6,8-hexahydro-1H-2,7-naphthyridine-2-sulfonamide or solvates thereof.

In an embodiment the invention provides a compound according to general formula I selected from (4aR,8aS)-8a-ethyl-7-(7H-pyrrolo[2,3-d]pyrimidin-4-yl)-3,4,4a,5,6,8-hexahydro-1H-2,7-naphthyridine-2-carbonitrile or solvates thereof.

In an embodiment the invention provides a compound according to general formula I wherein said compound is (4aR*,8aS*)-8a-ethyl-7-(7H-pyrrolo[2,3-d]pyrimidin-4-yl)-3,4,4a,5,6,8-hexahydro-1H-2,7-naphthyridine-2-sulfonamide.

In an embodiment the invention provides a compound according to general formula I wherein said compound is (4aR*,8aS*)-8a-ethyl-7-(7H-pyrrolo[2,3-d]pyrimidin-4-yl)-3,4,4a,5,6,8-hexahydro-1H-2,7-naphthyridine-2-carbonitrile.

In an embodiment the invention provides a compound according to general formula I selected from (4aR*,8aS*)-8a-ethyl-7-(7H-pyrrolo[2,3-d]pyrimidin-4-yl)-3,4,4a,5,6,8-hexahydro-1H-2,7-naphthyridine-2-sulfonamide or pharmaceutically acceptable salts thereof.

In an embodiment the invention provides a compound according to general formula I selected from (4aR*,8aS*)-8a-ethyl-7-(7H-pyrrolo[2,3-d]pyrimidin-4-yl)-3,4,4a,5,6,8-hexahydro-1H-2,7-naphthyridine-2-carbonitrile or pharmaceutically acceptable salts thereof.

In an embodiment the invention provides a compound according to general formula I selected from (4aR*,8aS*)-

8a-ethyl-7-(7H-pyrrolo[2,3-d]pyrimidin-4-yl)-3,4,4a,5,6,8-hexahydro-1H-2,7-naphthyridine-2-sulfonamide or hydrates thereof.

In an embodiment the invention provides a compound according to general formula I selected from (4aR*,8aS*)-8a-ethyl-7-(7H-pyrrolo[2,3-d]pyrimidin-4-yl)-3,4,4a,5,6,8-hexahydro-1H-2,7-naphthyridine-2-carbonitrile or hydrates thereof.

In an embodiment the invention provides a compound according to general formula I selected from (4aR*,8aS*)-8a-ethyl-7-(7H-pyrrolo[2,3-d]pyrimidin-4-yl)-3,4,4a,5,6,8-hexahydro-1H-2,7-naphthyridine-2-sulfonamide or solvates thereof.

In an embodiment the invention provides a compound according to general formula I selected from (4aR*,8aS*)-8a-ethyl-7-(7H-pyrrolo[2,3-d]pyrimidin-4-yl)-3,4,4a,5,6,8-hexahydro-1H-2,7-naphthyridine-2-carbonitrile or solvates thereof.

In an embodiment the invention provides a compound according to general formula I selected from (4aR,8aS)-8a-methyl-7-(7H-pyrrolo[2,3-d]pyrimidin-4-yl)-3,4,4a,5,6,8-hexahydro-1H-2,7-naphthyridine-2-carbonitrile or pharmaceutically acceptable salts, hydrates or solvates thereof.

In an embodiment the invention provides a compound according to general formula I selected from (4aR*,8aS*)-8a-methyl-7-(7H-pyrrolo[2,3-d]pyrimidin-4-yl)-3,4,4a,5,6,8-hexahydro-1H-2,7-naphthyridine-2-carbonitrile or pharmaceutically acceptable salts, hydrates or solvates thereof.

In an embodiment the invention provides a compound according to general formula I selected from 5-[(4aR*,8aS*)-8a-methyl-7-(7H-pyrrolo[2,3-d]pyrimidin-4-yl)-3,4,4a,5,6,8-hexahydro-1H-2,7-naphthyridin-2-yl]pyrazine-2-carbonitrile or pharmaceutically acceptable salts, hydrates or solvates thereof.

In an embodiment the invention provides a compound according to general formula I selected from 6-[(3aS,7aS)-3a-methyl-5-(7H-pyrrolo[2,3-d]pyrimidin-4-yl)-1,3,4,6,7,7a-hexahydropyrrolo[3,4-c]pyridin-2-yl]pyridine-3-carbonitrile or pharmaceutically acceptable salts, hydrates or solvates thereof.

In an embodiment the invention provides a compound according to general formula I selected from 4-[(3aS*,7aS*)-3a-methyl-2-(5-methylsulfonyl-2-pyridyl)-1,3,4,6,7,7a-hexahydropyrrolo[3,4-c]pyridin-5-yl]-7H-pyrrolo[2,3-d]pyrimidine or pharmaceutically acceptable salts, hydrates or solvates thereof.

In an embodiment the invention provides a compound according to general formula I selected from [2-[(3aS*,7aS*)-3a-methyl-5-(7H-pyrrolo[2,3-d]pyrimidin-4-yl)-1,3,4,6,7,7a-hexahydropyrrolo[3,4-c]pyridin-2-yl]-5-bromo-3-pyridyl]methanol or pharmaceutically acceptable salts, hydrates or solvates thereof.

In an embodiment the invention provides a compound according to general formula I selected from 4-[(3aR*,7aS*)-3a-methyl-2-(4-methylsulfonylphenyl)-1,3,4,6,7,7a-hexahydropyrrolo[3,4-c]pyridin-5-yl]-7H-pyrrolo[2,3-d]pyrimidine or pharmaceutically acceptable salts, hydrates or solvates thereof.

In an embodiment the invention provides a compound according to general formula I selected from 6-[(3aR*,7aS*)-3a-methyl-5-(7H-pyrrolo[2,3-d]pyrimidin-4-yl)-1,3,4,6,7,7a-hexahydropyrrolo[3,4-c]pyridin-2-yl]-4-methyl-pyridine-3-carbonitrile or pharmaceutically acceptable salts, hydrates or solvates thereof.

In an embodiment the invention provides a compound according to general formula I selected from 5-[(3aS*,7aS*)-3a-methyl-5-(7H-pyrrolo[2,3-d]pyrimidin-4-yl)-1,3,4,6,7,7a-hexahydropyrrolo[3,4-c]pyridin-2-yl]pyrazine-2-carbonitrile or pharmaceutically acceptable salts, hydrates or solvates thereof.

In an embodiment the invention provides a compound according to general formula I selected from 6-[(3aS*,7aS*)-3a-methyl-5-(7H-pyrrolo[2,3-d]pyrimidin-4-yl)-1,3,4,6,7,7a-hexahydropyrrolo[3,4-c]pyridin-2-yl]pyridine-3-carbonitrile or pharmaceutically acceptable salts, hydrates or solvates thereof.

In one or more embodiments the invention provides compounds on general formula I(b), I(c) or I(d), wherein $R_1$, $R_2$ and n are as described above.

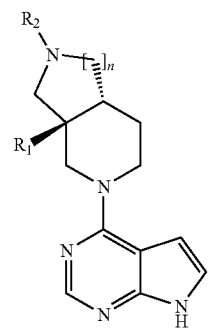

I(b)

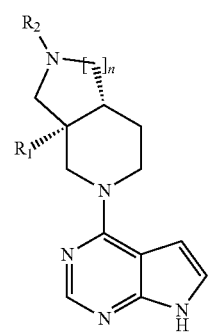

I(c)

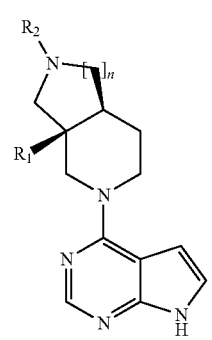

I(d)

In one or more embodiments the invention provides compounds on general formula I(e), I(c) or I(d), wherein $R_1$ and $R_2$ are as described above.

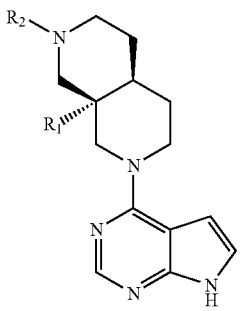

I(e)

Any combination of two or more embodiments described herein is considered within the scope of the present invention.

The present invention includes all embodiments wherein n, $R_1$, $R_2$, $R_3$, $R_a$, $R_b$ and $R_c$ are combined in any combination as anywhere described herein.

The compounds of formula I may be obtained in crystalline form either directly by concentration from an organic solvent or by crystallisation or recrystallisation from an organic solvent or mixture of said solvent and a cosolvent that may be organic or inorganic, such as water. The crystals may be isolated in essentially solvent-free form or as a solvate, such as a hydrate. The invention covers all crystalline forms, such as polymorphs and pseudopolymorphs, and also mixtures thereof.

Compounds of formula I comprise asymmetrically substituted (chiral) carbon atoms which give rise to the existence of isomeric forms, e.g. enantiomers and diastereomers. The present invention relates to all such isomers, either in optically pure form or as mixtures thereof (e.g. racemates and racemic mixtures or partially purified optical mixtures). Pure stereoisomeric forms of the compounds and the intermediates of this invention may be obtained by the application of procedures known in the art. The various isomeric forms may be separated by physical separation methods such as selective crystallization and chromatographic techniques, e.g. high pressure liquid chromatography using chiral stationary phases. Enantiomers may be separated from each other by selective crystallization of their diastereomeric salts which may be formed with optically active amines, or with optically active acids. Optically purified compounds may subsequently be liberated from said purified diastereomeric salts. Enantiomers may also be resolved by the formation of diastereomeric derivatives. Alternatively, enantiomers may be separated by chromatographic techniques using chiral stationary phases. Pure stereoisomeric forms may also be derived from the corresponding pure stereoisomeric forms of the appropriate starting materials, provided that the reaction occur stereoselectively or stereospecifically. Preferably, if a specific stereoisomer is desired, said compound will be synthesized by stereoselective or stereospecific methods of preparation. These methods will advantageously employ chiral pure starting materials. Furthermore, when a double bond or a fully or partially saturated ring system is present in the molecule geometric isomers may be formed. It is intended that any geometric isomer, as separated, pure or partially purified geometric isomers or mixtures thereof are included within the scope of the invention. The relative stereochemistry of a racemic mixture is indicated by a * in the naming of the relevant compounds of the present invention. Thus for example "(4aR*,8aS*)-8a-ethyl-7-(7H-pyrrolo[2,3-d]pyrimidin-4-yl)-3,4,4a,5,6,8-hexahydro-1H-2,7-naphthyridine-2-sulfonamide" indicates a racemic mixture of "(4aR,8aS)-8a-ethyl-7-(7H-pyrrolo[2,3-d]pyrimidin-4-yl)-3,4,4a,5,6,8-hexahydro-1H-2,7-naphthyridine-2-sulfonamide" and "(4aS,8aR)-8a-ethyl-7-(7H-pyrrolo[2,3-d]pyrimidin-4-yl)-3,4,4a,5,6,8-hexahydro-1H-2,7-naphthyridine-2-sulfonamide".

In the compounds of general Formula I, the atoms may exhibit their natural isotopic abundances, or one or more of the atoms may be artificially enriched in a particular isotope having the same atomic number, but an atomic mass or mass number different from the atomic mass or mass number found in nature. The present invention is meant to include all suitable isotopic variations of the compounds of general Formula I. For example, different isotopic forms of hydrogen include $^1$H, $^2$H and $^3$H and different isotopic forms of carbon include $^{12}$C, $^{13}$C and $^{14}$C and different isotopic forms of nitrogen include $^{14}$N and $^{15}$N. Enriching for deuterium ($^2$H) may for example increase in-vivo half-life or reduce dosage regiments, or may provide a compound useful as a standard for characterization of biological samples. Isotopically enriched compounds within general formula I can be prepared by conventional techniques well known to a person skilled in the art or by processes analogous to those described in the General Methods and Examples herein using appropriate isotopically enriched reagents and/or intermediates.

In one or more embodiments of the present invention, the compounds of formula I as defined above are useful in therapy and in particular useful for treatment of for example skin diseases like proliferative and inflammatory skin disorders, psoriasis, atopic dermatitis, scleroderma, rosacea, skin cancers, dermatis, dermatitis herpetiformis, dermatomyositis, vitiligo, alopecia areata, contact dermatitis, eczema, xerosis, ichthyosis, urticaria and chronic idiopathic pruritus; respiratory diseases like asthma, chronic obstructive pulmonary disease, pulmonary fibrosis, cystic fibrosis, rhinitis, bronchiolitis, byssinosis, pneumoconiosis, bronchiectasis, hypersensitivity pneumonitis, lung cancers, mesothelioma and sarcoidosis; gastrointestinal diseases like inflammatory bowel disease, ulcerative colitis, Crohn's disease, retroperitoneal fibrosis, celiac disease and cancers; eye diseases like myasthenia gravis, Sjögren's syndrome, conjunctivitis, scleritis, uveitis, dry eye syndrome, keratitis, iritis; systemic indications like lupus, multiple sclerosis, rheumatoid arthritis, type I diabetes and complications from diabetes, cancers, ankylosing spondylitis and psoriatic arthritis; as well as other autoimmune diseases and indications where immunosuppression would be desirable for example in organ transplantation.

In an embodiment the invention provides compounds of formula I as defined above for use in the prophylaxis and/or treatment of psoriasis or atopic dermatitis.

In an embodiment the invention provides a method of preventing, treating or ameliorating diseases of the immune system, such as autoimmune diseases, the method comprising administering to a person suffering from at least one of said diseases an effective amount of one or more compounds according to general formula I above optionally together with a pharmaceutically acceptable carrier or one or more excipients, optionally in combination with other therapeutically active compounds.

In an embodiment the invention provides a method of preventing, treating or ameliorating psoriasis or atopic dermatitis the method comprising administering to a person suffering from at least one of said diseases an effective amount of one or more compounds according to general formula I above optionally together with a pharmaceutically acceptable carrier or one or more excipients, optionally in combination with other therapeutically active compounds.

In an embodiment the invention provides a compound according to formula I for use in the manufacture of a medicament for the prophylaxis and/or treatment of diseases of the immune system, such as autoimmune disease, such as psoriasis or atopic dermatitis.

In one or more embodiments of the present invention, the compounds of formula I as defined above are useful as an anti-inflammatory agent capable of modulating the activity of a protein tyrosine kinase of the JAK family of protein tyrosine kinases, such as JAK1, JAK2, JAK3 or TYK2 protein tyrosine kinases.

Besides being useful for human treatment, the compounds of the present invention may also be useful for veterinary treatment of animals including mammals such as horses, cattle, sheep, pigs, dogs, and cats.

Pharmaceutical Compositions of the Invention

For use in therapy, compounds of the present invention are typically in the form of a pharmaceutical composition. The invention therefore relates to a pharmaceutical composition comprising a compound of formula I, optionally together with one or more other therapeutically active compound(s), together with pharmaceutically acceptable excipients, vehicles or carrier(s). The excipient must be "acceptable" in the sense of being compatible with the other ingredients of the composition and not deleterious to the recipient thereof.

Conveniently, the active ingredient comprises from 0.0001-99.9% by weight of the formulation.

In the form of a dosage unit, the compound may be administered one or more times a day at appropriate intervals, always depending, however, on the condition of the patient, and in accordance with the prescription made by the medical practitioner. Conveniently, a dosage unit of a formulation contain between 0.001 mg and 1000 mg, preferably between 0.1 mg and 300 mg, such as 50-200 mg of a compound of formula I. A suitable dosage of the compound of the invention will depend, inter alia, on the age and condition of the patient, the severity of the disease to be treated and other factors well known to the practicing physician. The compound may be administered either orally, parenterally, topically, transdermally or interdermally or other routes according to different dosing schedules, e.g. daily, weekly or with monthly intervals. In general a single dose will be in the range from 0.001 to 400 mg/kg body weight. The compound may be administered as a bolus (i.e. the entire daily dosis is administered at once) or in divided doses two or more times a day.

In the context of topical treatment it may be more appropriate to refer to a "usage unit", which denotes a single dose which is capable of being administered to a patient, and which may be readily handled and packed, remaining as a physically and chemically stable unit dose comprising either the active material as such or a mixture of it with solid, semisolid or liquid pharmaceutical diluents or carriers.

The term "usage unit" in connection with topical use means a unitary, i.e. a single dose, capable of being administered topically to a patient in an application per square centimetre of the treatment area of from 0.001 microgram to 1 mg and preferably from 0.05 microgram to 0.5 mg of the active ingredient in question.

It is also envisaged that in certain treatment regimes, administration with longer intervals, e.g. every other day, every week, or even with longer intervals may be beneficial.

If the treatment involves administration of another therapeutically active compound it is recommended to consult *Goodman & Gilman's The Pharmacological Basis of Therapeutics*, 9*th* Ed., J. G. Hardman and L. E. Limbird (Eds.), McGraw-Hill 1995, for useful dosages of said compounds.

The administration of a compound of the present invention with one or more other active compounds may be either concomitantly or sequentially.

The formulations include e.g. those in a form suitable for oral (including sustained or controlled release), rectal, parenteral (including subcutaneous, intraperitoneal, intramuscular, intraarticular and intravenous), transdermal, intradermal, ophthalmic, topical, nasal, sublingual or buccal administration.

The formulations may conveniently be presented in dosage unit form and may be prepared by but not restricted to any of the methods well known in the art of pharmacy, e.g. as disclosed in Remington, *The Science and Practice of Pharmacy*, 21ed ed., 2005. All methods include the step of bringing the active ingredient into association with the carrier, which constitutes one or more accessory ingredients. In general, the formulations are prepared by uniformly and intimately bringing the active ingredient into association with a liquid carrier, semisolid carrier or a finely divided solid carrier or combinations of these, and then, if necessary, shaping the product into the desired formulation.

Formulations of the present invention suitable for oral and buccal administration may be in the form of discrete units as capsules, sachets, tablets, chewing gum or lozenges, each containing a predetermined amount of the active ingredient; in the form of a powder, granules or pellets; in the form of a solution or a suspension in an aqueous liquid or non-aqueous liquid, such as ethanol or glycerol; or in the form of a gel, a nano- or microemulsion, an oil-in-water emulsion, a water-in-oil emulsion or other dispensing systems. The oils may be edible oils, such as but not restricted to e.g. cottonseed oil, sesame oil, coconut oil or peanut oil. Suitable dispersing or suspending agents for aqueous suspensions include synthetic or natural surfactants and viscosifying agents. The active ingredients may also be administered in the form of a bolus, electuary or paste.

A tablet may be made by compressing, moulding or freeze drying the active ingredient optionally with one or more accessory ingredients. Compressed tablets may be prepared by compressing, in a suitable machine, the active ingredient(s) in a free-flowing form such as a powder or granules, optionally mixed by a binder and/or filler; a lubricant; a disintegrating agent or a dispersing agent. Moulded tablets may be made by moulding, in a suitable machine, a mixture of the powdered active ingredient and suitable carrier moistened with an inert liquid diluent. Freeze dryed tablets may be formed in a freeze-dryer from a solution of the drug substance. A suitable filler can be included.

Formulations for rectal administration may be in the form of suppositories in which the compound of the present invention is admixed with low melting point, water soluble or insoluble solids, while elixirs may be prepared using myristyl palmitate.

Formulations suitable for parenteral administration conveniently comprise a sterile oily or aqueous preparation of the active ingredients, which is preferably isotonic with the blood of the recipient, e.g. isotonic saline, isotonic glucose solution or buffer solution. Furthermore, the formulation may contain cosolvent, solubilising agent and/or complexation agents. The formulation may be conveniently sterilised by for instance filtration through a bacteria retaining filter, addition of sterilizing agent to the formulation, irradiation of the formulation or heating of the formulation. Liposomal formulations as disclosed in e.g. Encyclopedia of Pharmaceutical Technology, vol. 9, 1994, are also suitable for parenteral administration.

Alternatively, the compounds of formula I may be presented as a sterile, solid preparation, e.g. a freeze-dried powder, which is readily dissolved in a sterile solvent immediately prior to use.

Transdermal formulations may be in the form of a plaster, patch, microneedles, liposomal or nanoparticulate delivery systems or other cutaneous formulations applied to the skin.

Formulations suitable for ophthalmic administration may be in the form of a sterile aqueous preparation of the active ingredients, which may be in microcrystalline form, for example, in the form of an aqueous microcrystalline suspension. Liposomal formulations or biodegradable polymer systems e.g. as disclosed in Encyclopedia of Pharmaceutical Technology, vol. 2, 1989, may also be used to present the active ingredient for ophthalmic administration.

Formulations suitable for topical, such as dermal, intradermal or ophthalmic administration include liquid or semisolid preparations such as liniments, lotions, gels, applicants, sprays, foams, film forming systems, microneedles, micro- or nano-emulsions, oil-in-water or water-in-oil emulsions such as creams, ointments or pastes; or solutions or suspensions such as drops.

For topical administration, the compound of formula I may typically be present in an amount of from 0.001 to 20% by weight of the composition, such as 0.01% to about 10%, such as 0.1-5% but may also be present in an amount of up to about 100% of the composition.

Formulations suitable for nasal or buccal administration include powder, self-propelling and spray formulations, such as aerosols and atomisers. Such formulations are disclosed in greater detail in e.g. Modern Pharmaceutics, $2^{nd}$ ed., G. S. Banker and C. T. Rhodes (Eds.), page 427-432, Marcel Dekker, New York; Modern Pharmaceutics, $3^{th}$ ed., G. S. Banker and C. T. Rhodes (Eds.), page 618-619 and 718-721, Marcel Dekker, New York and Encyclopedia of Pharmaceutical Technology, vol. 10, J. Swarbrick and J. C. Boylan (Eds), page 191-221, Marcel Dekker, New York.

In addition to the aforementioned ingredients, the formulations of a compound of formula I may include one or more additional ingredients such as diluents, buffers, flavouring agents, colourant, surface active agents, thickeners, penetration enhancing agents, solubility enhancing agents preservatives, e.g. methyl hydroxybenzoate (including anti-oxidants), emulsifying agents and the like.

When the active ingredient is administered in the form of salts with pharmaceutically acceptable non-toxic acids or bases, preferred salts are for instance easily water-soluble or slightly soluble in water, in order to obtain a particular and appropriate rate of absorption.

Methods of Preparation

The compounds of the present invention can be prepared in a number of ways well known to those skilled in the art of synthesis. The compounds of formula I in scheme 1 may for example be prepared using the reactions and techniques outlined below together with methods known in the art of synthetic organic chemistry, or variations thereof as appreciated by those skilled in the art. Preferred methods include, but are not limited to, those described below. The reactions are carried out in solvents appropriate to the reagents and materials employed and suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognized by one skilled in the art of organic synthesis. Not all compounds falling into a given class may be compatible with some of the reaction conditions required in some of the methods described. Such restrictions to the substituents which are compatible with the reaction conditions will be readily apparent to one skilled in the art and alternative methods can be used.

Starting materials are either known or commercially available compounds or can be prepared by routine synthetic methods well known to a person skilled in the art.

General Procedures, Preparations and Examples $^1$H nuclear magnetic resonance (NMR) spectra were recorded at 300 MHz, 400 MHz or 600 MHz. Chemical shift values ($\delta$, in ppm) are quoted in the specified solvent relative to internal tetramethylsilane ($\delta$=0.00) or chloroform ($\delta$=7.26). The value of a multiplet, either defined (doublet (d), double doublet (dd), triplet (t), quartet (q)) or not (m) at the approximate mid point is given unless a range is quoted. (br) indicates a broad peak. The organic solvents used were usually anhydrous.

Prep HPLC (Acidic)
Apparatus: Gilson HPLC system with Gilson UV/VIS-155 detector
Column: Waters SunFire™ Prep C18 5 µm OBD 19×250 mm
Reagents: (A) 0.1% formic acid-water solution; (B) MeCN
Pump:
  flow: 30 mL/min

| Time [min] | [%] B |
| --- | --- |
| 0.0 | 10 |
| 2.0 | 10 |
| 9.0 | 100 |
| 13.0 | 100 |

Prep HPLC (Basic)
Apparatus: Gilson HPLC system with Gilson UV/VIS-155 detector
Column: Waters XBridge® Prep C18 5 µm OBD 19×250 mm
Reagents: (A) 50 mM NH$_4$HCO$_3$ solution; (B) MeCN
Pump:
  flow: 30 mL/min

| Time [min] | [%] B |
| --- | --- |
| 0.0 | 0 |
| 2.0 | 0 |
| 9.0 | 60 |
| 10.0 | 100 |
| 13.0 | 100 |

Analytical UPLC-MS
Column: Waters Aquity UPLC HSS T3 1.8 µm, 2.1×50 mm.
Column temperature: 60° C.
UV: PDA 210-400 nm.
Injection volume: 2 µl.
Eluents:
A: 10 mM Ammonium acetate with 0.1% formic acid.
B: 100% Acetonitrile with 0.1% formic acid.

Gradient:

| Time (min) | A % | B % | Flow (mL/min) |
|---|---|---|---|
| 0.0 | 95 | 5 | 1.2 |
| 0.9 | 5 | 95 | 1.2 |
| 0.91 | 5 | 95 | 1.3 |
| 1.2 | 5 | 95 | 1.3 |
| 1.21 | 5 | 95 | 1.2 |
| 1.40 | 95 | 5 | 1.2 |

MS: Electrospray switching between positive and negative ionisation.
Instruments: Waters Aquity UPLC, Waters SQD
Analytical UPLC-MS Method 5
Column: Acquity UPLC HSS T3 1.8 µm; 2.1×50 mm
Flow: 0.7 mL/min
Column temp: 40° C.
Mobile phases:
A: 10 mM Ammonium acetate+0.1% formic acid
B: 100% Acetonitrile+0.1% formic acid
UV: 240-400 nm
Injection volume: 2 µl
Gradient:

| Time (min) | A % | B % |
|---|---|---|
| 0.0 | 99% | 1% |
| 0.5 | 94% | 6% |
| 1.0 | 94% | 6% |
| 2.6 | 5% | 95% |
| 3.8 | 5% | 95% |
| 3.81 | 99% | 1% |
| 4.8 | 99% | 1% |

UPLC (inlet method): XE Metode 7 CM
MS—method: PosNeg_50_1000
Instruments: Waters Acquity UPLC, Waters LCT Premier XE Column chromatography was performed either manually using silica gel (100-200 mesh) or automated using pre-packed columns on either a CombiFlash ISCO system or a Grace Reveleris system.

The solvent ratios indicated refer to v:v unless otherwise noted.

The Fieser method was used to work up reactions containing LAH, which consists of adding x mL water per x g LAH used, then add x mL 15% aq. NaOH and 3× mL water and filter off precipitated salts.

The following abbreviations have been used throughout:
Aq. aqueous
AcOH acetic acid
BOC tert-butoxycarbonyl
Bz benzyl
CBz carboxybenzyl
CbzCl benzylchloroformate
DBU 1,8-diazabicyclo[5.4.0]undec-7-ene
DCM dichloromethane
DIPEA diisopropylethylamine
DMAP N,N-dimethyl-4-aminopyridine
DMF N,N'-dimethylformamide
DMSO dimethyl sulfoxide
DSC Differential scanning calorimetry
EDCI 1-ethyl-3-(3-dimethylaminopropyl)carbodiimide
Et ethyl
EtOAc ethyl acetate
EtOH ethanol
h hour(s)
HATU 1-[bis(dimethylamino)methylene]-1H-1,2,3-triazolo[4,5-b]pyridinium 3-oxid hexafluorophosphate
LAN lithium aluminium hydride
LG leaving group
Me methyl
MeCN acetonitrile
MeON methanol
NMR nuclear magnetic resonance
Ms mesylate
PG protecting group
Ph phenyl
Pr n-propyl
rt room temperature
SEM 2-(trimethylsilyl)ethoxymethyl
SM starting material
$S_nAr$ nucleophilic aromatic substitution
TEA triethylamine
TFA trifluoroacetic acid
THF tetrahydrofuran
$t_R$ retention time in minutes
Ts tosylate
v volume General Procedure of Preparation The general formula of the compounds of the invention (I) is show in Scheme 1

Scheme 1

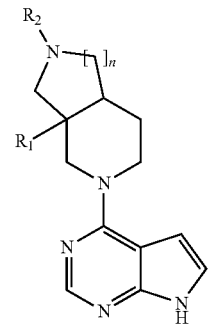

Wherein $R_1$, $R_2$ and n are defined as described herein.

Compounds of general formula I (where n=1) can for example be prepared by the general methods outlined in Scheme 2

Scheme 2

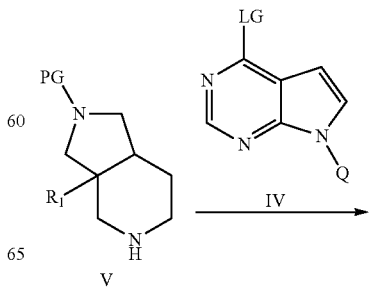

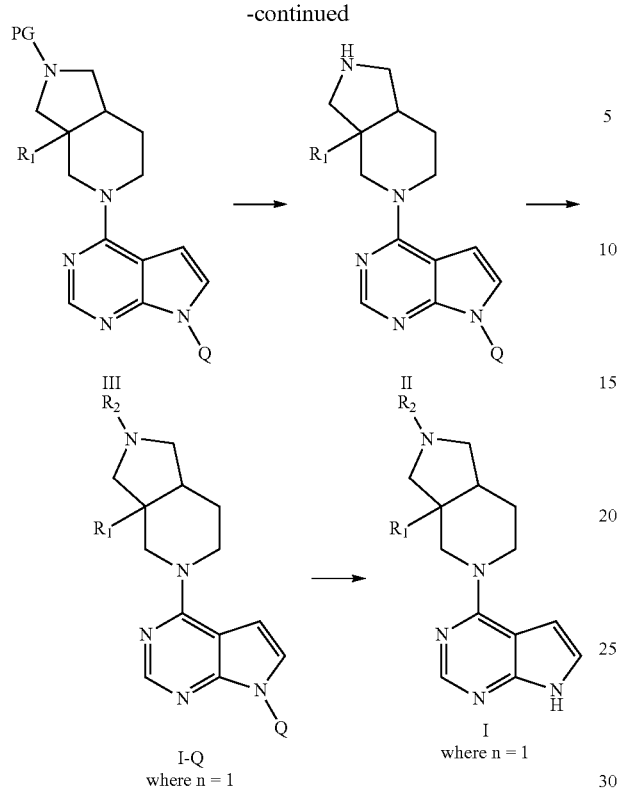

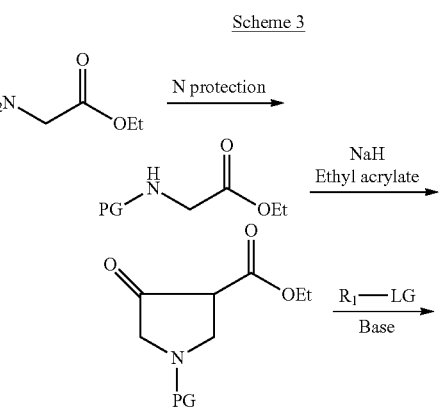

and Cu, suitable ligands includes P-based ligands like 2,2'-bis(diphenylphosphino)1,1'-binaphthyl and 4,5-bis-diphenylphosphanyl-9,9-dimethyl-9H-xanthene, and N-based ligands like N,N'-dimethylcyclohexane-1,2-diamine, suitable bases includes $Cs_2CO_3$, sodium tert-butoxide and $K_3PO_4$, and suitable solvents include dioxane and toluene.

Compounds of the general formula IV are either commercially available or are prepared from commercially available molecules by synthetic transformations according to standard procedures known to a chemist skilled in the art of organic synthesis. Compounds of general formula V are key building blocks in the synthesis of compounds of general formula I (where n=1), and they can for example be prepared as outlined in Scheme 3 and further described in details in the Intermediates section.

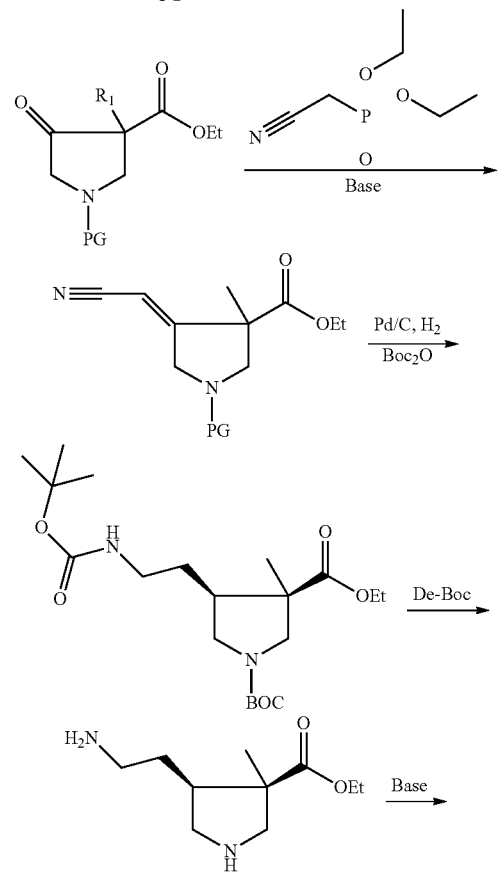

PG represents a suitable protecting group (see eg "Greene's Protective Groups in Organic Synthesis", 5$^{th}$ ed., Wuts P. G. M., John Wiley & Sons Inc.), such as, but not restricted to CBz, Bz, BOC, SEM and Ts.

LG represents a suitable leaving group, such as, but not restricted to: fluorine, chlorine, bromide, iodide, methoxy, —OMs or —OTs.

Q represents either —H or a protecting group as described for PG, depending on specific reaction needs.

Compounds of general formula I (where n=1) can be prepared by deprotecting compounds of general formula I-Q as needed. If Q is equal to —H no deprotection is needed.

Compounds of general formula I-Q can be prepared by reacting compounds of general formula II with suitably activated reagents or precursors of R$_2$, such as a sulphonic acid chloride (Example 31), activated haloheteroarenes (Example 38) and cyanogenbromide (Example 29).

Compounds of general formula II can be obtained from compounds of general formula III by deprotection of PG. In cases where Q is a protection group, this deprotection selectively removes PG while leaving Q in place, eg. as described under Intermediate 23.

Compounds of general formula III can be prepared by coupling of compounds of general formula V with pyrrolopyrimidine derivatives IV under SnAr conditions, for instance using a solvent like DMF, MeCN or water and a base like DIPEA or $K_2CO_3$ at a suitable temperature such as from room temperature to 200° C. by conventional heating or microwave induced heating Alternatively, the reaction between IV and V to form III can be performed in the presence of a transition metal based catalyst with a suitable ligand and a suitable base and in a suitable solvent, at a suitable temperature such as from room temperature to 200° C. by conventional heating or microwave induced heating. Typical transition metals includes Pd

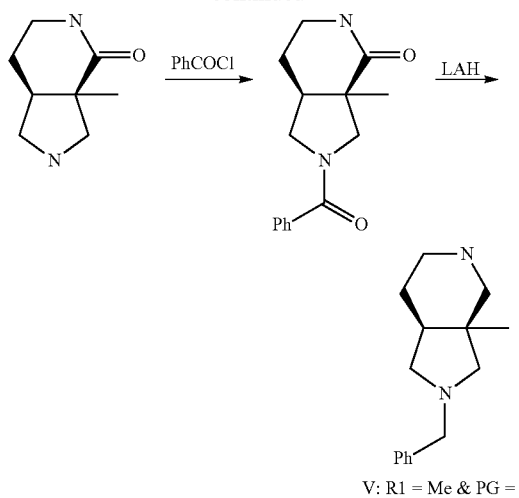

V: R1 = Me & PG = Bz

Compounds of general formula I (where n=2) can for example be prepared by the general methods outlined in Scheme 4

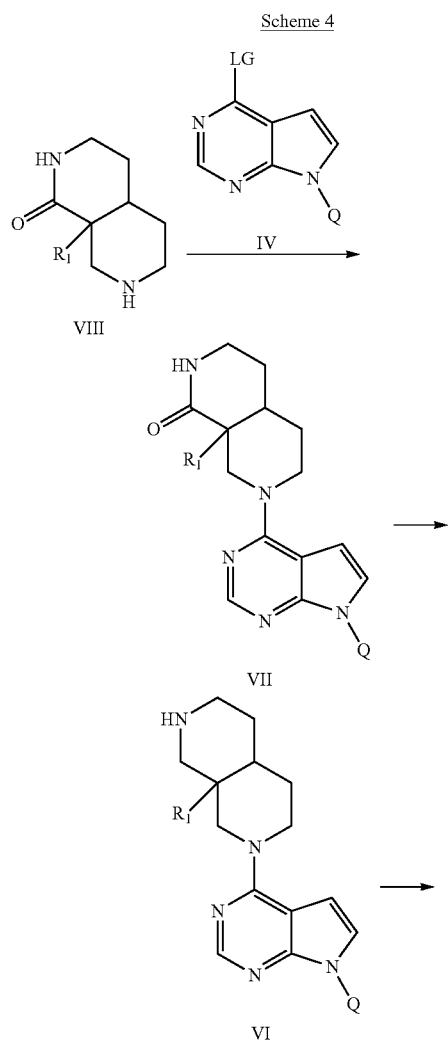

Scheme 4

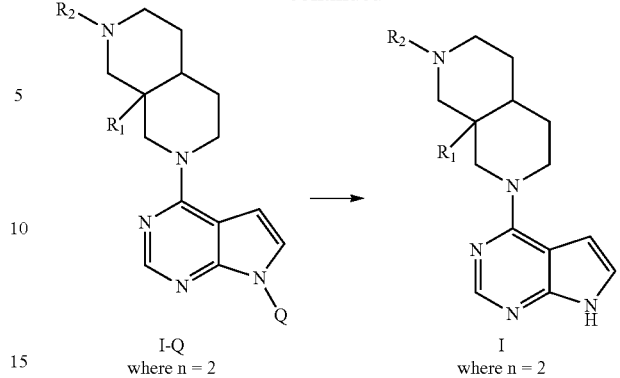

I-Q
where n = 2

I
where n = 2

Q represents either —H or a protecting group as described earlier for PG, depending on specific reaction needs.

LG represents a suitable leaving group, such as, but not restricted to: fluorine, chlorine, bromide, iodide, methoxy, —OMs or —OTs.

Compounds of general formula I (where n=2) can be prepared by deprotecting compounds of general formula I-Q (where n=2) as needed, such as in Examples 4-8. If Q is equal to —H no deprotection is needed, such as in Example 15 and Example 25.

Compounds of general formula I-Q (where n=2) can be prepared by reacting compounds of general formula VI with suitably activated reagents or precursors of $R_2$, such as activated haloheteroarenes (such as Examples 4-8) and methanesulfonyl chloride (Example 13).

Compounds of general formula VI can be obtained from compounds of general formula VII by reduction, eg. as described under Intermediate 6.

Compounds of general formula VII can be prepared by coupling of compounds of general formula VIII with pyrrolopyrimidine derivatives IV under SnAr conditions, for instance using a solvent like DMF, MeCN or water and a base like DIPEA or $K_2CO_3$ at a suitable temperature such as from room temperature to 200° C. by conventional heating or microwave induced heating Alternatively, the reaction between IV and VIII to form VII can be performed in the presence of a transition metal based catalyst with a suitable ligand and a suitable base and in a suitable solvent, at a suitable temperature such as from room temperature to 200° C. by conventional heating or microwave induced heating. Typical transition metals includes Pd and Cu, suitable ligands includes P-based ligands like 2,2'-bis(diphenylphosphino)1,1'-binaphthyl and 4,5-bis-diphenylphosphanyl-9,9-dimethyl-9H-xanthene, and N-based ligands like N,N'-dimethylcyclohexane-1,2-diamine, suitable bases includes $Cs_2CO_3$, sodium tert-butoxide and $K_3PO_4$, and suitable solvents include dioxane and toluene.

Compounds of the general formula IV are either commercially available or are prepared from commercially available molecules by synthetic transformations according to standard procedures known to a chemist skilled in the art of organic synthesis.

Compounds of general formula VIII are key building blocks in the synthesis of compounds of general formula I (where n=2), and they can for example be prepared as outlined in Scheme 5 and further described in details in the Intermediates section.

Scheme 5

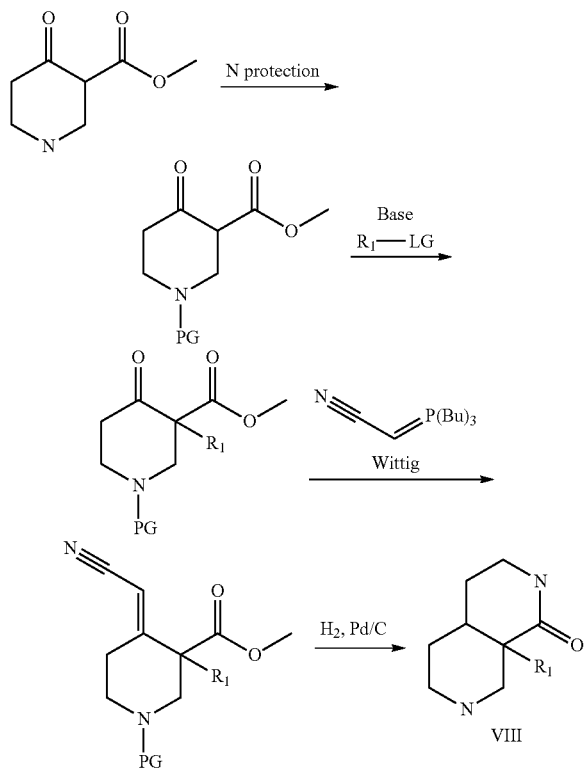

Alternatively, key building blocks of formula VIII and formula IX might be synthesised following the sequences outlined in Scheme 6.

Under Michael addition conditions alkene-diesters can be coupled with substituted malononitriles, and the product from that reaction can be further manipulated via hydrogenation, cyclisation and reduction to provide compounds of formula IX as outlined in scheme 6. Compounds of formula IX can be reacted with IV to give VI, under conditions similar to as described for reactions of VIII with IV.

Compounds of formula VII can, as outlined in scheme 6, be accessed starting from methyl 4-(cyanomethyl)pyridine-3-carboxylate, which via reduction of the nitrile, subsequent intramolecular cyclisation and reduction of the pyridine ring can give compounds of formula X. Further derivatization by enolate formation and alkylation can provide compounds of formula VIII, which can be used to prepare compounds of formula VII or further manipulated to IX.

Stereochemistry

In the synthetic procedures for Intermediates 2, 7 and 13 the described alkylations afford racemic products. Subsequent Intermediates and Examples using these intermediates are hence synthesized as racemic mixtures.

The indication of configuration using wedge and dash bonds in the structures of the intermediates and examples of the invention shall be taken to mean relative stereochemistry of racemic mixtures unless otherwise noted.

The relative stereochemistry of racemic mixtures is indicated by a * in the naming of the relevant compounds.

In the intramolecular cyclization procedures for Intermediates 4 and 9 the formation of both cis- and trans-bicyclic systems is possible, see scheme 7.

Scheme 6

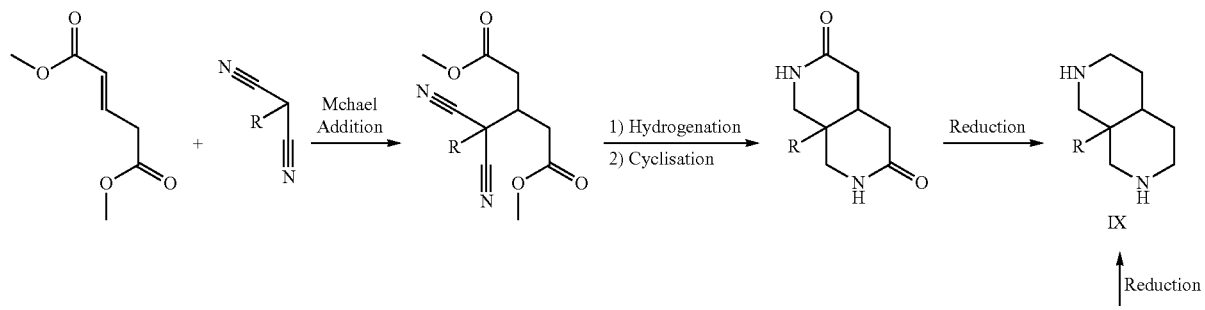

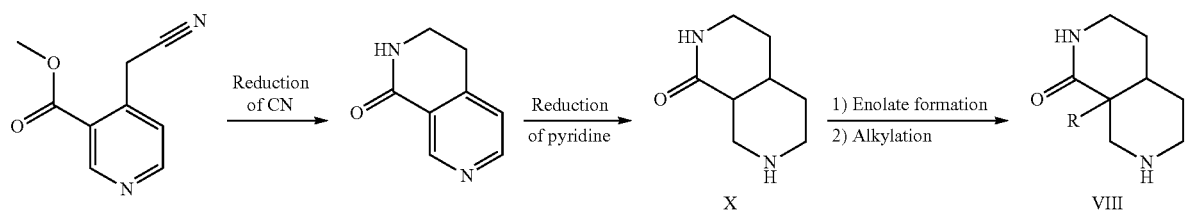

Scheme 7

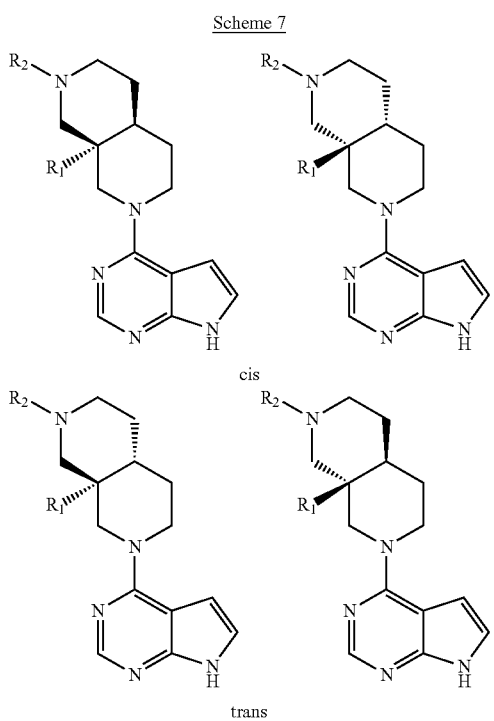

cis trans

Based on NOESY NMR studies on racemic Example 23 it was shown that this purified material consisted of the pure cis diastereomer, indicating that in the intramolecular cyclization step the formation of the cis diastereomer is dominating over trans, but the specific ratio of cis vs trans (i.e. the diastereomeric ratio) was not assessed.

For Intermediate 15 it has been described (Kim et al., Tetrahedron Letters 48 (2007) 5023-5026) that the hydrogenation step from Intermediate 14 to Intermediate 15 proceeds with a high degree of steric control resulting in a diastereomeric ratio of ~9:1. Separation of pure enantiomers was done by chiral chromatography for selected examples as described where performed.

INTERMEDIATES

Intermediate 1

O1-benzyl O3-methyl 4-oxopiperidine-1,3-dicarboxylate

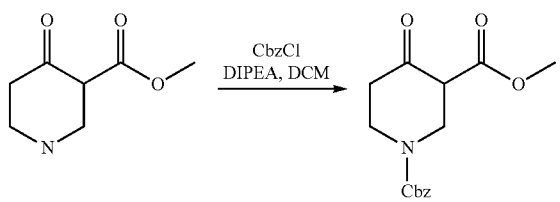 [SMILES: COC(=O)C1CNCCC1=O ; COC(=O)C1CN(C(=O)OCc2ccccc2)CCC1=O]

Methyl 4-oxopiperidine-3-carboxylate hydrochloride (25 g, 129.11 mmol) was suspended in DCM (250 mL) at 0° C. and DIPEA (38.4 g, 297 mmol, 50.8 mL) was added slowly to give a clear solution. CbzCl (24.2 g, 142 mmol, 20.3 mL) was then added dropwise to the solution and stirred at 0° C. for 30 min and then at rt for another 15 h for full conversion of the starting amine. The reaction mixture was washed with 10% aq. citric acid (2×100 mL), dried (MgSO$_4$), filtered and concentrated in vacuo to provide intermediate 1 (39.8 g, 123 mmol, 95% yield) as a crude yellow oil pure enough for further manipulation.

UPLC-MS: $t_R$=0.78 (M+H$^+$)=293.3

1H NMR (300 MHz, Chloroform-d) δ 11.97 (s, 1H), 7.46-7.27 (m, 5H), 5.16 (s, 2H), 4.14 (t, J=1.7 Hz, 2H), 3.78 (s, 3H), 3.65 (t, J=6.0 Hz, 2H), 2.39 (br s, 2H).

Intermediate 2

Racemic O1-benzyl O3-methyl 3-methyl-4-oxo-piperidine-1,3-dicarboxylate

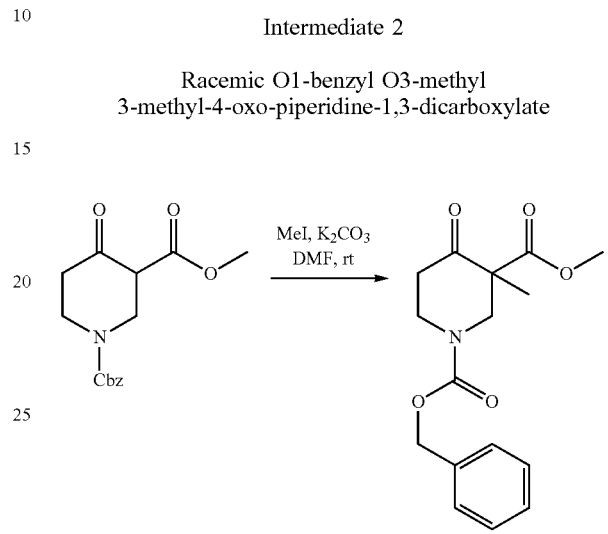

Intermediate 1 (15.0 g, 51.5 mmol), potassium carbonate (2.0 equiv., 102 mmol, 14.2 g) and iodomethane (3.0 equiv., 154 mmol, 21.9 g, 9.64 mL) were dissolved in DMF (50 mL) and stirred at rt for 3 h for full conversion of starting ketoester based on NMR. Aqeuos workup (brine/ether) followed by drying of the ether phase (magnesium sulfate), filtration and concentrated in vacuo afforded racemic Intermediate 2 (16.7 g, 50.8 mmol, 98% yield) pure enough for further manipulations.

UPLC-MS: $t_R$=0.73 (M+Na$^+$)=329.2

1H NMR (300 MHz, Chloroform-d) δ 7.36 (m, 5H), 5.17 (s, 2H), 4.60 (dd, J=13.7, 2.2 Hz, 1H), 4.24 (m, 1H), 3.64 (br s, 3H), 3.41 (m, 1H), 3.13 (d, J=13.7 Hz, 1H), 2.77 (ddd, J=15.1, 10.2, 6.5 Hz, 1H), 2.50 (dt, 3=15.5, 4.0 Hz, 1H), 1.31 (s, 3H).

Intermediate 3

Racemic O1-benzyl O3-methyl (4E)-4-(cyanomethylene)-3-methyl-piperidine-1,3-dicarboxylate

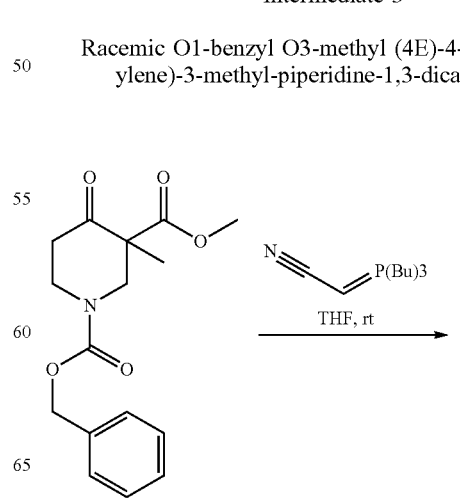

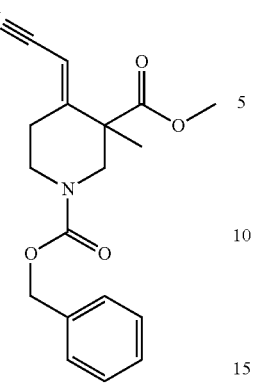

(Tributylphosphoranylidene)acetonitrile (1.05 equiv., 59.3 mmol, 14.3 g, 16 mL) was added with a syringe pump over 10 h (0.68 mL/h) to a solution of Intermediate 2 (17.2 g, 56.5 mmol) in dry THF (170 mL). The mixture was stirred at rt for 15 h for high conversion.

The reaction mixture was evaporated directly onto celite and purified by automated column chromatography (ISCO, gradient: Heptane->EtOAc) to afford Intermediate 3 as the pure E isomer (16.8 g, 51.2 mmol, 91% yield) as a colorless oil.

UPLC-MS: $t_R$=0.73 (M+H$^+$)=329.3

1H NMR (600 MHz, Chloroform-d) δ 7.47-7.30 (m, 5H), 5.16 (d, J=3.8 Hz, 2H), 4.52 (d, J=13.4 Hz, 1H), 4.34-4.04 (m, 1H), 3.64 (m, 3H), 3.18-2.86 (m, 2H), 2.83 (d, J=13.4 Hz, 1H), 2.58 (br s, 1H), 1.42-1.23 (br s, 3H).

Intermediate 4 (VIII, R1=Me)

8a-methyl-2,3,4,4a,5,6,7,8-octahydro-2,7-naphthyridin-1-one

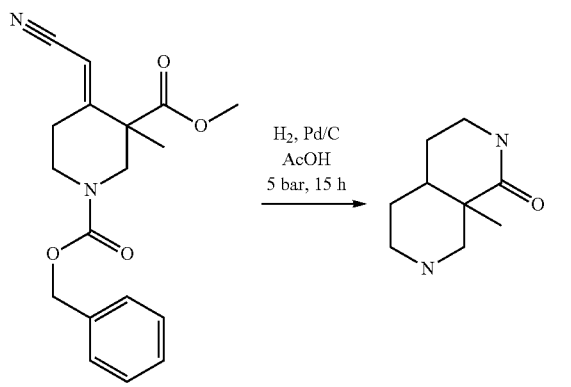 [SMILES: COC(=O)C1(C)CN(C(=O)OCc2ccccc2)CC/C1=C\C#N ; CC12CNCCC1CCNC2=O]

Pd on carbon (0.05 equiv., 2.54 mmol, 2.71 g, 10 mass %) was added to a solution of Intermediate 3 (16.7 g, 50.9 mmol) in AcOH (150 mL) and hydrogenated on Parr apparatus (4 bars) for 15 h for full conversion of SM.

The mixture was filtered through celite and concentrated in vacuo, and then coevaporated with toluene to remove trace of acetic acid. Intermediate 4 was moved on crude in the next reaction.

Intermediate 5 (VII, R1=Me)

8a-methyl-7-(7H-pyrrolo[2,3-d]pyrimidin-4-yl)-3,4,4a,5,6,8-hexahydro-2H-2,7-naphthyridin-1-one

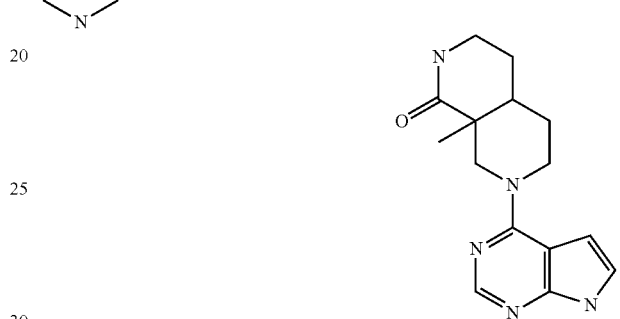

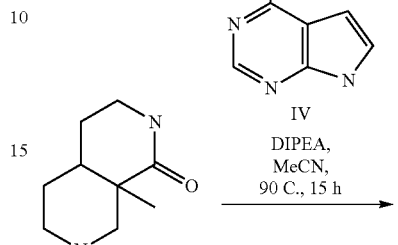

Intermediate 4 (8.50 g, 40.4 mmol), 4-chloropyrrolopyrimidine (1.0 equiv., 6.21 g, 40.4 mmol), and DIPEA (3.0 equiv., 15.7 g, 121 mmol, 21 mL) were dissolved in MeCN (120 mL) and refluxed (90° C.) for 15 h.

The crude reaction mixture was filtered through celite and concentrated in vacuo. The residue was loaded onto celite and purified by automated column chromatography (ISCO, DCM->10% MeOH in DCM) to afford Intermediate 5 (5.98 g, 21.0 mmol, 52% yield, 5.98 g) as a white foam.

UPLC-MS: $t_R$=0.34 (M+H$^+$)=286.1

1H NMR (300 MHz, Chloroform-d) δ 10.23 (br s, 1H), 8.26 (s, 1H), 7.05 (d, J=3.6 Hz, 1H), 6.97 (d, J=3.7 Hz, 1H), 5.95 (br s, 1H), 4.89 (d, J=13.5 Hz, 1H), 4.52 (d, J=13.2 Hz, 1H), 3.66 (m, 2H), 3.46-3.25 (m, 2H), 2.28-2.12 (m, 1H), 2.05-1.70 (m, 4H).

Intermediate 6 (Boc-VI, R1=Me)

tert-butyl 8a-methyl-7-(7H-pyrrolo[2,3-d]pyrimidin-4-yl)-3,4,4a,5,6,8-hexahydro-1H-2,7-naphthyridine-2-carboxylate

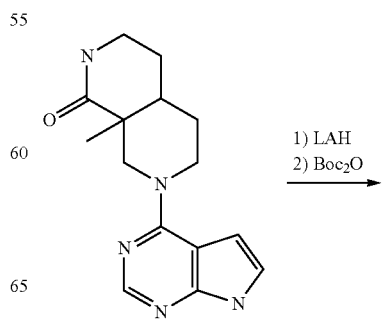

1) LAH
2) Boc$_2$O

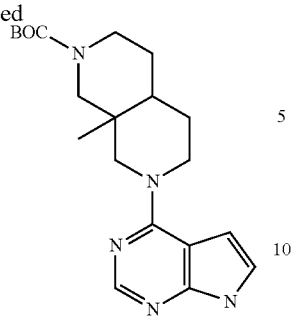

LAH (5.0 equiv., 105 mmol, 3.98 g) was added portionwise to a solution of Intermediate 5 (1.78 g, 5.95 mmol, 1.78 g) in dry THF (3 mL/mmol, 17.8 mL) and refluxed (80° C.) for 15 h for full conversion of lactam into the desired amine. The reaction mixture was cooled (0° C.) and quenched dropwise with ethyl acetate (40 mL) and MeOH (10 mL) until no further hydrogen gas evolved. Stirred at rt for another 1 h.

Then Boc-anhydride (2.0 equiv., 41.9 mmol, 9.15 g) was added and stirred at rt for 2 h for full conversion.

The mixture was filtered and the remains were washed several times with EtOAc, the filtrate was concentrated in vacuo, aq. workup (brine/EtOAc), dried (magnesium sulfate), filtered and evaporated to dryness. The crude worked up material consisted primarily of mono- and di-protected material and was purified by automated column chromatography (ISCO, gradient: Heptane->EtOAc) to afford Intermediate 6 (2.06 g, 5.55 mmol) as a white foam.

UPLC-MS: $t_R$=0.67 (M+H$^+$)=372.4

1H NMR (300 MHz, Chloroform-d) δ 10.64 (s, 1H), 8.32 (s, 1H), 7.07 (d, J=3.6 Hz, 1H), 6.52 (d, J=3.6 Hz, 1H), 4.11 (br s, 1H), 4.00 (d, J=13.6 Hz, 1H), 3.79 (m, 1H), 3.57-3.30 (m, 4H), 3.15 (d, J=14.0 Hz, 1H), 1.85-1.65 (m, 5H), 1.46 (s, 9H), 1.04 (s, 3H).

Intermediate 7

Racemic O1-benzyl O3-methyl 3-ethyl-4-oxo-piperidine-1,3-dicarboxylate

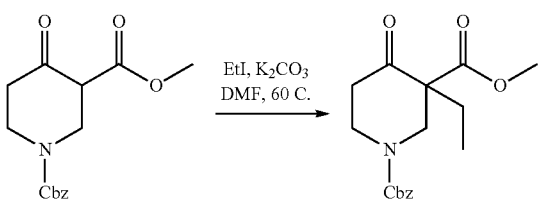 [SMILES: COC(=O)C1CN(C(=O)OCc2ccccc2)CCC1=O ; CCC1(C(=O)OC)CN(C(=O)OCc2ccccc2)CCC1=O]

Intermediate 1 (20 g, 68.7 mmol), potassium carbonate (2.0 equiv., 137 mmol, 18.9 g) and ethyl iodide (3.0 equiv., 206 mmol, 32.1 g, 16.6 mL) were dissolved in DMF (70 mL) and stirred at 50° C. for 2 h for full conversion of starting into desired product. Aq. workup (brine/ether), dried (magnesium sulfate), filtered and concentrated in vacuo to afford ethylation product Intermediate 7 (21.8 g, 68.3 mmol, 99% yield) pure enough for further manipulations. A small sample was purified by automated column chromatography (ISCO, gradient: Heptane->EtOAc) for identification.

UPLC-MS: $t_R$=0.74 (M+H$^+$)=320.3

1H NMR (rotamers, 300 MHz, Chloroform-d) δ 7.45-7.30 (m, 5H), 5.17 (d, J=6.5 Hz, 2H), 4.52-3.92 (m, 2H), 3.75-3.59 (m, 4H), 3.55-3.29 (m, 1H), 2.68-2.37 (m, 2H), 1.91-1.67 (m, 1H), 1.40-1.23 (m, 3H).

Intermediate 8

Racemic O1-benzyl O3-methyl (4E)-4-(cyanomethylene)-3-ethyl-piperidine-1,3-dicarboxylate

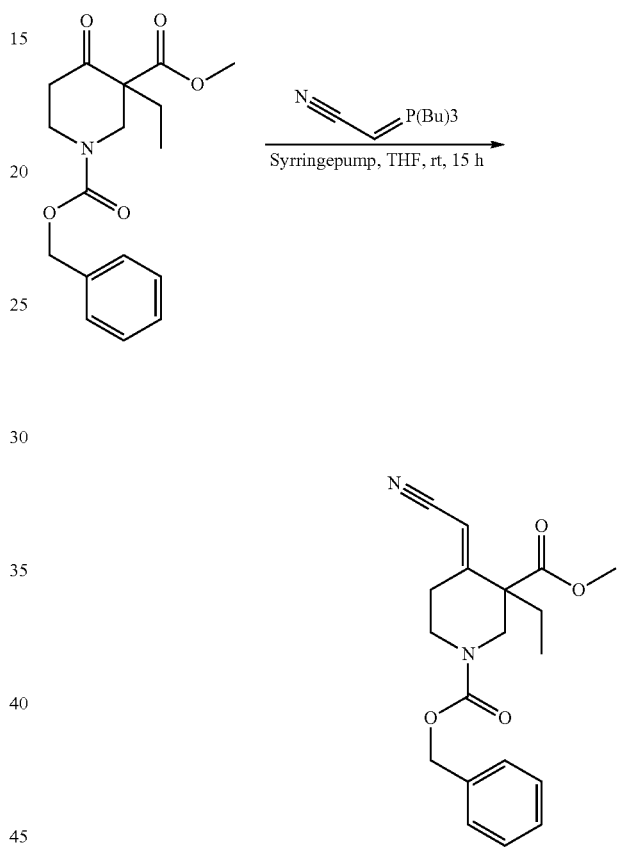

(Tributylphosphoranylidene)acetonitrile (1.20 equiv., 20.3 mmol, 4.90 g, 5.3 mL) was added with a syringe pump over 10 h (0.68 mL/h) to a solution of Intermediate 7 (5.40 g, 16.9 mmol) in dry THF (50 mL). Stirred at rt for 15 h for high conversion into the desired product.

The reaction is stalling if the ylide is present in to high concentrations (possibly ylide decomposition).

The reaction mixture was evaporated directly onto celite and purified by automated column chromatography (ISCO, gradient: Heptane->EtOAc) to afford the single trans-isomer of Intermediate 8 (5.16 g, 15.1 mmol, 89% yield) as a colorless oil.

UPLC-MS: $t_R$=0.78 (M+H$^+$)=343.3

1H NMR (300 MHz, Chloroform-d) δ 7.43-7.30 (m, 5H), 5.35 (s, 1H), 5.16 (s, 2H), 4.22-4.03 (m, 1H), 3.68 (m, 4H), 3.44 (ddd, J=12.9, 8.3, 4.5 Hz, 1H), 3.30 (m, 1H), 2.77 (m, 1H), 2.60 (dddd, J=14.4, 8.3, 5.0, 0.9 Hz, 1H), 1.76 (m, 2H), 0.93-0.84 (m, 3H).

Intermediate 9 (VII, R1=Et)

8a-ethyl-7-(7H-pyrrolo[2,3-d]pyrimidin-4-yl)-3,4,4a,5,6,8-hexahydro-2H-2,7-naphthyridin-1-one

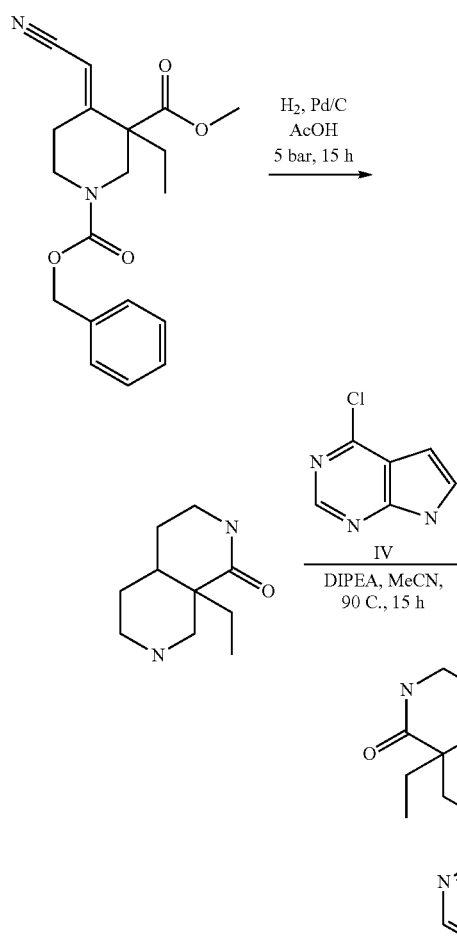

Pd on carbon (0.10 equiv., 1.61 mmol, 1.71 g, 10 mass %) was added to a solution of Intermediate 8 (5.50 g, 16.1 mmol) in AcOH (50 mL) and hydrogenated on Parr apparatus (5 bar) for 20 h for full conversion of SM into the desired lactam.

The mixture was filtered through celite and concentrated in vacuo and coevaporated with toluene to remove trace of acetic acid. The crude product was moved on in next reaction without further purification.

The crude material was dissolved in MeCN (50 mL) and added IV (2.47 g, 16.1 mmol) and DIPEA (8.4 mL, 48.3 mmol). The reaction mixture was refluxed (95° C.) for 15 h for some conversion of the starting chloride into the desired S$_N$Ar product along with a number of minor biproducts.

The crude mixture was evaporated directly onto celite and purified by automated column chromatography (ISCO, first Heptane->DCM, then gradient: DCM->10% MeOH in DCM) to afford Intermediate 9 (2.77 g, 9.24 mmol, 57% yield) as a white foam.

UPLC-MS: t$_R$=0.38 (M+H+)=300.2

1H NMR (600 MHz, Methanol-d4) δ 8.21 (br s, 1H), 8.14 (s, 1H), 7.15 (d, J=3.7 Hz, 1H), 6.80 (d, J=3.6 Hz, 1H), 4.44 (d, J=13.3 Hz, 1H), 4.09 (ddd, J=13.3, 7.0, 4.0 Hz, 1H), 3.72 (ddd, J=12.8, 8.5, 3.8 Hz, 1H), 3.66 (d, J=13.3 Hz, 1H), 3.37 (ddd, J=13.2, 7.6, 5.7 Hz, 1H), 3.31-3.26 (m, 1H), 2.17 (tt, J=8.3, 4.3 Hz, 1H), 2.05 (dddd, J=13.7, 7.8, 5.8, 3.8 Hz, 1H), 1.99-1.86 (m, 2H), 1.82-1.69 (m, 3H), 0.93 (t, J=7.5 Hz, 3H).

Intermediate 10 (VI, R1=Et)

8a-ethyl-7-(7H-pyrrolo[2,3-d]pyrimidin-4-yl)-1,2,3,4,4a,5,6,8-octahydro-2,7-naphthyridine

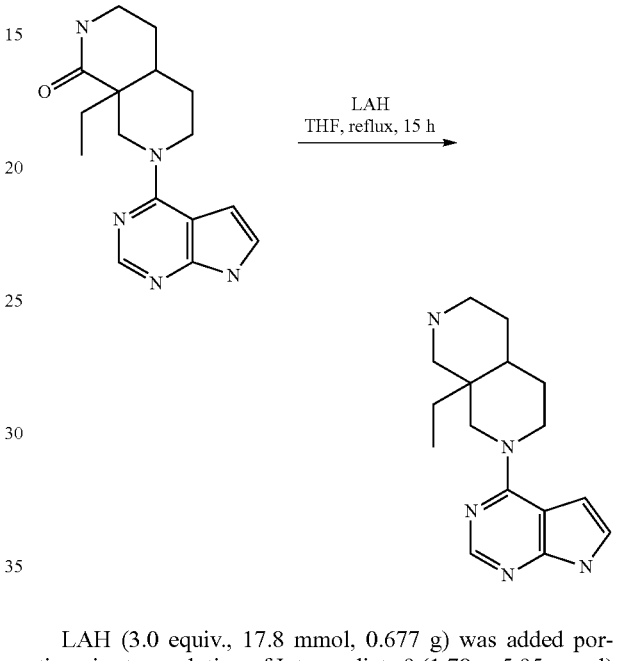

LAH (3.0 equiv., 17.8 mmol, 0.677 g) was added portionwise to a solution of Intermediate 9 (1.78 g, 5.95 mmol) in dry THF (20 mL) and refluxed (80° C.) for 15 h for full conversion of lactam into desired amine.

Cooled on ice, diluted with ether (20 mL), quenched by the Fieser method, dried (magnesium sulfate), filtered to provide the crude Intermediate 10 (750 mg, 2.63 mmol, 44% yield) as a white foam. Pure enough for further manipulation.

UPLC-MS: t$_R$=0.33 (M+H+)=286.3

1H NMR (600 MHz, DMSO-d6) δ 11.63 (s, 1H), 8.09 (s, 1H), 7.14 (d, J=3.5 Hz, 1H), 6.55 (d, J=3.5 Hz, 1H), 4.01-3.60 (m, 4H), 2.86 (br s, 1H), 2.63 (m, 2H), 2.45 (d, J=12.7 Hz, 1H), 1.81-1.37 (m, 7H), 0.78 (t, J=7.5 Hz, 3H).

Intermediate 11 ethyl 2-(tert-butoxycarbonylamino)acetate

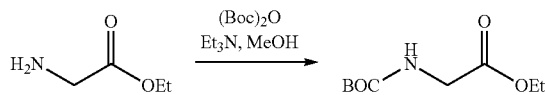

To a solution of ethyl 2-aminoacetate (100 g, 716.33 mmol) in THF (1 L), TEA (144.6 g, 1432.6 mmol) and (Boc)$_2$O (156.3 g, 716.33 mmol) were added slowly at 0° C. and stirred for 16 h at 50° C. On completion of the reaction, volatiles were evaporated under reduced pressure and the resulting residue was washed with 1N NaOH (300 mL) and extracted with EtOAc (1 L×2). The combined organic layers were washed with brine (1 L), dried over anhydrous sodium sulfate and concentrated to afford crude Intermediate 11 (128 g, 88% yield, white solid).

$^1$H NMR (400 MHz, CDCl$_3$) δ 5.04 (br s, 1H), 4.25-4.16 (m, 2H), 3.93-3.82 (m, 2H), 1.39 (m, 9H), 1.31-1.24 (m, 3H).

Intermediate 12

O1-tert-butyl O3-ethyl 4-oxopyrrolidine-1,3-dicarboxylate

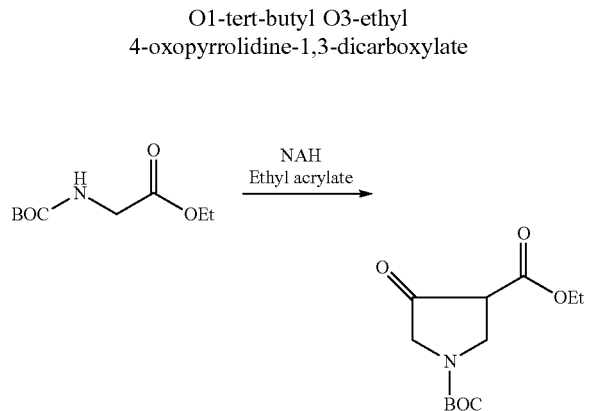

To a suspension of sodium hydride (60%, 18.4 g, 768.47 mmol) in toluene (350 mL) at 0° C. was added portion wise Intermediate 11 (120 g, 591.13 mmol). After stirring for 5 h at this temperature, to the mixture was added drop wise ethyl acrylate (76.8 g, 768.47 mmol). After additional stirring for 2 h at rt, the reaction was quenched with water (200 mL) carefully and extracted with EtOAc (600 mL×2). The combined extract was dried over anhydrous sodium sulfate, concentrated to afford crude Intermediate 12 (50 g, 33% yield, pale brown liquid).

$^1$H NMR (400 MHz, CDCl$_3$) δ 4.28-3.97 (m, 6H), 3.94-3.81 (m, 1H), 1.50-1.39 (s, 9H), 1.36-1.20 (m, 3H).

Intermediate 13

O1-tert-butyl O3-ethyl 3-methyl-4-oxo-pyrrolidine-1,3-dicarboxylate

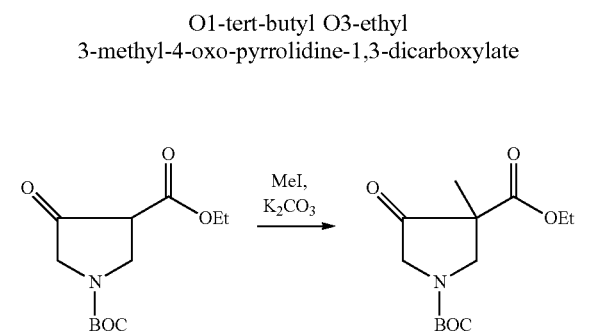

To a solution of Intermediate 12 (50 g, 194.5 mmol) in acetone (500 mL), K$_2$CO$_3$ (53.6 g, 389.1 mmol) and methyl iodide (55.2 g, 389.1 mmol) were added slowly and stirred at 26° C. for 16 h. On completion, reaction mixture was filtered through celite and the filtrate was concentrated and purified by silica gel (100-200 mesh) column chromatography (0-10% EtOAc in petroleum ether as eluent) to afford Intermediate 13 (32 g, 60% Yield, pale yellow liquid).

$^1$H NMR (400 MHz, CDCl$_3$) δ 4.27 (br d, J=11.7 Hz, 1H), 4.19 (dq, J=1.7, 7.1 Hz, 2H), 4.14-3.96 (m, 1H), 3.81 (d, J=19.6 Hz, 1H), 3.46 (br d, J=11.7 Hz, 1H), 1.49 (s, 9H), 1.41 (s, 3H), 1.29-1.22 (m, 3H).

Intermediate 14

O1-tert-butyl O3-ethyl (4Z)-4-(cyanomethylene)-3-methyl-pyrrolidine-1,3-dicarboxylate

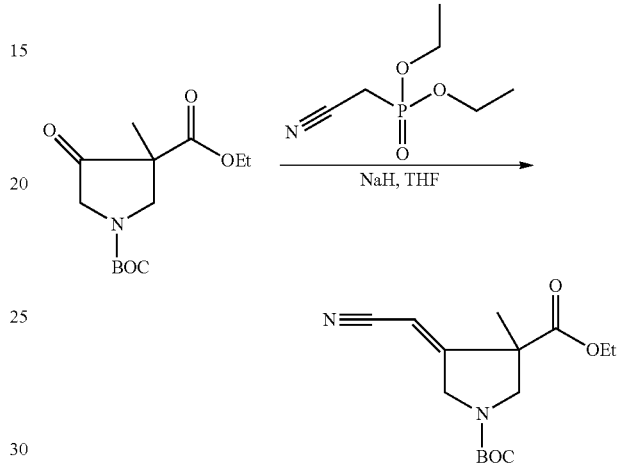

To a solution of sodium hydride (60%, 3.45 g, 143.9 mmol) in THF (500 mL) at 0° C. was added drop wise diethyl cyanomethylphosphonate (25.47 g, 143.9 mmol). After stirring for 1 h at rt, to the mixture was added drop wise a solution of Intermediate 13 (30 g, 110.7 mmol) in THF (50 mL) and was stirred another additional 2 h. On completion, the reaction mixture was quenched with sat. NH$_4$Cl and extracted twice with EtOAc (2×500 mL). The combined organic layers were washed with brine (200 mL), dried over anhydrous sodium sulfate, concentrated and the resulting residue was purified by silica gel column chromatography (0-10% EtOAc in petroleum ether as eluent) to afford Intermediate 14. (19 g, 58% yield, yellow liquid).

$^1$H NMR (300 MHz, CDCl$_3$): δ 6.82-6.60 (m, 1H), 4.34 (br d J=11.4 Hz, 1H), 4.26-4.16 (m, 2H), 3.57 (br d, J=12.1, 1H), 3.36-3.13 (m, 2H), 1.55-1.48 (m, 9H), 1.45 (s, 3H), 1.29 (t, J=7.2 Hz, 3H).

Intermediate 15

O1-tert-butyl O3-ethyl (3R*,4S*)-4-[2-(tert-butoxycarbonylamino)ethyl]-3-methyl-pyrrolidine-1,3-dicarboxylate

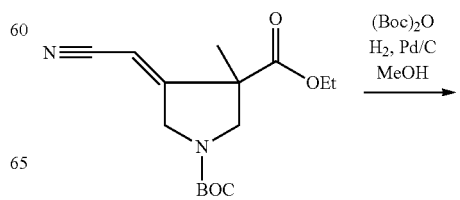

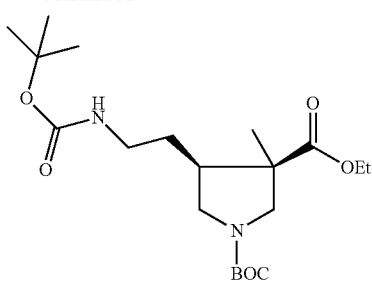

To a solution of Intermediate 14 (9 g, 30.61 mmol) in MeOH (180 mL), (Boc)$_2$O (13.34 g, 61.22 mmol) and wet 10% Pd/C (2.7 g) were added at 0° C. and hydrogenated for 36 h under Parr-Apparatus at 90 psi. On completion, reaction mixture was filtered through celite and the filtrate was concentrated and purified by silica gel (100-200 mesh) column chromatography (0-10% EtOAc in petroleum ether as eluent) to afford Intermediate 15 (11.7 g, 95% yield, light yellow liquid).

$^1$H NMR (400 MHz, CDCl$_3$): δ 4.65-4.45 (m, 1H), 4.20-4.08 (m, 2H), 3.88-3.75 (m, 1H), 3.73-3.51 (m, 2H), 3.24-2.94 (m, 4H), 2.05-1.96 (m, 1H), 1.75-1.55 (m, 2H), 1.51-1.39 (m, 18H), 1.33-1.22 (m, 6H).

Intermediate 16 ethyl (3R*,4S*)-4-(2-aminoethyl)-3-methyl-pyrrolidine-3-carboxylate

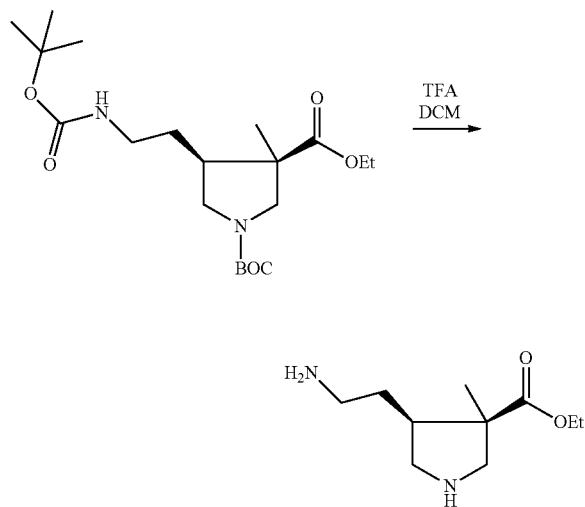

To a solution of Intermediate 15 (12.8 g, 32 mmol) in DCM (250 mL), trifluoroacetic acid (11 g, 96 mmol) was added at 0° C. and stirred for 16 h at 26° C. On completion, reaction mass was washed with sat. NaHCO$_3$ (600 mL) and extracted with EtOAc (500 mL×3), combined organic layers were dried over anhydrous sodium sulfate, concentrated under reduced pressure to afford the crude Intermediate 16 (6.4 g, 99% yield, pale brown gummy solid) which was used for the next step without any further purification.

Intermediate 17

(3aR*,7aS*)-3a-methyl-2,3,5,6,7,7a-hexahydro-1H-pyrrolo[3,4-c]pyridin-4-one

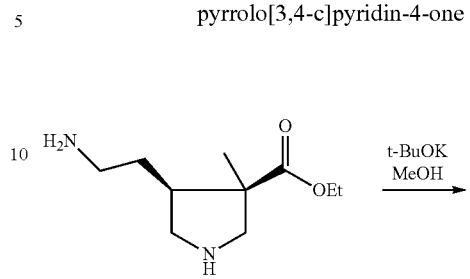

To a solution of crude Intermediate 16 (6.4 g, 32 mmol) in EtOH (300 mL), t-BuOK (17.9 g, 160 mmol) was added and stirred for 16 h at 26° C. On completion, trifluoroacetic acid was added to the reaction mass till pH~3, then volatiles were evaporated under vacuum to afford crude Intermediate 17 (4.93 g, pale brown gummy) which was used for the next step without any further purification.

Intermediate 18

(3aR*,7aS*)-2-benzoyl-3a-methyl-1,3,5,6,7,7a-hexahydropyrrolo[3,4-c]pyridin-4-one

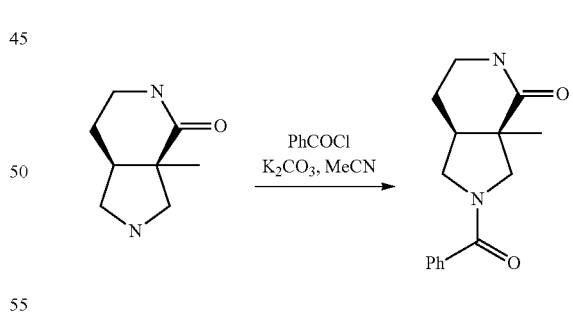

To a solution of Intermediate 17 (4.93 g, 32 mmol) in acetonitrile (60 mL) was added K$_2$CO$_3$ (17.6 g, 128 mmol) and benzoyl chloride (5.3 g, 38.4 mmol) were added slowly at 0° C. and stirred for 16 h at 26° C. On completion reaction mixture was filtered through celite and the filtrate was concentrated and purified by silica (100-200 mesh) column chromatography (0-5% MeOH in DCM as eluent) to afford Intermediate 18 (7.0 g, 84% yield, pale brown gummy).

$^1$H NMR (400 MHz, DMSO): δ 7.53-7.37 (m, 5H), 7.22 (br s, 1H), 3.82-3.66 (m, 2H), 3.53-3.11 (m, 4H), 2.28 (br s, 1H), 1.85 (br s, 1H), 1.65 (br s, 1H), 1.21-1.14 (m, 3H).

Intermediate 19

(3aS*,7aS*)-2-benzyl-3a-methyl-3,4,5,6,7,7a-hexahydro-1H-pyrrolo[3,4-c]pyridine

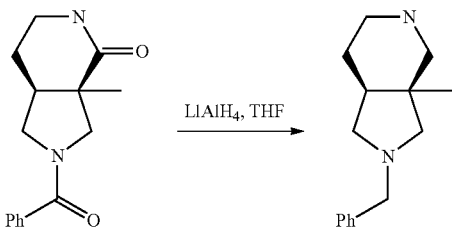 [SMILES: C[C@]12CN(C(=O)c3ccccc3)C[C@H]1CCNC2=O ; C[C@@]12CNCC[C@@H]1CN(Cc1ccccc1)C2]

To a solution of Intermediate 18 (5.5 g, 21.31 mmol) in THF (200 mL), LAH (2.43 g, 63.95 mmol) was added portions wise at 0 C and stirred for 3 h at 80° C. On completion, reaction mass was quenched with ice cold water (30 mL) and 15% NaOH (30 mL), then stirred it for 30 min at rt. Then the reaction mixture was filtered through celite and the filtrate was concentrated under reduce pressure to afford crude Intermediate 19 (4.9 g, 99% yield, pale yellow gummy liquid).

Intermediate 20 tert-butyl (3aR*,7aS*)-2-benzyl-3a-methyl-1,3,4,6,7,7a-hexahydropyrrolo[3,4-c]pyridine-5-carboxylate

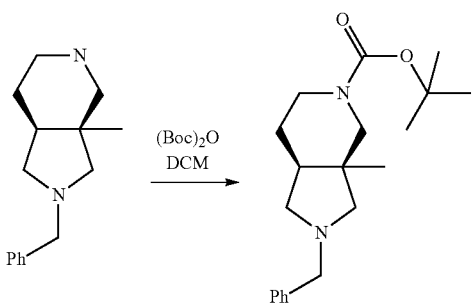 [SMILES: C[C@@]12CNCC[C@@H]1CN(Cc1ccccc1)C2 ; CC(C)(C)OC(=O)N1CC[C@@H]2CN(Cc3ccccc3)C[C@]2(C)C1]

To a solution of Intermediate 19 (4.9 g, 21.31 mmol) in DCM (1 L), TEA (6.45 g, 63.93 mmol) and (Boc)$_2$O (9.3 g, 42.62 mmol) were added slowly at 0° C. and stirred for 16 h at 26° C. On completion of the reaction, volatiles were evaporated under vacuum and purified by silica (100-200 mesh) column chromatography (0-5% MeOH in DCM as eluent) to afford Intermediate 20 (4.8 g, 68% yield, pale yellow liquid).

$^1$H NMR (400 MHz, CDCl$_3$): δ 7.34-7.19 (m, 5H), 3.59 (s, 2H), 3.40-3.13 (m, 4H), 2.76-2.68 (m, 1H), 2.48-2.26 (m, 3H), 1.86-1.66 (m, 2H), 1.63-1.52 (m, 1H), 1.49-1.37 (m, 9H), 1.04 (s, 3H).

Intermediate 21

2-[[4-[(3aR*,7aS*)-2-benzyl-3a-methyl-1,3,4,6,7,7a-hexahydropyrrolo[3,4-c]pyridin-5-yl]pyrrolo[2,3-d]pyrimidin-7-yl]methoxy]ethyl-trimethyl-silane

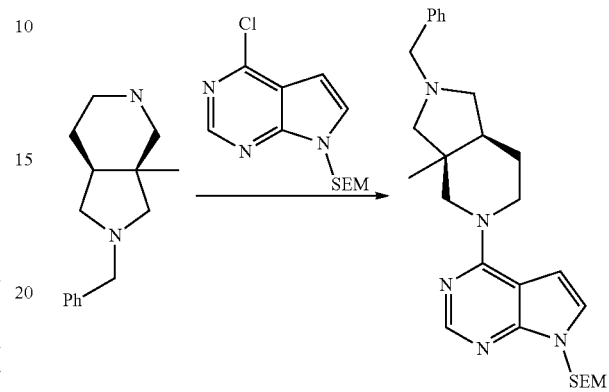

To a solution of Intermediate 19 (745 mg, 3.24 mmol) and DIPEA (1.3 g, 10 mmol) in dioxane (30 mL) was added 2-[(4-chloropyrrolo[2,3-d]pyrimidin-7-yl)methoxy]ethyl-trimethyl-silane (850 mg, 2.99 mmol). The mixture was stirred overnight at 100° C. After cooling to rt the mixture was evaporated to remove volatiles, and the residue was dissolved in DCM and purified by chromatography on silica gel (DCM:MeOH 25:1) to give Intermediate 21 as a colorless oil.

Intermediate 22 tert-butyl N-[[(3aS*,7aS*)-3a-methyl-5-[7-(2-trimethylsilylethoxymethyl)pyrrolo[2,3-d]pyrimidin-4-yl]-1,3,4,6,7,7a-hexahydropyrrolo[3,4-c]pyridin-2-yl]sulfonyl]carbamate

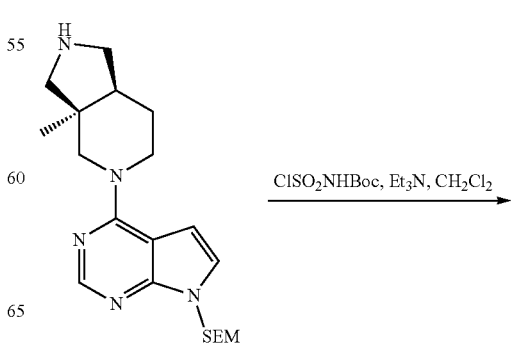

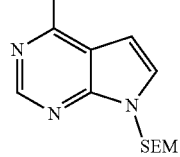

-continued

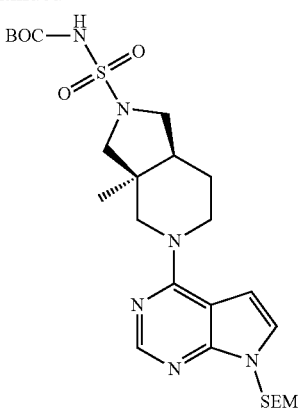

To a solution of intermediate 23 (50 mg, 0.13 mmol) in DCM (5 mL) under argon was added triethylamine (54 μL, 0.39 mmol). The mixture was cooled on ice, tert-butyl N-chlorosulfonylcarbamate (31 mg, 0.14 mmol) was added, and the mixture was allowed to warm to rt. and stirred for 2 h. It was evaporated to dryness and the residue was purified using prep HPLC (acidic) to afford intermediate 22 (33 mg, 45% yield) as a white solid.

UPLC-MS: $t_R$=0.92 (M+H$^+$)=567.4

$^1$H NMR (600 MHz, Chloroform-d) δ 8.33 (s, 1H), 7.37 (br s, 1H), 7.10 (d, J=3.7 Hz, 1H), 6.49 (d, J=3.8 Hz, 1H), 5.58 (s, 2H), 4.17-4.12 (m, 1H), 4.11 (d, J=13.8 Hz, 1H), 3.85 (dd, J=9.6, 6.9 Hz, 1H), 3.71-3.65 (m, 1H), 3.60 (d, J=13.8 Hz, 1H), 3.57-3.51 (m, 3H), 3.43 (d, J=9.6 Hz, 1H), 3.26 (d, J=9.6 Hz, 1H), 2.17-2.10 (m, 1H), 1.96-1.90 (m, 1H), 1.74-1.66 (m, 1H), 1.43 (s, 9H), 1.17 (s, 3H), 0.94-0.89 (m, 2H), −0.05 (s, 9H).

Intermediate 23

2-[[4-[(3aR*,7aS*)-3a-methyl-2,3,4,6,7,7a-hexahydro-1H-pyrrolo[3,4-c]pyridin-5-yl]pyrrolo[2,3-d]pyrimidin-7-yl]methoxy]ethyl-trimethyl-silane

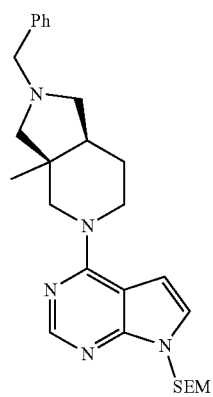

-continued

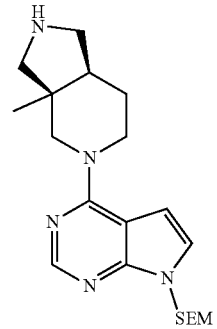

To a solution of Intermediate 21 (63 mg, 0.13 mmol) in THF (1.5 mL) and methanol (1 mL) in a 4 mL screwcap vial was added ammonium formate (50 mg, 0.79 mmol), the vial was flushed with argon, and 10% Pd/C (ca. 5 mg) was added. The mixture was shaken at 60° C. overnight, filtered through celite and washed with methanol. The filtrate was evaporated to dryness to afford intermediate 23 (41 mg, 80% yield) which was used directly in the next step without further purification.

UPLC-MS: $t_R$=0.65 (M+H$^+$)=388.4

$^1$H NMR (300 MHz, Chloroform-d) δ 8.31 (s, 1H), 7.05 (d, J=3.7 Hz, 1H), 6.56 (d, J=3.7 Hz, 1H), 5.56 (s, 2H), 4.07-3.63 (m, 4H), 3.58-3.47 (m, 2H), 3.29 (dd, J=11.0, 6.8 Hz, 1H), 2.97-2.68 (m, 3H), 2.06-1.84 (m, 2H), 1.82-1.62 (m, 1H), 1.12 (s, 3H), 0.96-0.86 (m, 2H), −0.05 (s, 9H).

Intermediates 24 and 25

6-[(3aS,7aS)-3a-methyl-5-[7-(2-trimethylsilylethoxymethyl)pyrrolo[2,3-d]pyrimidin-4-yl]-1,3,4,6,7,7a-hexahydropyrrolo[3,4-c]pyridin-2-yl]pyridine-3-carbonitrile (24) and 6-[(3aR,7aR)-3a-methyl-5-[7-(2-trimethylsilylethoxymethyl)pyrrolo[2,3-d]pyrimidin-4-yl]-1,3,4,6,7,7a-hexahydropyrrolo[3,4-c]pyridin-2-yl]pyridine-3-carbonitrile (25)

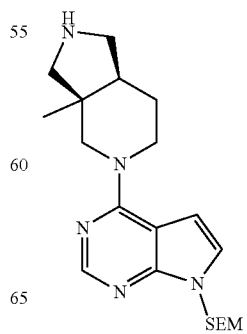

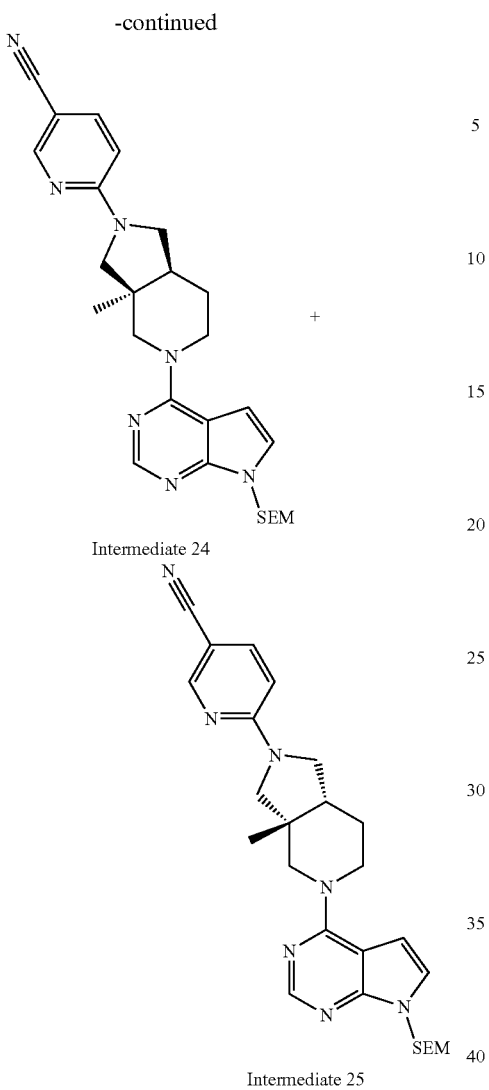

Intermediate 24

Intermediate 25

To a solution of racemic intermediate 23 (226 mg, 0.583 mmol) in DMF (5 mL) was added 6-chloropyridine-3-carbonitrile (88.9 mg, 0.641 mmol) followed by DBU (192 µL, 1.28 mmol). The solution was stirred at 50° C. for 1.5 h, volatiles were evaporated, and the residue was purified by chromatography using a CombiFlash system (12 g silica gel column, EtOAc:heptane 0:100→30:70) to afford racemic product as a white foam (240 mg, 84% yield).

UPLC-MS: $t_R$=0.96 (M+H$^+$)=490.5

$^1$H NMR (600 MHz, DMSO-d6) δ 8.41 (br d, 1H), 8.19 (s, 1H), 7.79 (br s, 1H), 7.37 (d, J=3.7 Hz, 1H), 6.75 (d, J=3.7 Hz, 1H), 6.50 (br d, 1H), 5.52 (d, J=10.8 Hz, 1H), 5.50 (d, J=10.9 Hz, 1H), 4.10-3.90 (m, 2H), 3.89-3.69 (m, 2H), 3.67-3.55 (m, 1H), 3.51-3.46 (m, 2H), 3.46-3.12 (m, 3H), 2.33-2.16 (m, 1H), 1.92-1.84 (m, 1H), 1.55-1.46 (m, 1H), 1.10 (s, 3H), 0.83-0.77 (m, 2H), −0.11 (s, 9H).

The pure enantiomers were obtained by chiral HPLC separation. The racemic material was dissolved to 24 mg/mL in acetonitrile and was then purified by HPLC. Each injection was 0.75 mL (18 mg). The column used was a Lux A2 (20 mm×250 mm, 5 µm). The eluent was MeCN/isopropanol in a 90/10 ratio. The flow rate was 21 mL/min at a wavelength of 280 nm. The wet fractions were then evaporated to dryness using a rotary evaporator and dried in a vacuum oven at 40° C. and 5 mbar to afford constant weight. The final analysis was performed by HPLC using a Lux A2 (4.6 mm×250 mm, 5 µm). The eluent was MeCN/isopropanol in a 90/10 ratio. The flow rate was 1 mL/min. Thus were obtained Intermediate 24 (114 mg, 99.1% ee, anal. HPLC $t_R$=5.6 min) and Intermediate 25 (108 mg, 98.4% ee, anal. HPLC $t_R$=4.5 min).

Intermediate 26

Methyl 2-[(3aS*,7aS*)-3a-methyl-5-[7-(2-trimethyl-silylethoxymethyl)pyrrolo[2,3-d]pyrimidin-4-yl]-1,3,4,6,7,7a-hexahydropyrrolo[3,4-c]pyridin-2-yl]-5-bromo-pyridine-3-carboxylate

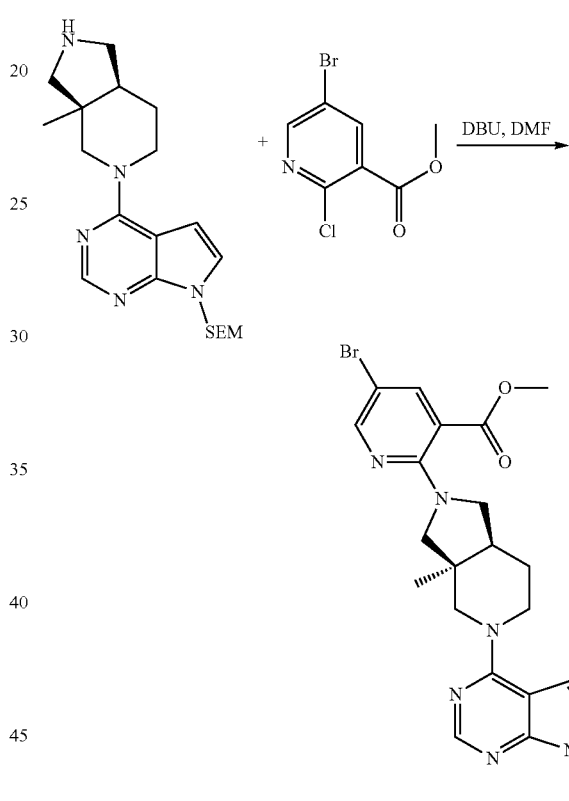

To a solution of intermediate 23 (200 mg, 0.433 mmol) in DMF (6 mL) was added methyl 5-bromo-2-chloro-pyridine-3-carboxylate (119 mg, 0.475 mmol) followed by DBU (0.14 mL, 0.95 mmol). The mixture was heated at 50° C. for 4 h and was then allowed to cool to rt overnight. Volatiles were evaporated and the residue was purified by chromatography using a Grace system (12 g silica gel column, EtOAc:heptane 0:100→40:60) to afford Intermediate 26 (261 mg, quant.) as a colorless oil.

UPLC-MS: $t_R$=1.07 (M+H$^+$)=601.5

$^1$H NMR (600 MHz, Chloroform-d) δ 8.33 (s, 1H), 8.22 (d, J=2.5 Hz, 1H), 7.94 (d, J=2.5 Hz, 1H), 7.09 (d, J=3.7 Hz, 1H), 6.51 (d, J=3.8 Hz, 1H), 5.58 (s, 2H), 4.09-4.01 (m, 1H), 3.92 (d, J=13.7 Hz, 1H), 3.87-3.79 (m, 1H), 3.77 (s, 3H), 3.72-3.64 (m, 2H), 3.57-3.50 (m, 2H), 3.42 (dd, J=11.3, 5.6 Hz, 1H), 3.34 (d, J=11.1 Hz, 1H), 3.15 (d, J=11.1 Hz, 1H), 2.20-2.14 (m, 1H), 1.99-1.91 (m, 1H), 1.70-1.61 (m, 1H), 1.16 (s, 3H), 0.94-0.89 (m, 2H), −0.05 (s, 9H).

Intermediate 27

[2-[(3aS*,7aS*)-3a-methyl-5-[7-(2-trimethylsilylethoxymethyl)pyrrolo[2,3-d]pyrimidin-4-yl]-1,3,4,6,7,7a-hexahydropyrrolo[3,4-c]pyridin-2-yl]-5-bromo-3-pyridyl]methanol

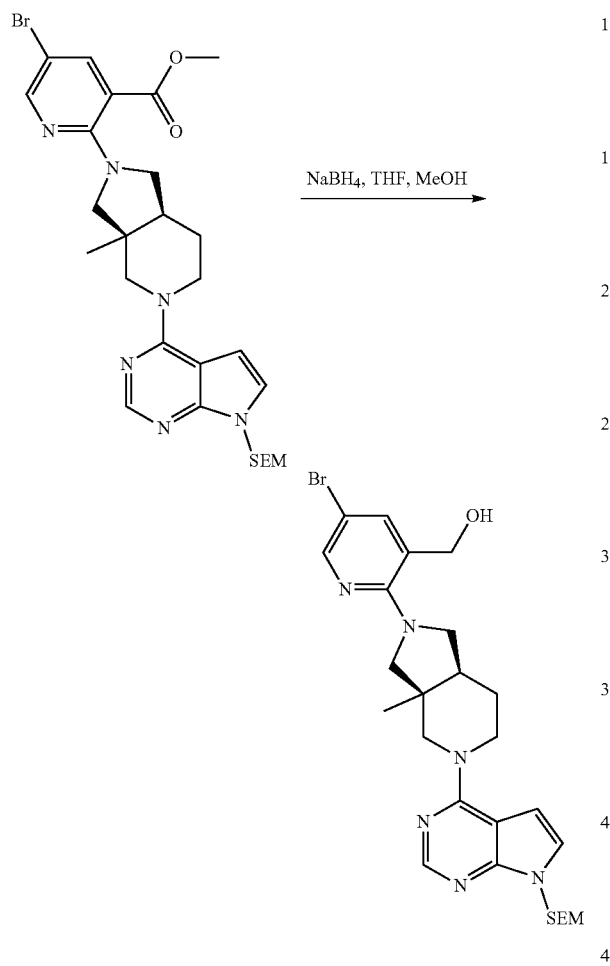

To a solution of intermediate 26 (246 mg, 0.409 mmol) in THF (3 mL) and methanol (3 mL) was added NaBH$_4$ (92.8 mg, 2.45 mmol) and the mixture was stirred at rt overnight. Another portion of NaBH$_4$ (92.8 mg, 2.45 mmol) was added and stirring was continued for 3 h. This was repeated two more times after which the mixture was evaporated to dryness. The residue was cooled on ice, water (20 mL) was added, and the mixture was extracted with EtOAc (4×25 mL). The combined EtOAc phases were washed with brine (30 mL), dried over MgSO$_4$, filtered and evaporated. The residue was purified by chromatography using a Grace system (12 g silica gel column, EtOAc:heptane 0:100→50:50) to afford intermediate 27 (36 mg, 15% yield) and recovered starting material (110 mg).

UPLC-MS: t$_R$=0.98 (M+H+)=573.5

$^1$H NMR (600 MHz, Chloroform-d) δ 8.31 (s, 1H), 8.07 (d, J=2.4 Hz, 1H), 7.57 (d, J=2.4 Hz, 1H), 7.08 (d, J=3.7 Hz, 1H), 6.53 (d, J=3.8 Hz, 1H), 5.56 (s, 2H), 4.62 (d, J=13.2 Hz, 1H), 4.58 (d, J=13.1 Hz, 1H), 4.02-3.96 (m, 1H), 3.90 (d, J=13.6 Hz, 1H), 3.88-3.84 (m, 1H), 3.81 (dd, J=10.4, 7.3 Hz, 1H), 3.77 (d, J=13.6 Hz, 1H), 3.61 (dd, J=10.4, 5.8 Hz, 1H), 3.57 (d, J=10.3 Hz, 1H), 3.55-3.50 (m, 2H), 3.35 (d, J=10.3 Hz, 1H), 2.61 (br s, 1H), 2.18-2.12 (m, 1H), 2.00-1.93 (m, 1H), 1.75-1.67 (m, 1H), 1.17 (s, 3H), 0.94-0.88 (m, 2H), −0.05 (s, 9H).

Intermediate 28

[2-[(3aS*,7aS*)-3a-methyl-5-[7-(2-trimethylsilylethoxymethyl)pyrrolo[2,3-d]pyrimidin-4-yl]-1,3,4,6,7,7a-hexahydropyrrolo[3,4-c]pyridin-2-yl]-3-pyridyl]methanol

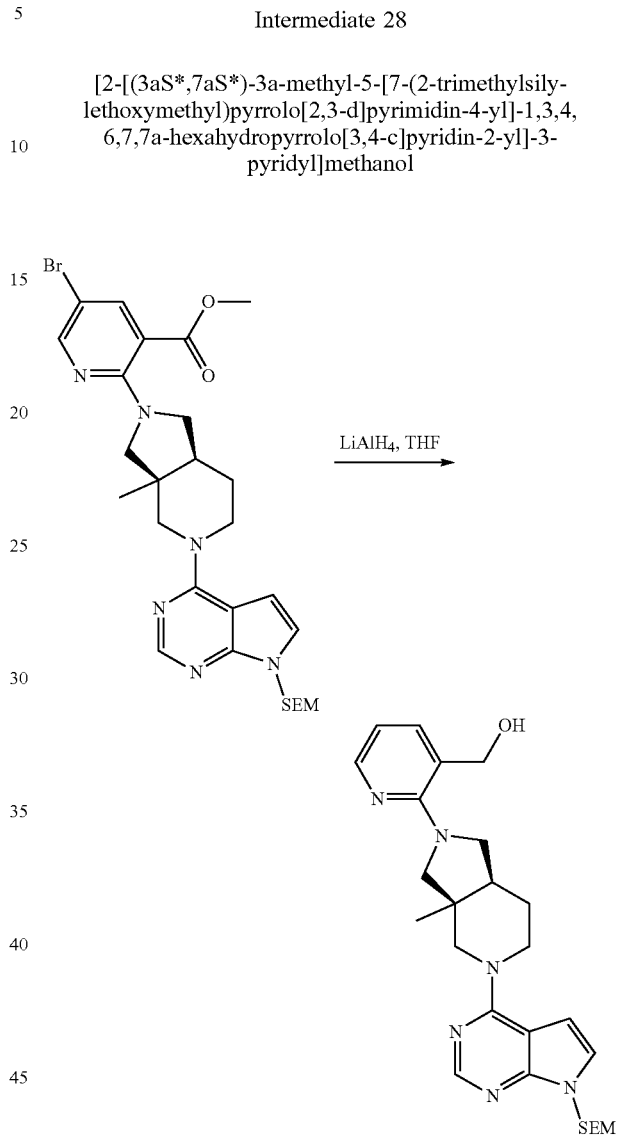

To a solution of intermediate 26 (55 mg, 0.091 mmol) in dry THF (1 mL) under argon at 0° C. was added LiAlH$_4$ (1.0 M in THF, 0.18 mL, 0.18 mmol) and the mixture was stirred for 20 min. The reaction was quenched by the sequential addition of water (7 μL), 15% aq. NaOH (7 μL) and water (21 μL) and the mixture was stirred at rt for 1 h. The precipitated lithium salts were filtered off, the filtrate was evaporated and the residue was purified by prep. HPLC (acidic method) to afford intermediate 27 (12 mg, 23% yield) and intermediate 28 (5 mg, 11% yield).

UPLC-MS: t$_R$=0.71 (M+H+)=495.6

$^1$H NMR (600 MHz, Chloroform-d) δ 8.34 (s, 1H), 8.12 (dd, J=4.9, 1.9 Hz, 1H), 7.48 (dd, J=7.3, 1.9 Hz, 1H), 7.08 (d, J=3.7 Hz, 1H), 6.66 (dd, J=7.3, 4.9 Hz, 1H), 6.55 (d, J=3.7 Hz, 1H), 5.58 (s, 2H), 4.68 (d, J=12.8 Hz, 1H), 4.64 (d, J=12.8 Hz, 1H), 4.02-3.95 (m, 1H), 3.95-3.83 (m, 4H), 3.69 (dd, J=10.3, 6.0 Hz, 1H), 3.61 (d, J=10.3 Hz, 1H), 3.56-3.51 (m, 2H), 3.43 (d, J=10.2 Hz, 1H), 2.21-2.15 (m, 1H), 2.04-1.97 (m, 1H), 1.80-1.73 (m, 1H), 1.20 (s, 3H), 0.94-0.89 (m, 2H), −0.05 (s, 9H).

Intermediates 29 and 30

(3aS,7aS)-3a-methyl-5-[7-(2-trimethylsilylethoxymethyl)pyrrolo[2,3-d]pyrimidin-4-yl]-1,3,4,6,7,7a-hexahydropyrrolo[3,4-c]pyridine-2-carbonitrile (29) and (3aR,7aR)-3a-methyl-5-[7-(2-trinnethylsilylethoxymethyl)pyrrolo[2,3-d]pyrimidin-4-yl]-1,3,4,6,7,7a-hexahydropyrrolo[3,4-c]pyridine-2-carbonitrile (30)

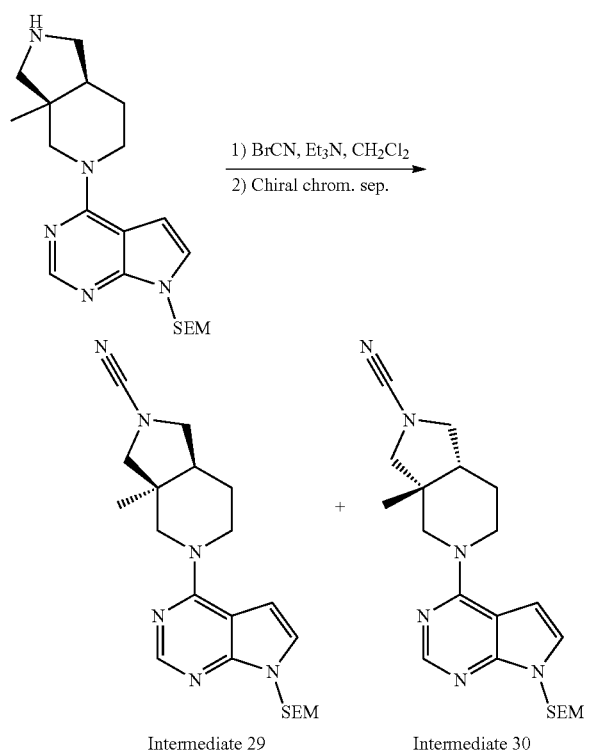

Intermediate 29     Intermediate 30

To a solution of intermediate 23 (686 mg, 1.52 mmol) in DCM (10 mL) was added triethylamine (0.42 mL, 3.0 mmol) followed by cyanogen bromide (180 mg, 1.7 mmol) and the solution was stirred under argon at rt for 1 h (complete by LCMS). The reaction mixture was evaporated onto silica gel and the product was purified by chromatography using a CombiFlash system (40 g silica gel column, gradient elution, EtOAc:heptane 0:100→80:20) to afford racemic product (589 mg, 81% yield) as a pale yellow oil which retained 14% EtOAc as determined by $^1$H NMR.

UPLC-MS: $t_R$=0.83 (M+H+)=413.4

$^1$H NMR (600 MHz, DMSO-$d_6$) δ 8.18 (s, 1H), 7.36 (d, J=3.7 Hz, 1H), 6.73 (d, J=3.7 Hz, 1H), 5.51 (s, 2H), 3.95-3.89 (m, 1H), 3.86 (d, J=13.9 Hz, 1H), 3.85-3.80 (m, 1H), 3.79 (d, J=13.8 Hz, 1H), 3.63 (dd, J=9.4, 7.3 Hz, 1H), 3.52-3.47 (m, 2H), 3.38 (dd, J=9.4, 5.8 Hz, 1H), 3.26 (d, J=9.3 Hz, 1H), 3.13 (d, J=9.3 Hz, 1H), 2.14-2.08 (m, 1H), 1.86-1.80 (m, 1H), 1.55-1.48 (m, 1H), 1.04 (s, 3H), 0.83-0.78 (m, 2H), −0.10 (s, 9H).

The pure enantiomers were obtained by chiral SFC separation. The racemic material was dissolved to 50 mg/mL in methanol and was then purified by SFC. Each injection was 0.25 mL (12.5 mg). The column used was a Lux C1 (20 mm×250 mm, 5 μm). The eluent was MeOH/$CO_2$ 25%. The flow rate was 50 mL/min at a wavelength of 216 nm. The wet fractions were then evaporated to near dryness using a rotary evaporator, transferred into the final vessel with DCM which was removed under a stream of nitrogen at 40° C. before being stored in a vacuum oven at 40° C. and 5 mbar for 6 hours to afford a yellow gum. The final analysis was performed by SFC using a Lux C1 (4.6 mm×250 mm, 5 μm). The eluent was MeOH/$CO_2$ 30%. The flow rate was 4 mL/min. Thus were obtained Intermediate 29 (237 mg, 99.8% ee, anal. SFC $t_R$=1.87 min) and Intermediate 30 (243 mg, 96.6% ee, anal. SFC $t_R$=2.01 min).

Intermediate 31

2-[[4-(8a-methyl-1,3,4,4a,5,6,7,8-octahydro-2,7-naphthyridin-2-yl)pyrrolo[2,3-d]pyrimidin-7-yl]methoxy]ethyl-trimethyl-silane

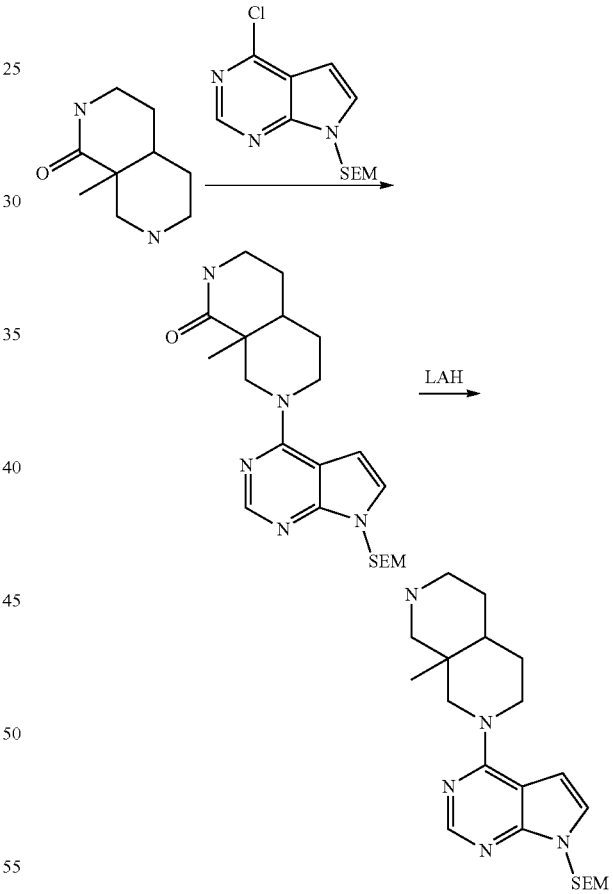

Intermediate 4 (380 mg, 1.86 mmol), 2-[(4-chloropyrrolo[2,3-d]pyrimidin-7-yl)methoxy]ethyl-trimethyl-silane (579 mg, 2.05 mmol), and DIPEA (2 mL) was mixed in dioxane (120 mL) and stirred at 100° C. for 18 h.

The reaction mixture was concentrated in vacuo and purified by column chromatography on silica (heptanes:EA 2:1 to DCM:MeOH 40:1) to afford the SEM-protected lactam intermediate (350 mg, 45% yield) as a yellow gum.

This was dissolved in THF (10 mL) and cooled on ice bath followed by addition of LAH (200 mg, 5.26 mmol) and the stirred at rt overnight. The reaction mixture was cooled on ice bath and quenched followed by purification by column chromatography on silica (DCM:MeOH 15:1) to afford Intermediate 31 (174 mg, 51% yield) as an off-white foam and used as is.

EXAMPLES

Example 2

(4aR*,8aS*)-8a-methyl-7-(7H-pyrrolo[2,3-d]pyrimidin-4-yl)-3,4,4a,5,6,8-hexahydro-1H-2,7-naphthyridine-2-carbonitrile (Compound 2)

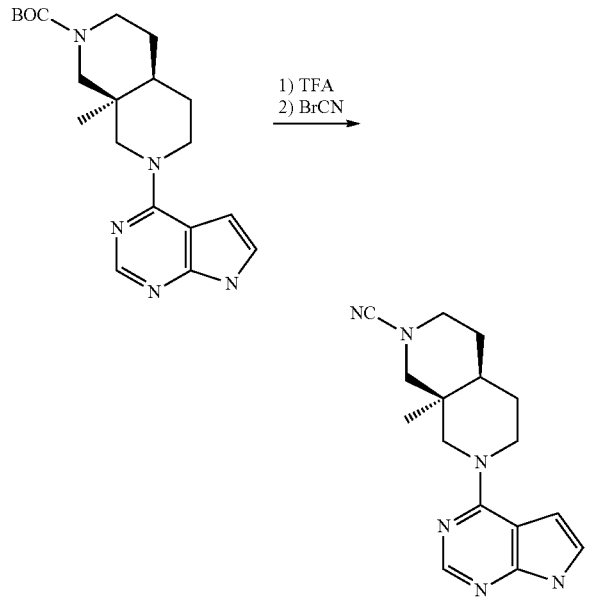

TFA (15 mL) was added to a solution of Intermediate 6 (2.06 g, 5.55 mmol) in DCM (50 mL) and stirred at rt for 3 h for full deprotection. Then evaporated to dryness and coevaporated with toluene. The crude product was redissolved in MeOH (30 mL) and added sodium bicarbonate (5.0 equiv., 27.8 mmol, 2.33 g) and cooled on ice for 10 min. Then cyanogen bromide (1.1 equiv., 6.11 mmol, 647 mg) was added portionwise to the mixture and stirred under argon at rt for 1 h for full conversion into the desired cyanamide. The crude mixture was filtered and evaporated directly onto celite and purified by purified by automated column chromatography (ISCO, gradient: DCM->10% MeOH in DCM) to afford the desired Example 2 (692 mg, 2.34 mmol, 42% yield) as a white solid as racemic single diastereomer.

UPLC-MS: $t_R$=0.45 (M+H+)=297.3

1H NMR (300 MHz, Chloroform-d) δ 9.81 (s, 1H), 8.31 (d, J=1.1 Hz, 1H), 7.08 (d, J=3.6 Hz, 1H), 6.49 (d, J=3.6 Hz, 1H), 4.29 (m, 2H), 3.59 (s, 1H), 3.39-3.11 (m, 4H), 2.86 (d, J=13.0 Hz, 1H), 2.00 (dd, J=9.2, 4.8 Hz, 1H), 1.89-1.64 (m, 4H), 1.18 (d, J=1.1 Hz, 3H)

The pure enantiomers were obtained by chiral SFC separation. The racemic material was dissolved to 32 mg/mL in methanol and was then purified by SFC. Each injection was 1.5 mL (48 mg). The column used was a Amy-C (20 mm×250 mm, 5 μm). The eluent was MeOH/$CO_2$ 25%. The flow rate was 21 mL/min at a wavelength of 220 nm. The wet fractions were then evaporated to near dryness using a rotary evaporator, transferred into the final vessel with DCM which was removed under a stream of nitrogen at 40° C. before being stored in a vacuum oven at 40° C. and 5 mbar for 6 h to afford off-white solids. The final analysis was performed by SFC using a Lux A2 (4.6 mm×250 mm, 5 μm). The flow rate was 1 mL/min and wavelength 254 nm.

Thus were obtained Example 1 and Example 3.

Example 1

(4aR,8aS)-8a-methyl-7-(7H-pyrrolo[2,3-d]pyrimidin-4-yl)-3,4,4a,5,6,8-hexahydro-1H-2,7-naphthyridine-2-carbonitrile (Compound 1)

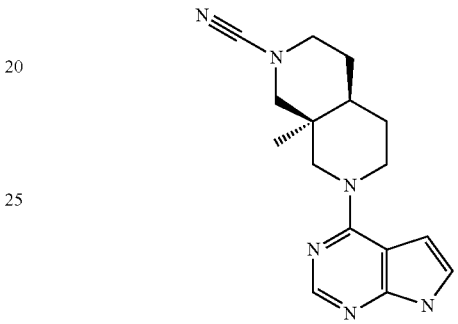

138 mg, 99.9% ee, anal SFC $t_R$=8.78 min
UPLC-MS Method 5: $t_R$=1.76 (M+H$^+$)=297.17
1H NMR (300 MHz, Chloroform-d) δ 9.81 (s, 1H), 8.31 (d, J=1.1 Hz, 1H), 7.08 (d, J=3.6 Hz, 1H), 6.49 (d, J=3.6 Hz, 1H), 4.29 (m, 2H), 3.59 (s, 1H), 3.39-3.11 (m, 4H), 2.86 (d, J=13.0 Hz, 1H), 2.00 (dd, J=9.2, 4.8 Hz, 1H), 1.89-1.64 (m, 4H), 1.18 (d, J=1.1 Hz, 3H)

Example 3

(4aS,8aR)-8a-methyl-7-(7H-pyrrolo[2,3-d]pyrimidin-4-yl)-3,4,4a,5,6,8-hexahydro-1H-2,7-naphthyridine-2-carbonitrile (Compound 3)

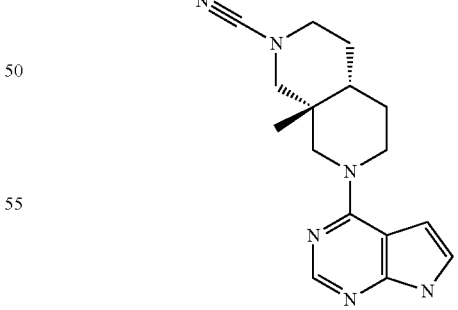

143 mg, 99.9% ee, anal. SFC $t_R$=10.01 min
UPLC-MS Method 5: $t_R$=1.76 (M+H$^+$)=297.17
1H NMR (300 MHz, Chloroform-d) δ 9.81 (s, 1H), 8.31 (d, J=1.1 Hz, 1H), 7.08 (d, J=3.6 Hz, 1H), 6.49 (d, J=3.6 Hz, 1H), 4.29 (m, 2H), 3.59 (s, 1H), 3.39-3.11 (m, 4H), 2.86 (d, J=13.0 Hz, 1H), 2.00 (dd, J=9.2, 4.8 Hz, 1H), 1.89-1.64 (m, 4H), 1.18 (d, J=1.1 Hz, 3H)

Examples 4-8 and 10-12 and 14

These examples are prepared according to the below general procedure for nucleophilic aromatic substitution and SEM deprotection

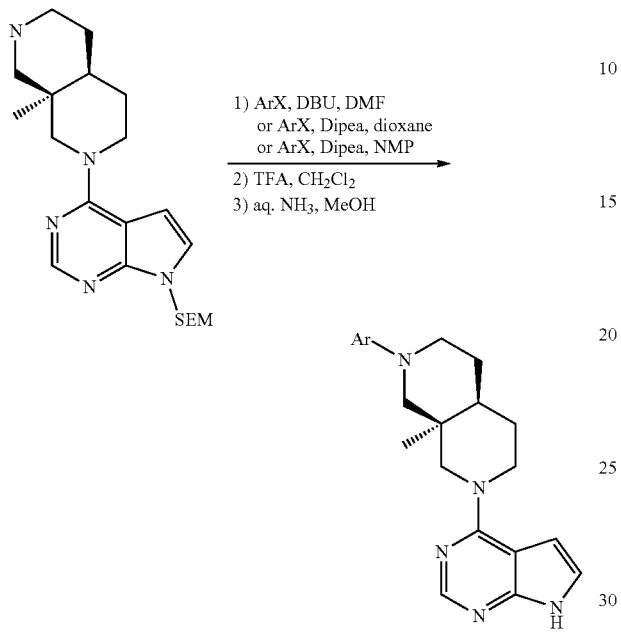

1) ArX, DBU, DMF
or ArX, Dipea, dioxane
or ArX, Dipea, NMP
2) TFA, CH$_2$Cl$_2$
3) aq. NH$_3$, MeOH The compounds of examples 4-8, 10-12 and 14 were prepared according to the following method: A solution of intermediate 31 (100 mg, 0.25 mmol) and base (1.2 eq) either DBU or Dipea in DMF, dioxane or NMP (3 mL) was added to the respective heteroaryl halide (1.2 equiv.) in a 4 mL screwcap vial, and the mixture was shaken at the temperature and time indicated below. The reaction mixture was purified by prep HPLC (basic) to afford the SEM-protected intermediates, which were dissolved in DCM (3 mL) and TFA (2 mL). After standing for 1 h at rt volatiles were evaporated and the residue was dissolved in methanol (5 mL) and aq. NH$_3$ (3 mL). After standing at rt for 6 h the reaction mixture was purified by prep HPLC (basic) afford pure products.

Example 4

5-[(4aR*,8aS*)-8a-methyl-7-(7H-pyrrolo[2,3-d]pyrimidin-4-yl)-3,4,4a,5,6,8-hexahydro-1H-2,7-naphthyridin-2-yl]pyrazine-2-carbonitrile (Compound 4)

Using 5-chloropyrazine-2-carbonitrile as heteroarylhalide, DBU and DMF, stirred at rt for 2 h.
UPLC-MS Method 5: $t_R$=1.98 (M+H$^+$)=375.44

Example 5

6-[(4aR*,8aS*)-8a-methyl-7-(7H-pyrrolo[2,3-d]pyrimidin-4-yl)-3,4,4a,5,6,8-hexahydro-1H-2,7-naphthyridin-2-yl]pyridine-3-carbonitrile (Compound 5)

Using 6-bromopyridine-3-carbonitrile, Dipea and dioxane, stirred at 100° C. for 10 h.
UPLC-MS Method 5: $t_R$=2.06 (M+H$^+$)=374.45

Example 6

6-[(4aR*,8aS*)-8a-methyl-7-(7H-pyrrolo[2,3-d]pyrimidin-4-yl)-3,4,4a,5,6,8-hexahydro-1H-2,7-naphthyridin-2-yl]pyridazine-3-carbonitrile (Compound 6)

Using 6-chloropyridazine-3-carbonitrile, DBU and DMF, stirred at rt for 2 h.
UPLC-MS Method 5: $t_R$=1.90 (M+H$^+$)=375.44

Example 7

2-[(4aR*,8aS*)-8a-methyl-7-(7H-pyrrolo[2,3-d]pyrimidin-4-yl)-3,4,4a,5,6,8-hexahydro-1H-2,7-naphthyridin-2-yl]pyrimidine-5-carbonitrile (Compound 7)

Using 2-chloropyrimidine-5-carbonitrile, DBU and DMF, stirred at 50° C. for 3 h.
UPLC-MS Method 5: $t_R$=2.08 (M+H$^+$)=375.44

Example 8

6-[(4aS*,8aR*)-8a-methyl-7-(7H-pyrrolo[2,3-d]pyrimidin-4-yl)-3,4,4a,5,6,8-hexahydro-1H-2,7-naphthyridin-2-yl]-4-methyl-pyridine-3-carbonitrile (Compound 8)

Using 6-bromo-4-methyl-pyridine-3-carbonitrile, Dipea and dioxane, stirred at 100° C. for 10 h.
UPLC-MS Method 5: $t_R$=2.12 (M+H$^+$)=388.48

Example 10

6-[(4aS*,8aR*)-8a-methyl-7-(7H-pyrrolo[2,3-d]pyrimidin-4-yl)-3,4,4a,5,6,8-hexahydro-1H-2,7-naphthyridin-2-yl]-2-methyl-pyridine-3-carbonitrile (Compound 10)

Using 6-chloro-2-methyl-pyridine-3-carbonitrile, Dipea and dioxane, stirred at 100° C. overnight.
UPLC-MS Method 5: $t_R$=2.17 (M+H$^+$)=388.48

Example 11

6-[(4aS*,8aR*)-8a-methyl-7-(7H-pyrrolo[2,3-d]pyrimidin-4-yl)-3,4,4a,5,6,8-hexahydro-1H-2,7-naphthyridin-2-yl]-5-methyl-pyridine-3-carbonitrile (Compound 11)

Using 6-fluoro-5-methyl-pyridine-3-carbonitrile, Dipea and dioxane, stirred at 100° C. for 10 h.
UPLC-MS Method 5: $t_R$=2.12 (M+H$^+$)=388.48

Example 12

(4aS*,8aR*)-2-(5-bromo-4-methyl-2-pyridyl)-8a-methyl-7-(7H-pyrrolo[2,3-d]pyrimidin-4-yl)-3,4,4a,5,6,8-hexahydro-1H-2,7-naphthyridine (Compound 12)

Using 5-bromo-2-chloro-4-methyl-pyridine, Dipiea and DMF, stirred at 100° C. for 3 h.
UPLC-MS Method 5: $t_R$=2.32 (M+H$^+$)=442.37

Example 14

(4aS*,8aR*)-2-(5-bromo-6-methyl-2-pyridyl)-8a-methyl-7-(7H-pyrrolo[2,3-d]pyrimidin-4-yl)-3,4,4a,5,6,8-hexahydro-1H-2,7-naphthyridine (Compound 14)

Using 3-bromo-6-chloro-2-methyl-pyridine, Dipea and NMP, stirred at 100° C. for 3 h.
UPLC-MS Method 5: $t_R$=2.45 (M+H$^+$)=442.37

Example 9

(4aR*,8aS*)-8a-methyl-7-(7H-pyrrolo[2,3-d]pyrimidin-4-yl)-3,4,4a,5,6,8-hexahydro-1H-2,7-naphthyridine-2-sulfonamide (Compound 9)

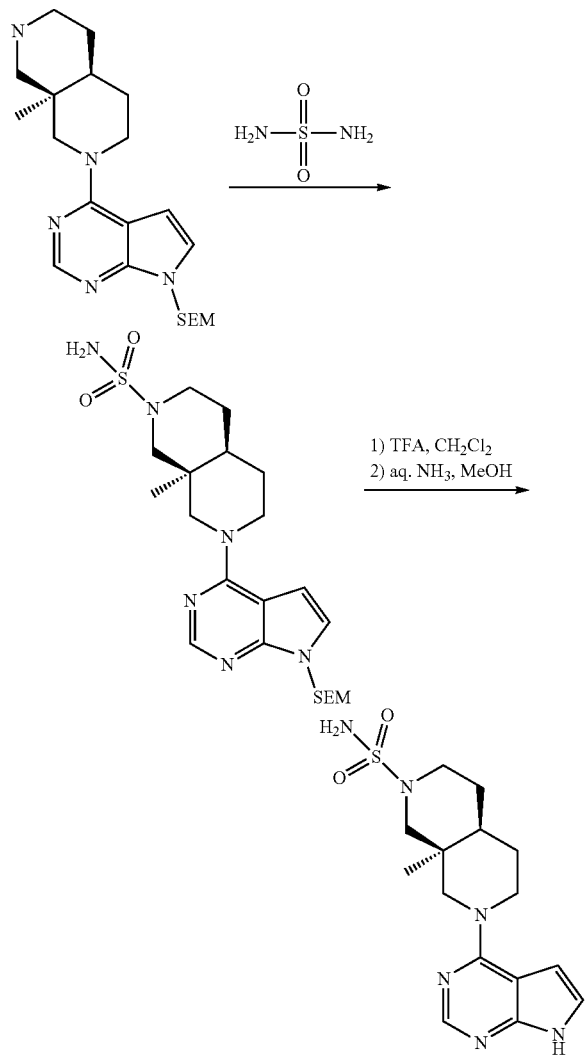

Intermediate 31 (50 mg, 0.125 mmol) is dissolved in dioxane (10 mL) and sulfamide (50 mg, 0.52 mmol) is added and the mixture is heated to reflux for 20 h. After cooling to rt the reaction mixture was concentrated and purified by prep HPLC (basic). The intermediate SEM-protected product is dissolved in DCM (3 mL) and TFA (3 mL) and stirred at rt for 1.5 h. The reaction mixture was concentrated under reduced pressure, redissolved in MeOH (3 mL) and then was added aq. NH$_3$ (3 mL). The mixture is stirred overnight and the purified by HPLC (basic).
UPLC-MS Method 5: $t_R$=1.67 (M+H$^+$)=351.44

Example 13

(4aR*,8aS*)-8a-methyl-2-methylsulfonyl-7-(7H-pyrrolo[2,3-d]pyrimidin-4-yl)-3,4,4a,5,6,8-hexahydro-1H-2,7-naphthyridine (Compound 13)

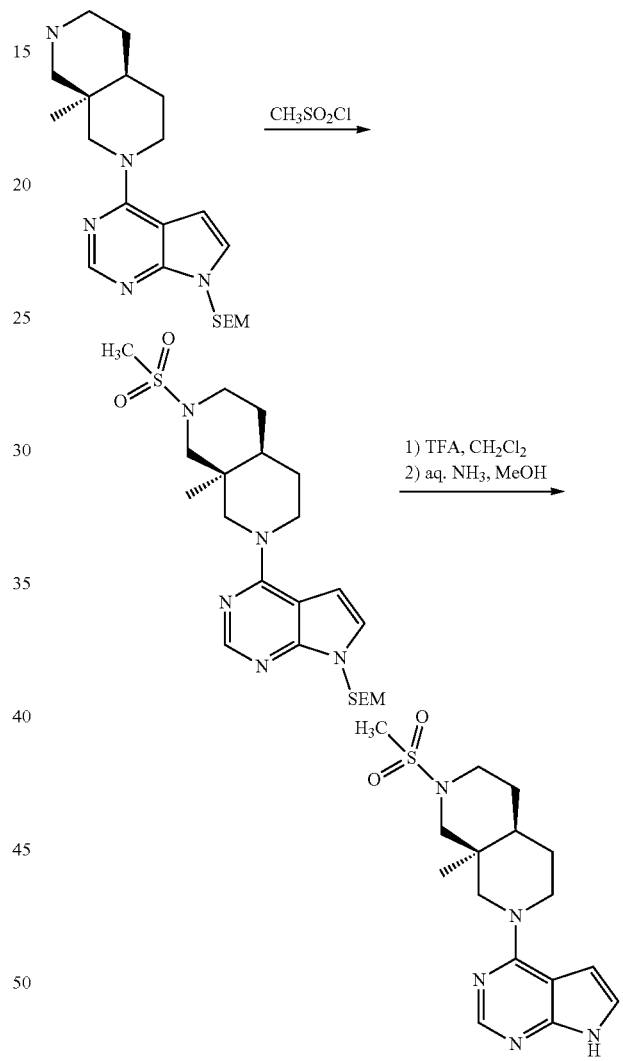

Intermediate 31 (50 mg, 0.125 mmol) is dissolved in dioxane (5 mL) and TEA (63 mg, 0.5 mmol) is added and the mixture is cooled to 0° C. followed by addition of CH$_3$SO$_2$Cl (22 mg, 0.187 mmol). After stirring at rt for 1.5 h the reaction mixture underwent aq. workup (3×10 mL DCM), concentrated under reduced pressure and purified by prep HPLC (basic). The intermediate SEM-protected product is dissolved in DCM (2 mL) and TFA (2 mL) and stirred at rt for 1.5 h. The reaction mixture was concentrated under reduced pressure, redissolved in MeOH (2 mL) and then was added aq. NH$_3$ (2 mL). The mixture is stirred overnight and the purified by HPLC (basic).
UPLC-MS Method 5: $t_R$=1.75 (M+H$^+$)=350.45

Example 15

1-[(4aR*,8aS*)-8a-ethyl-7-(7H-pyrrolo[2,3-d]pyrimidin-4-yl)-3,4,4a,5,6,8-hexahydro-1H-2,7-naphthyridin-2-yl]ethanone (Compound 15)

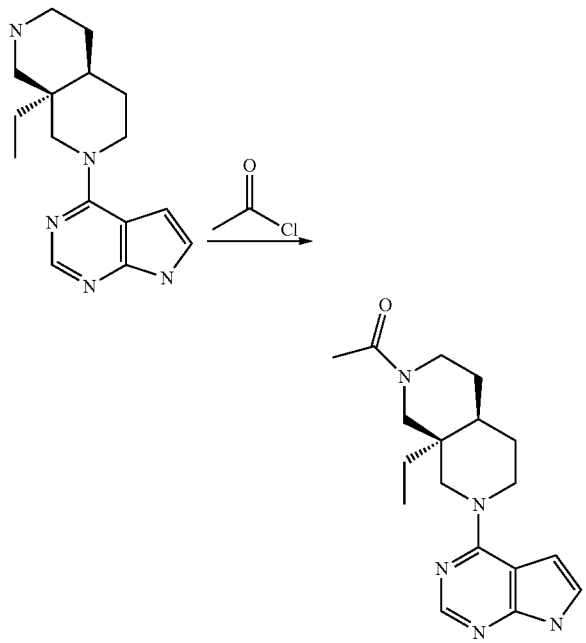

Intermediate 10 (5 mg, 0.01752 mmol) was suspended in MeCN (0.5 mL) and DIPEA (3.0 equiv., 0.0526 mmol, 6.8 mg, 0.00915 mL), cooled on ice and added acetyl chloride (1 equiv., 0.0175 mmol, 1.4 mg, 0.00132 mL). The reaction mixture was stirred on icebath for 30 min before the mixture was purified directly on preparative HPLC (basic) to provide example 15 as a white solid (racemic single diastereomer).

UPLC-MS Method 5: $t_R$=1.75 (M+H$^+$)=328.21

Example 16

(4aR*,8aS*)-8a-ethyl-7-(7H-pyrrolo[2,3-d]pyrimidin-4-yl)-3,4,4a,5,6,8-hexahydro-1H-2,7-naphthyridine-2-carbaldehyde (Compound 16)

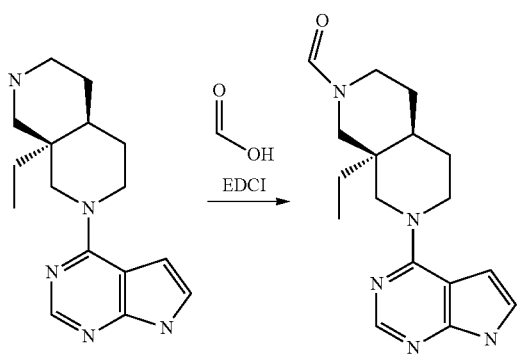 [SMILES: CC[C@]12CNCC[C@H]1CCN(c1ncnc3[nH]ccc13)C2 ; O=CO ; CC[C@]12CN(C=O)CC[C@H]1CCN(c1ncnc3[nH]ccc13)C2]

Intermediate 10 (5 mg, 0.0175 mmol) was dissolved in DMF (0.8 mL) and added formic acid (1.1 equiv., 0.887 mg, 0.0193 mmol), DMAP (1 equiv., 0.0175 mmol, 2.14 mg), and EDCI (1.2 equiv., 0.021 mmol, 4.0 mg) in a microwave reactor vial. The vial was sealed and stirred at rt for 2 h. The mixture was purified directly on preparative HPLC (basic) to provide example 16 as a white solid (racemic single diastereomer).

UPLC-MS Method 5: $t_R$=1.73 (M+H$^+$)=314.19

Example 17

(4aR*,8aS*)-8a-ethyl-7-(7H-pyrrolo[2,3-d]pyrimidin-4-yl)-3,4,4a,5,6,8-hexahydro-1H-2,7-naphthyridine-2-sulfonamide (Compound 17)

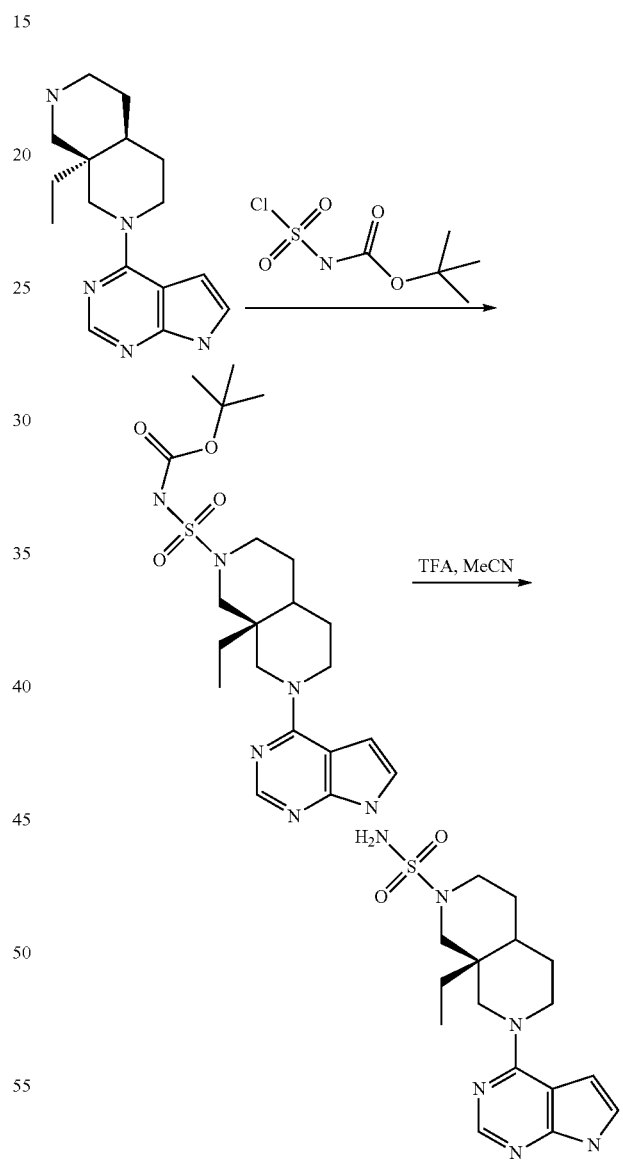

Boc-sulfamoyl chloride (1.1 equiv., 0.0771 mmol, 16.6 mg) was added to a solution of Intermediate 10 (20 mg, 0.0701 mmol) and TEA (5 equiv., 0.350 mmol, 35.5 mg, 0.0488 mL) in dry acetonitrile (0.50 mL). The reaction mixture was stirred at rt for 15 h, then TFA (20 equiv., 1.40 mmol, 160 mg, 0.107 mL) was added to the mixture and stirred for 3 h at rt and then heated at 60° C. for another 1 h for full conversion into the desired product.

The reaction mixture was evaporated to dryness and purified by preparative HPLC to provide example 17 (13.1 mg, 0.0359 mmol, 51% yield) as a white solid (racemic single diastereomer).

UPLC-MS: $t_R$=0.45 (M+H$^+$)=365.1

1H NMR (600 MHz, DMSO-d6) δ 11.65 (s, 1H), 8.11 (s, 1H), 7.16 (dd, J=3.6, 2.4 Hz, 1H), 6.65 (s, 2H), 6.54 (dd, J=3.6, 1.8 Hz, 1H), 4.19-4.00 (m, 2H), 3.62 (br s, 1H), 3.51 (d, J=13.5 Hz, 1H), 3.01 (m, 1H), 2.96-2.82 (m, 2H), 2.76 (d, J=12.0 Hz, 1H), 1.83 (td, J=8.7, 4.2 Hz, 1H), 1.78-1.56 (m, 5H), 1.44 (dq, J=14.8, 7.5 Hz, 1H), 0.83 (t, J=7.5 Hz, 3H).

The pure enantiomers were obtained by chiral SFC separation. The racemic material was dissolved to 77 mg/mL in ethanol and was then purified by SFC. Each injection was 0.2 mL (15 mg). The column used was a Lux A1 (21.2 mm×250 mm, 5 μm). The eluent was MeOH/CO$_2$ 25%. The flow rate was 21 mL/min at a wavelength of 220 nm. The wet fractions were then evaporated to near dryness using a rotary evaporator, transferred into the final vessel with DCM which was removed under a stream of nitrogen at 40° C. before being stored in a vacuum oven at 40° C. and 5 mbar for 6 h to afford off-white solids. The final analysis was performed by SFC using a Lux A2 (4.6 mm×250 mm, 5 μm). The flow rate was 1 mL/min and wavelength 254 nm.

Thus were obtained Example 18 and Example 19.

Example 18

(4aR,8aS)-8a-ethyl-7-(7H-pyrrolo[2,3-d]pyrimidin-4-yl)-3,4,4a,5,6,8-hexahydro-1H-2,7-naphthyridine-2-sulfonamide (Compound 18)

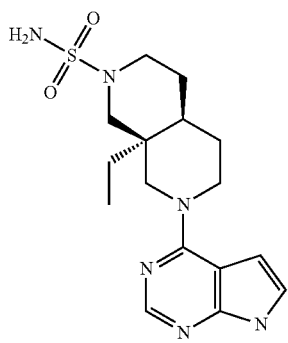 [SMILES: CC[C@@]12CN(c3ncnc4[nH]ccc34)CC[C@@H]1CCN(S(N)(=O)=O)C2]

85 mg, 99.9% ee, anal SFC $t_R$=7.38 min
UPLC-MS Method 5: $t_R$=1.78 (M+H$^+$)=365.17

1H NMR (600 MHz, DMSO-d6) δ 11.65 (s, 1H), 8.11 (s, 1H), 7.16 (dd, J=3.6, 2.4 Hz, 1H), 6.65 (s, 2H), 6.54 (dd, J=3.6, 1.8 Hz, 1H), 4.19-4.00 (m, 2H), 3.62 (br s, 1H), 3.51 (d, J=13.5 Hz, 1H), 3.01 (m, 1H), 2.96-2.82 (m, 2H), 2.76 (d, J=12.0 Hz, 1H), 1.83 (td, J=8.7, 4.2 Hz, 1H), 1.78-1.56 (m, 5H), 1.44 (dq, J=14.8, 7.5 Hz, 1H), 0.83 (t, J=7.5 Hz, 3H).

A crystalline form was characterized by m.p. (DSC onset temperature) 207.9±2° C.

Example 19

(4aS,8aR)-8a-ethyl-7-(7H-pyrrolo[2,3-d]pyrimidin-4-yl)-3,4,4a,5,6,8-hexahydro-1H-2,7-naphthyridine-2-sulfonamide (Compound 19)

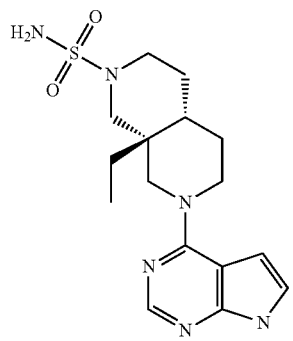 [SMILES: CC[C@]12CN(c3ncnc4[nH]ccc34)CC[C@H]1CCN(S(N)(=O)=O)C2]

95 mg, 97.7% ee, anal SFC $t_R$=9.34 min
UPLC-MS Method 5: $t_R$=1.77 (M+H$^+$)=365.17

1H NMR (600 MHz, DMSO-d6) δ 11.65 (s, 1H), 8.11 (s, 1H), 7.16 (dd, J=3.6, 2.4 Hz, 1H), 6.65 (s, 2H), 6.54 (dd, J=3.6, 1.8 Hz, 1H), 4.19-4.00 (m, 2H), 3.62 (br s, 1H), 3.51 (d, J=13.5 Hz, 1H), 3.01 (m, 1H), 2.96-2.82 (m, 2H), 2.76 (d, J=12.0 Hz, 1H), 1.83 (td, J=8.7, 4.2 Hz, 1H), 1.78-1.56 (m, 5H), 1.44 (dq, J=14.8, 7.5 Hz, 1H), 0.83 (t, J=7.5 Hz, 3H).

Example 20

2-[(4aR*,8aS*)-8a-ethyl-7-(7H-pyrrolo[2,3-d]pyrimidin-4-yl)-3,4,4a,5,6,8-hexahydro-1H-2,7-naphthyridin-2-yl]-5-bromo-1,3,4-thiadiazole (Compound 20)

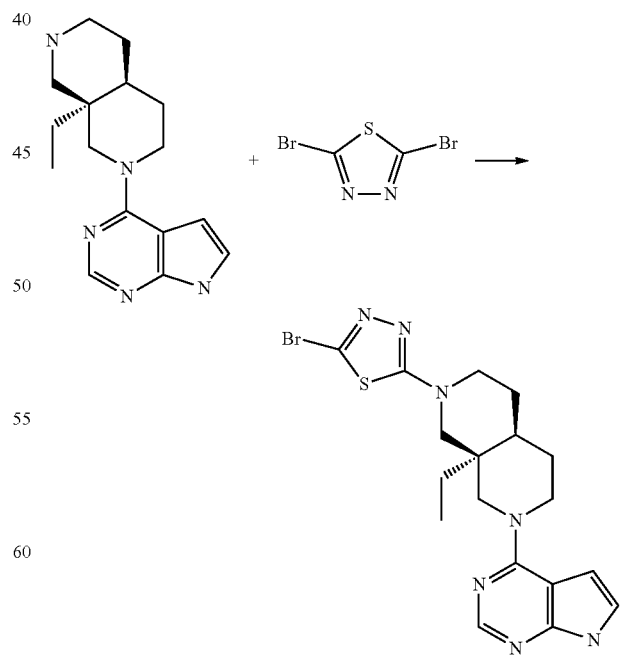

Intermediate 10 (5 mg, 0.01752 mmol) was suspended in MeCN (0.5 mL) and added DIPEA (3.0 equiv., 0.0526 mmol, 6.8 mg, 0.00915 mL) and 2,5-dibromo-1,3,4-thiadiazole (1 equiv., 0.0175 mmol, 4.27 mg) in a microwave reactor vial. The vial was sealed and heated to 60° C. for 2.5 h in a heating block. The reaction mixture was purified by preparative HPLC (basic). The pure fraction was evaporated to dryness to provide the desired compound as a white solid (racemic single diastereomer).

UPLC-MS: $t_R$=0.64 (M+H$^+$)=448/450

Example 23

(4aR*,8aS*)-8a-ethyl-7-(7H-pyrrolo[2,3-d]pyrimidin-4-yl)-3,4,4a,5,6,8-hexahydro-1H-2,7-naphthyridine-2-carbonitrile (Compound 23)

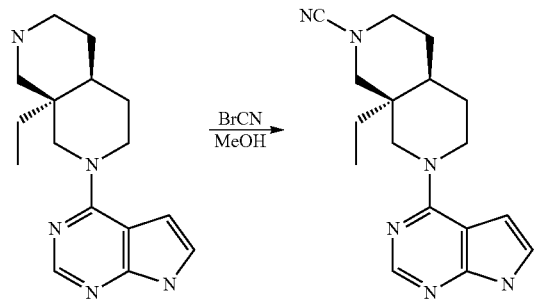

Cyanogen bromide (1.1 equiv., 2.66 mmol, 282 mg) was added portionwise to a cold (0° C.) solution of Intermediate 10 (690 mg, 2.42 mmol, 1.0 equiv.) and sodium bicarbonate (2.0 equiv., 4.84 mmol, 406 mg) in MeOH (12) and the solution was stirred under argon at rt for 1 h for full conversion of the starting amine into the desired product. Evaporated directly onto celite and purified by automated column chromatography (ISCO, gradient: DCM->10% MeOH) to afford Example 23 (652 mg, 2.10 mmol, 87% yield) as a white solid (racemic single diastereomer).

UPLC-MS: $t_R$=0.51 (M+H$^+$)=311.3

1H NMR (600 MHz, DMSO-d6) δ 11.67 (s, 1H), 8.11 (s, 1H), 7.17 (dd, J=3.6, 2.2 Hz, 1H), 6.60 (dd, J=3.6, 1.7 Hz, 1H), 4.17-3.98 (m, 2H), 3.72-3.47 (m, 2H), 3.31-3.25 (m, 1H), 3.16 (d, J=12.9 Hz, 1H), 3.06 (ddd, J=12.5, 6.3, 4.4 Hz, 1H), 2.90 (d, J=13.0 Hz, 1H), 1.85-1.44 (m, 7H), 0.83 (t, J=7.6 Hz, 3H).

The pure enantiomers were obtained by chiral SFC separation. The racemic material was dissolved to 40 mg/mL in methanol and was then purified by SFC. Each injection was 0.22 mL (8 mg). The column used was a Amy-C (20 mm×250 mm, 5 μm). The eluent was MeOH/CO$_2$ 25%. The flow rate was 21 mL/min at a wavelength of 220 nm. The wet fractions were then evaporated to near dryness using a rotary evaporator, transferred into the final vessel with DCM which was removed under a stream of nitrogen at 40° C. before being stored in a vacuum oven at 40° C. and 5 mbar for 6 h to afford off-white solids. The final analysis was performed by SFC using a Amy-C (4.6 mm×250 mm, 5 μm). The flow rate was 1 mL/min and wavelength 254 nm.

Thus were obtained Example 21 and Example 22.

Example 21

(4aS,8aR)-8a-ethyl-7-(7H-pyrrolo[2,3-d]pyrimidin-4-yl)-3,4,4a,5,6,8-hexahydro-1H-2,7-naphthyridine-2-carbonitrile (Compound 21)

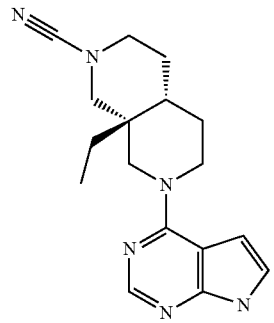 [SMILES: CC[C@@]12CN(C#N)CC[C@@H]1CCN(c1ncnc3[nH]ccc13)C2]

160 mg, 98.8% ee, anal SFC $t_R$=10.63 min
UPLC-MS Method 5: $t_R$=1.85 (M+H$^+$)=311.19
1H NMR (600 MHz, DMSO-d6) δ 11.67 (s, 1H), 8.11 (s, 1H), 7.17 (dd, J=3.6, 2.2 Hz, 1H), 6.60 (dd, J=3.6, 1.7 Hz, 1H), 4.17-3.98 (m, 2H), 3.72-3.47 (m, 2H), 3.31-3.25 (m, 1H), 3.16 (d, J=12.9 Hz, 1H), 3.06 (ddd, J=12.5, 6.3, 4.4 Hz, 1H), 2.90 (d, J=13.0 Hz, 1H), 1.85-1.44 (m, 7H), 0.83 (t, J=7.6 Hz, 3H).

Example 22

(4aR,8aS)-8a-ethyl-7-(7H-pyrrolo[2,3-d]pyrimidin-4-yl)-3,4,4a,5,6,8-hexahydro-1H-2,7-naphthyridine-2-carbonitrile (Compound 22)

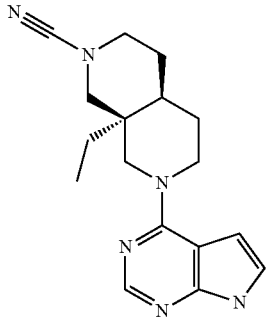 [SMILES: CC[C@]12CN(C#N)CC[C@H]1CCN(c1ncnc3[nH]ccc13)C2]

124 mg, 98.7% ee, anal SFC $t_R$=8.93 min
UPLC-MS Method 5: $t_R$=1.85 (M+H$^+$)=311.19
1H NMR (600 MHz, DMSO-d6) δ11.67 (s, 1H), 8.11 (s, 1H), 7.17 (dd, J=3.6, 2.2 Hz, 1H), 6.60 (dd, J=3.6, 1.7 Hz, 1H), 4.17-3.98 (m, 2H), 3.72-3.47 (m, 2H), 3.31-3.25 (m, 1H), 3.16 (d, J=12.9 Hz, 1H), 3.06 (ddd, J=12.5, 6.3, 4.4 Hz, 1H), 2.90 (d, J=13.0 Hz, 1H), 1.85-1.44 (m, 7H), 0.83 (t, J=7.6 Hz, 3H).

Single X-Ray Crystallography of Compound 22

A representative crystal was obtained by crystallization of compound 22 in EtOAc:Heptane (2:1) solution by slowly evaporation.

The crystal was characterized by having single crystal parameters which are substantially the same as those provided in Table A. Compound 22 has a structure obtained by single crystal X-Ray crystallography (XRC) as shown in FIG. 1.

TABLE A

The crystal parameters from the single crystal structure determination

| Sample | CB2016-7896 |
|---|---|
| Crystal data | |
| Chemical formula | $C_{17}H_{22}N_6$ |
| $M_r$ | 310.40 |
| Crystal system, space group | Monoclinic, $P2_1$ |
| Temperature (K) | 120 |
| a, b, c (Å) | 14.2724 (5), 8.1638 (2), 14.4319 (5) |
| β (°) | 109.110 (4) |
| V (Å$^3$) | 1588.90 (10) |
| Z | 4 |
| $D_x$ (Mg m$^{-3}$) | 1.298 |
| Radiation type | Cu Kα |
| μ (mm$^{-1}$) | 0.65 |
| Crystal shape | Needle |
| Colour | Clear colourless |
| Crystal size (mm) | 0.36 × 0.08 × 0.05 |
| Data collection | |
| Diffractometer | SuperNova, Dual, Cu at zero, Atlas |
| Radiation source | sealed X-ray tube, SuperNova (Cu) X-ray Source |
| Scan method | ω scans |
| Absorption correction | Multi-scan CrysAlis PRO, Agilent Technologies, Version 1.171.37.34 (release 22-05-2014 CrysAlis171 .NET) (compiled May 22, 2014, 16:03:01) Empirical absorption correction using spherical harmonics, implemented in SCALE3 ABSPACK scaling algorithm. |
| $T_{min}$, $T_{max}$ | 0.538, 1.000 |
| No. of measured, independent and observed [I > 2σ(I)] reflections | 10966, 4756, 4120 |
| $R_{int}$ | 0.052 |
| $θ_{max}$ (°) | 62.1 |
| (sin θ/λ)$_{max}$ (Å$^{-1}$) | 0.573 |
| Refinement | |
| R[F$^2$ > 2σ(F$^2$)], wR(F$^2$), S | 0.048, 0.141, 0.94 |
| No. of reflections | 4756 |
| No. of parameters | 417 |
| No. of restraints | 1 |
| H-atom treatment | H-atom parameters constrained |
| Δ⟩$_{max}$, Δ⟩$_{min}$ (e Å$^{-3}$) | 0.25, -0.19 |
| Absolute structure | Flack x determined using 1560 quotients [(I+) − (I−)]/[(I+) + (I−)] (Parsons and Flack (2004), Acta Cryst. A60, s61). |
| Absolute structure parameter | -0.1 (4) |

The above crystalline form was characterized by m.p. (DSC onset temperature) 178.4±2° C.

Example 25

2-[(4aR*,8aS*)-8a-ethyl-7-(7H-pyrrolo[2,3-d]pyrimidin-4-yl)-3,4,4a,5,6,8-hexahydro-1H-2,7-naphthyridin-2-yl]thiazole-4-carbonitrile (Compound 25)

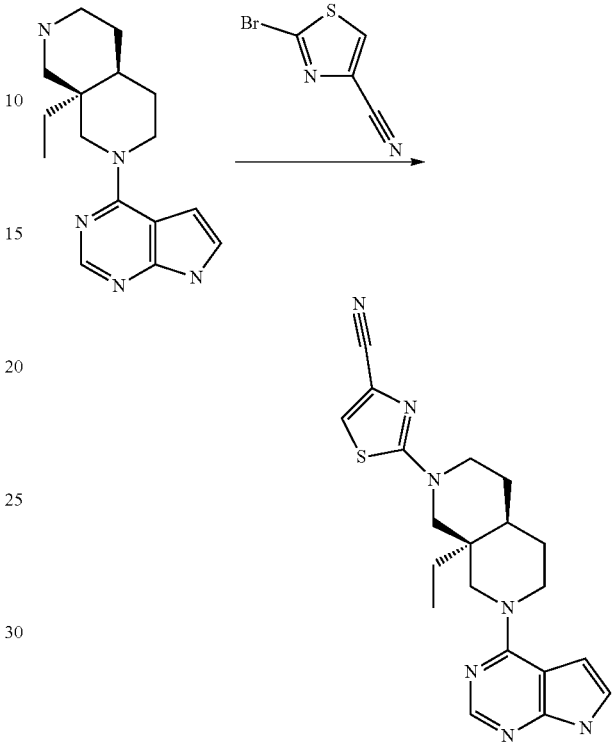

Intermediate 10 (50 mg, 0.175 mmol), 2-bromothiazole-4-carbonitrile (33 mg, 0.175 mmol), and DIPEA (68 mg, 0.0915 mL, 0.526 mmol) was dissolved in MeCN (1 mL) in a microwave reactor vial and heated at 60° C. for 15 h for full conversion into the desired product. The mixture was then purified directly by preparative HPLC to provide example 25 (36 mg, 0.0915 mmol, 52% yield) as a white solid (racemic single diastereomer).

UPLC-MS Method 5: $t_R$=2.15 (M+H$^+$)=394.17

Example 26

4-[(3aS*,7aS*)-3a-methyl-2-methylsulfonyl-1,3,4,6,7,7a-hexahydropyrrolo[3,4-c]pyridin-5-yl]-7H-pyrrolo[2,3-d]pyrimidine (Compound 26)

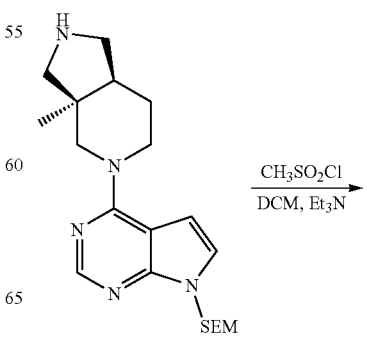

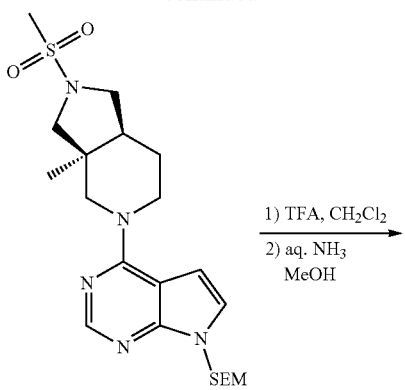

1) TFA, CH₂Cl₂
2) aq. NH₃ MeOH

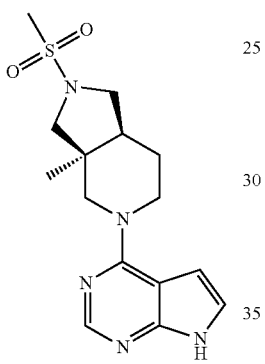

Step 1:

To a solution of intermediate 23 (64 mg, 0.165 mmol) in DCM (5 mL) was added triethylamine (140 mg) and CH₃SO₂Cl (58 mg, 0.51 mmol) and the mixture was stirred at rt for 30 min. After aqueous work up (H₂O, DCM) the organic layer was dried (MgSO₄) and concentrated. The residue was purified by chromatography to give 81 mg solid which was used directly.

Step 2:

The product of Step 1 (81 mg) was dissolved in DCM (2 mL) and TFA (2 mL) and the solution was stirred for 3 h. The mixture was evaporated to dryness and the residue was dissolved in MeOH (2 mL) and NH₃.H₂O (2 mL) and stirred overnight. The resulting mixture was evaporated to dryness, taken up in ethylacetate and purified by column chromatography followed by recrystallization from water to give Example 26 (9.3 mg, white solid, 16% yield).

UPLC-MS Method 5: $t_R$=1.68 (M+H⁺)=336.14

¹H NMR (300 MHz, Chloroform-d) δ 8.01 (s, 1H), 7.02 (d, J=3.6 Hz, 1H), 6.55 (d, J=3.6 Hz, 1H), 4.07-3.91 (m, 2H), 3.73-3.62 (m, 2H), 3.64 (m, 1H), 3.17-3.06 (m, 4H), 2.93 (m, 1H), 2.05 (m, 1H), 1.86 (m, 1H), 1.65 (m, 1H).

Example 27

(3aS*,7aS*)-3a-methyl-5-(7H-pyrrolo[2,3-d]pyrimidin-4-yl)-1,3,4,6,7,7a-hexahydropyrrolo[3,4-c]pyridine-2-sulfonamide (Compound 27)

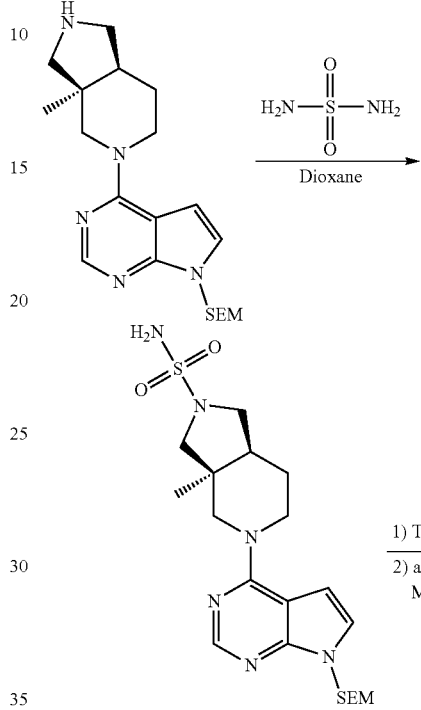

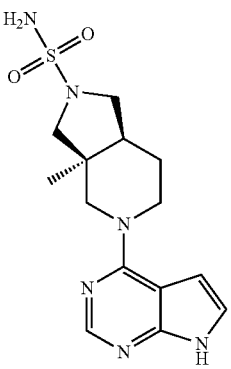

Step 1:

To a solution of intermediate 23 (90 mg, 0.23 mmol) in dioxane (2 mL) was added sulfamide (30 mg, 0.31 mmol) and the mixture was heated to 110° C. for 2 h, followed by evaporation of the solvent. The residue was purified by chromatography (DCM:MeOH 10:1) to give 60 mg as an oil which was used directly.

Step 2:

The product of Step 1 (60 mg) was dissolved in DCM (3 mL) and TFA (3 mL) and the solution was stirred for 3 h. The mixture was evaporated to dryness and the residue was dissolved in MeOH (3 mL) and NH₃.H₂O (3 mL) and stirred overnight. The resulting mixture was evaporated to dryness, taken up in ethylacetate and purified by column chromatography (EA:MeOH 20:1) to give Example 27 (8 mg, white solid, 23% yield).

UPLC-MS Method 5: $t_R$=1.6 (M+H⁺)=337.14

¹H NMR (300 MHz, Chloroform-d) δ 8.01 (s, 1H), 7.02 (d, J=3.6 Hz, 1H), 6.55 (d, J=3.6 Hz, 1H), 4.07-3.91 (m, 2H), 3.73-3.62 (m, 2H), 3.64 (m, 1H), 3.17-3.06 (m, 4H), 2.93 (m, 1H), 2.05 (m, 1H), 1.86 (m, 1H), 1.65 (m, 1H).

Example 28

(3aR,7aR)-3a-methyl-5-(7H-pyrrolo[2,3-d]pyrimidin-4-yl)-1,3,4,6,7,7a-hexahydropyrrolo[3,4-c]pyridine-2-carbonitrile (Compound 28)

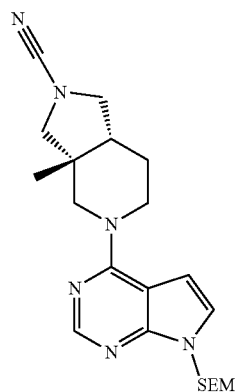

A solution of intermediate 30 (240 mg, 0.582 mmol) in 1.0 M TBAF in THF (5.0 mL, 5.0 mmol) was evaporated to remove THF and the residue was stirred at 60° C. under vacuum (30-40 mbar) for 35 min. The reaction mixture was purified by chromatography using a Grace system (40 g silica gel column, gradient elution, EtOAc:MeOH 100:0→90:10) to remove most of the TBAF. Final purification by prep. HPLC (basic) afforded Example 28 (28 mg, 17% yield) as a white solid.

UPLC-MS: t_R=0.42 (M+H⁺)=283.2

¹H NMR (300 MHz, DMSO-d₆) δ 11.61 (br s, 1H), 8.12 (s, 1H), 7.18 (d, J=3.6 Hz, 1H), 6.61 (d, J=3.6 Hz, 1H), 4.00-3.70 (m, 4H), 3.63 (dd, J=9.4, 7.2 Hz, 1H), 3.36 (dd, J=9.4, 5.7 Hz, 1H), 3.27 (d, J=9.3 Hz, 1H), 3.13 (d, J=9.3 Hz, 1H), 2.15-2.03 (m, 1H), 1.90-1.76 (m, 1H), 1.60-1.44 (m, 1H), 1.05 (s, 3H).

Example 29

(3aS,7aS)-3a-methyl-5-(7H-pyrrolo[2,3-d]pyrimidin-4-yl)-1,3,4,6,7,7a-hexahydropyrrolo[3,4-c]pyridine-2-carbonitrile (Compound 29)

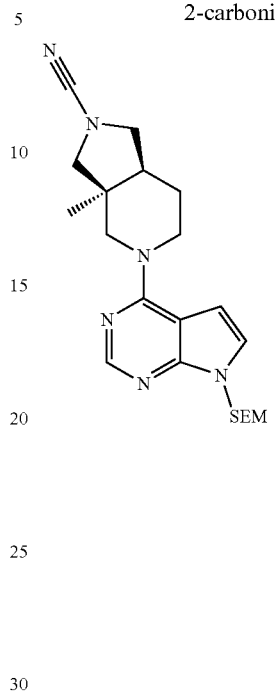

Prepared as example 28 but starting from intermediate 29 (220 mg, 0.533 mmol). Yield: 17.6 mg, 12%.

UPLC-MS: t_R=0.42 (M+H⁺)=283.2

¹H NMR (300 MHz, DMSO-d₆) δ 11.66 (br s, 1H), 8.12 (s, 1H), 7.17 (dd, J=3.6, 2.1 Hz, 1H), 6.61 (dd, J=3.6, 1.5 Hz, 1H), 4.00-3.70 (m, 4H), 3.63 (dd, J=9.4, 7.2 Hz, 1H), 3.36 (dd, J=9.4, 5.7 Hz, 1H), 3.27 (d, J=9.3 Hz, 1H), 3.13 (d, J=9.3 Hz, 1H), 2.15-2.03 (m, 1H), 1.90-1.76 (m, 1H), 1.60-1.44 (m, 1H), 1.05 (s, 3H).

Example 30

(3aS*,7aS*)—N-(cyanomethyl)-3a-methyl-5-(7H-pyrrolo[2,3-d]pyrimidin-4-yl)-1,3,4,6,7,7a-hexahydropyrrolo[3,4-c]pyridine-2-sulfonamide (Compound 30)

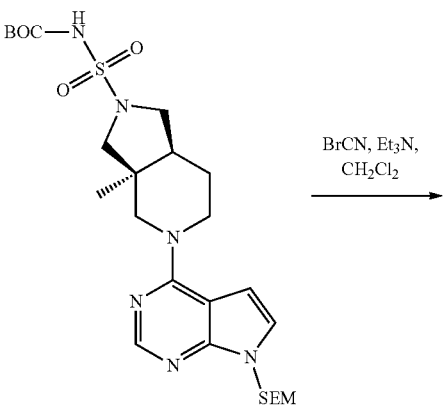

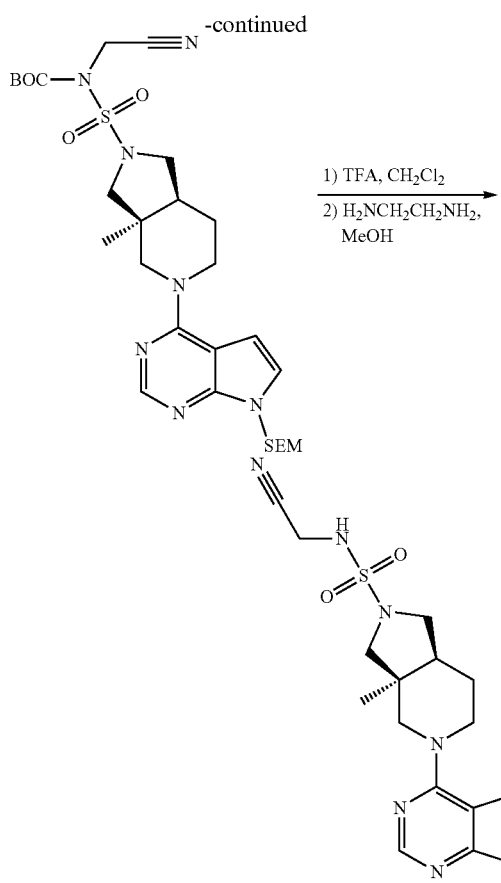

1) TFA, CH$_2$Cl$_2$
2) H$_2$NCH$_2$CH$_2$NH$_2$, MeOH

Step 1:

To a solution of intermediate 22 (16 mg, 0.028 mmol) in DCM (1 mL) was added triethylamine (12 μL, 0.085 mmol) followed by cyanogen bromide (5.1 mg, 0.042 mmol). The mixture was shaken for 2 h at rt after which additional triethylamine (24 μL, 0.17 mmol) and cyanogen bromide (10 mg, 0.085 mmol) were added. The mixture was shaken overnight at rt and intermediate product (5 mg, 29% yield) was obtained by prep HPLC (acidic).

UPLC-MS: $t_R$=0.97 (M+H$^+$)=606.4

$^1$H NMR (600 MHz, Chloroform-d) δ 8.33 (s, 1H), 7.10 (d, J=3.7 Hz, 1H), 6.49 (d, J=3.7 Hz, 1H), 5.58 (s, 2H), 4.56 (s, 2H), 4.17-4.13 (m, 1H), 4.12 (d, J=13.8 Hz, 1H), 3.84 (dd, J=9.7, 6.9 Hz, 1H), 3.71-3.65 (m, 1H), 3.60 (d, J=13.9 Hz, 1H), 3.56-3.52 (m, 2H), 3.52-3.48 (m, 2H), 3.30 (d, J=9.6 Hz, 1H), 2.18-2.12 (m, 1H), 1.98-1.91 (m, 1H), 1.72-1.64 (m, 1H), 1.49 (s, 9H), 1.17 (s, 3H), 0.94-0.88 (m, 2H), −0.05 (s, 9H).

Step 2:

The product of Step 1 (5 mg, 0.008 mmol) was dissolved in DCM (0.6 mL) and TFA (0.2 mL) and the solution was shaken at rt overnight. The mixture was evaporated to dryness and the residue was dissolved in MeCN (0.5 mL) and ethylenediamine (0.1 mL). The resulting mixture was shaken at rt for 3.5 h, volatiles were evaporated and the residue was purified using prep HPLC (acidic) to afford Example 30 (2.6 mg, 84% yield).

UPLC-MS: $t_R$=0.42 (M+H$^+$)=376.3

$^1$H NMR (600 MHz, DMSO-d$_6$) δ 11.68 (br s, 1H), 8.16 (s, 1H), 8.11 (s, 1H), 7.17 (d, J=3.5 Hz, 1H), 6.61 (d, J=3.6 Hz, 1H), 4.08 (s, 2H), 4.03-3.97 (m, 1H), 3.96 (d, J=13.7 Hz, 1H), 3.75-3.68 (m, 2H), 3.50 (dd, J=9.8, 7.2 Hz, 1H), 3.19 (dd, J=9.8, 5.2 Hz, 1H), 3.15 (d, J=9.5 Hz, 1H), 2.99 (d, J=9.5 Hz, 1H), 2.15-2.09 (m, 1H), 1.86-1.79 (m, 1H), 1.61-1.53 (m, 1H), 1.08 (s, 3H).

Example 31

4-[(3aS*,7aS*)-3a-methyl-2-(2,2,2-trifluoroethylsulfonyl)-1,3,4,6,7,7a-hexahydropyrrolo[3,4-c]pyridin-5-yl]-7H-pyrrolo[2,3-d]pyrimidine (Compound 31)

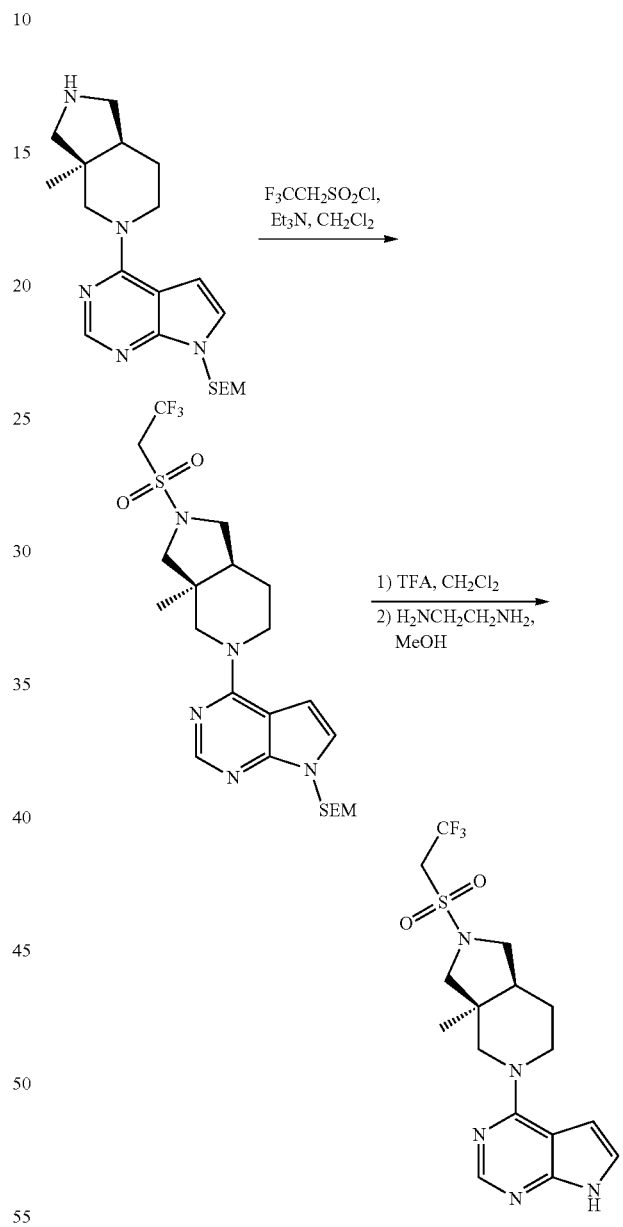

Step 1:

To a solution of intermediate 23 (20 mg, 0.052 mmol) in DCM (0.6 mL) was added triethylamine (22 μL, 0.15 mmol) followed by 2,2,2-trifluoroethanesulfonyl chloride (14 mg, 0.077 mmol) and the mixture was shaken at rt for 45 min. Volatiles were evaporated and the residue was purified using prep HPLC (acidic) to afford intermediate product (10 mg, 36% yield).

UPLC-MS: $t_R$=0.91 (M+H$^+$)=534.3

$^1$H NMR (600 MHz, Chloroform-d) δ 8.34 (s, 1H), 7.11 (d, J=3.8 Hz, 1H), 6.50 (d, J=3.8 Hz, 1H), 5.58 (s, 2H), 4.15-4.11 (m, 1H), 4.10 (d, J=13.9 Hz, 1H), 3.77-3.68 (m, 4H), 3.64 (d, J=13.8 Hz, 1H), 3.56-3.52 (m, 2H), 3.44-3.40 (m, 2H), 3.20 (d, J=9.6 Hz, 1H), 2.19-2.13 (m, 1H), 1.99-1.92 (m, 1H), 1.72-1.63 (m, 1H), 1.19 (s, 3H), 0.94-0.88 (m, 2H), −0.05 (s, 9H).

Step 2:

The product of Step 1 (10 mg, 0.019 mmol) was dissolved in DCM (0.6 mL) and TFA (0.2 mL) and the solution was shaken at rt overnight. The mixture was evaporated to dryness and the residue was dissolved in MeCN (0.5 mL) and ethylenediamine (0.1 mL). The resulting mixture was shaken at rt for 5 h, volatiles were evaporated and the residue was purified using prep. HPLC (acidic) to afford Example 31 (2.2 mg, 29% yield).

UPLC-MS: $t_R$=0.33 (M+H$^+$)=404.3

$^1$H NMR (600 MHz, DMSO-d$_6$) δ 11.67 (br s, 1H), 8.10 (s, 1H), 7.16 (d, J=3.5 Hz, 1H), 6.61 (d, J=3.6 Hz, 1H), 4.01-3.90 (m, 2H), 3.81-3.67 (m, 2H), 3.55-3.40 (m, 3H), 3.30-3.12 (m, 2H), 3.06-2.97 (m, 1H), 2.15-2.05 (m, 1H), 1.84-1.77 (m, 1H), 1.63-1.54 (m, 1H), 1.06 (s, 3H).

Example 32

3-[(3aS*,7aS*)-3a-methyl-5-(7H-pyrrolo[2,3-d]pyrimidin-4-yl)-1,3,4,6,7,7a-hexahydropyrrolo[3,4-c]pyridin-2-yl]-3-oxo-propanenitrile (Compound 32)

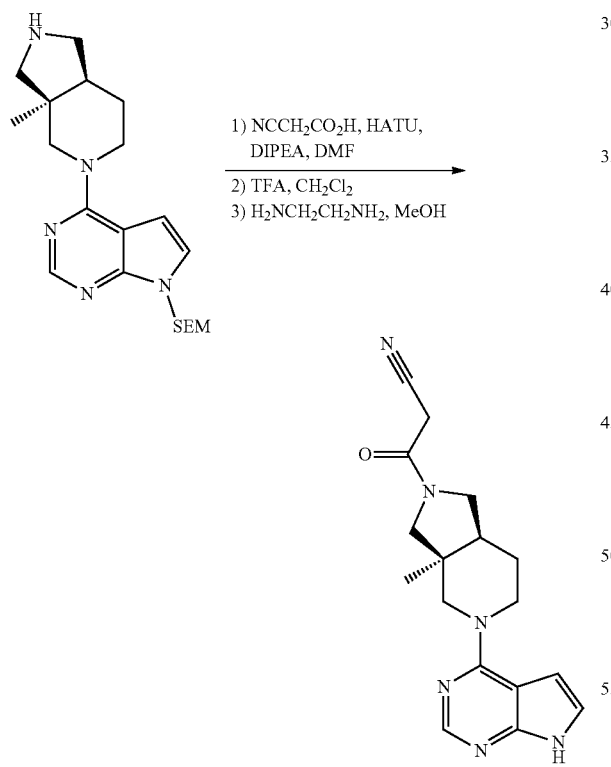

Prepared as Example 46 but starting from cyanoacetic acid (6.6 mg, 0.077 mmol). Yield: 1.2 mg, 7%. The $^1$H NMR spectrum shows two sets of peaks in a ca. 1:1 ratio corresponding to two amide bond rotamers.

UPLC-MS: $t_R$=0.38 (M+H$^+$)=325.3

$^1$H NMR (600 MHz, DMSO-d$_6$) δ 11.69 (br s, 1H), 8.11 (s, 1H), 7.17 (dd, J=3.7, 1.1 Hz, 1H), 6.61 (d, J=3.6 Hz, 0.5H), 6.58 (d, J=3.6 Hz, 0.5H), 4.04-3.97 (m, 1H), 3.96-3.84 (m, 3H), 3.76-3.67 (m, 1H), 3.66-3.61 (m, 1.5H), 3.55 (dd, J=12.0, 7.2 Hz, 0.5H), 3.41-3.30 (m, 1.5H), 3.22 (d, J=11.8 Hz, 0.5H), 3.16 (d, J=10.0 Hz, 0.5H), 3.05 (d, J=11.9 Hz, 0.5H), 2.18-2.11 (m, 0.5H), 2.08-2.02 (m, 0.5H), 1.85-1.76 (m, 1H), 1.52-1.43 (m, 1H), 1.06 (s, 1.5H), 1.04 (s, 1.5H).

Example 33

6-[(3aS,7aS)-3a-methyl-5-(7H-pyrrolo[2,3-d]pyrimidin-4-yl)-1,3,4,6,7,7a-hexahydropyrrolo[3,4-c]pyridin-2-yl]pyridine-3-carbonitrile (Compound 33)

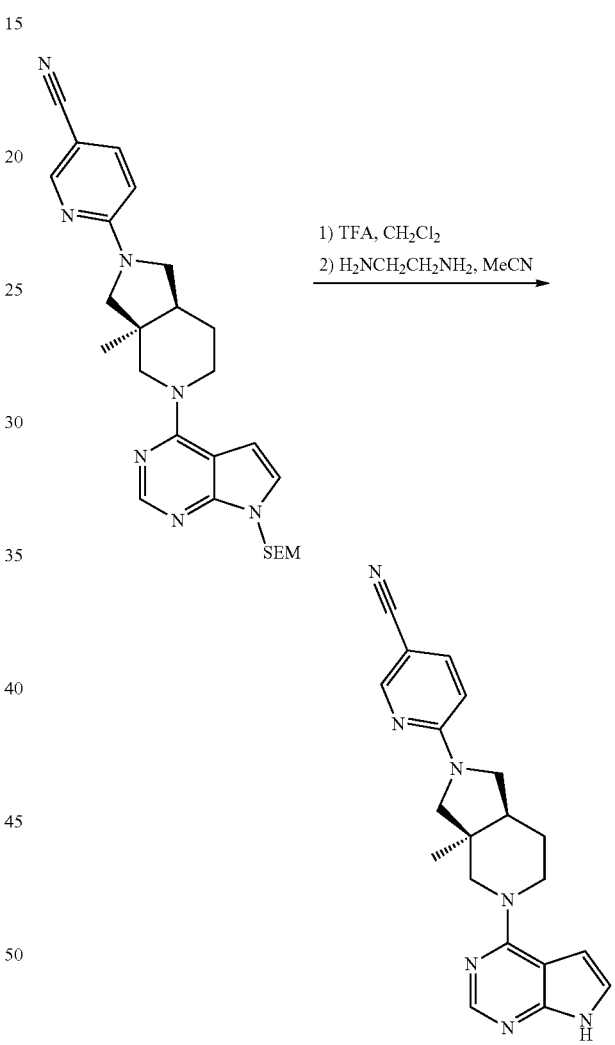

To a solution of intermediate 24 (111 mg, 0.227 mmol) in DCM (4 mL) was added TFA (0.3 mL) and the mixture was shaken at rt overnight. Volatiles were evaporated, the residue was dissolved in MeCN (2 mL) and ethylenediamine (0.15 mL, 2.3 mmol) was added. The mixture was stirred at rt for 3.5 h, volatiles were evaporated, and the residue was purified by prep. HPLC (acidic) to afford Example 33 (38 mg, 47% yield).

UPLC-MS: $t_R$=0.56 (M+H$^+$)=360.3

$^1$H NMR (600 MHz, DMSO-d$_6$) δ 11.68 (br s, 1H), 8.42 (br s, 1H), 8.12 (s, 1H), 7.78 (br d, J=8.8 Hz, 1H), 7.17 (dd, J=3.6, 2.3 Hz, 1H), 6.62 (d, J=3.4 Hz, 1H), 6.51 (br s, 1H), 4.14-3.89 (m, 2H), 3.85-3.57 (m, 3H), 3.51-3.12 (m, 3H), 2.33-2.15 (m, 1H), 1.92-1.84 (m, 1H), 1.55-1.46 (m, 1H), 1.11 (s, 3H).

Example 34

6-[(3aR,7aR)-3a-methyl-5-(7H-pyrrolo[2,3-d]pyrimidin-4-yl)-1,3,4,6,7,7a-hexahydropyrrolo[3,4-c]pyridin-2-yl]pyridine-3-carbonitrile (Compound 34)

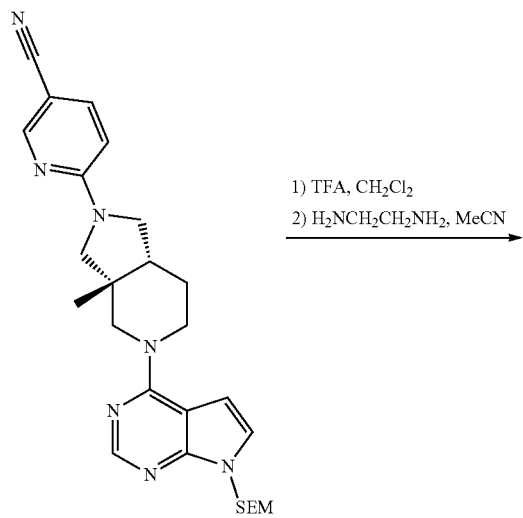

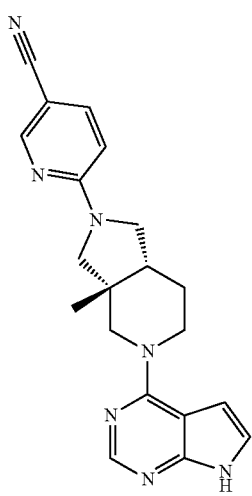

Prepared as Example 33 but starting from intermediate 25 (111 mg, 0.227 mmol). Yield: 36 mg, 44%.

UPLC-MS: $t_R$=0.57 (M+H$^+$)=360.3

$^1$H NMR (600 MHz, DMSO-d$_6$) δ 11.68 (br s, 1H), 8.42 (br s, 1H), 8.12 (s, 1H), 7.78 (br d, J=8.9 Hz, 1H), 7.17 (dd, J=3.6, 2.2 Hz, 1H), 6.62 (dd, J=3.7, 1.6 Hz, 1H), 6.51 (br s, 1H), 4.13-3.88 (m, 2H), 3.85-3.58 (m, 3H), 3.51-3.11 (m, 3H), 2.31-2.15 (m, 1H), 1.92-1.83 (m, 1H), 1.54-1.46 (m, 1H), 1.11 (s, 3H).

Example 35

4-[(3aS*,7aS*)-3a-methyl-2-(5-methylsulfonyl-2-pyridyl)-1,3,4,6,7,7a-hexahydropyrrolo[3,4-c]pyridin-5-yl]-7H-pyrrolo[2,3-d]pyrimidine (Compound 35)

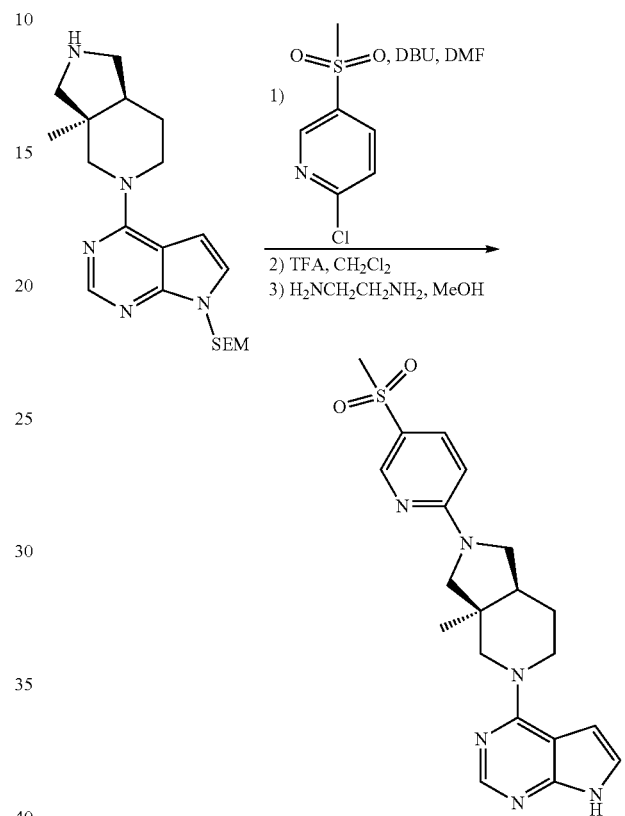

To a solution of intermediate 23 (50 mg, 0.13 mmol) in DMF (2 mL) was added 2-chloro-5-methylsulfonyl-pyridine (30 mg, 0.16 mmol) and DBU (23 μL, 0.16 mmol). The mixture was heated at 50° C. for 3.5 h, volatiles were evaporated, and the residue was purified by chromatography using a CombiFlash system (4 g silica gel column, EtOAc: heptane 0:100→100:0) to afford the SEM-protected intermediate (70 mg, quant.). This material was dissolved in CH$_2$Cl$_2$ (3 mL) and TFA (0.3 mL), stirred at rt overnight, and volatiles were evaporated. The residue was dissolved in methanol (2 mL) and ethylenediamine (0.3 mL). After standing at rt for 1 h, volatiles were evaporated and the residue was washed with water. The crude product was suspended in refluxing EtOAc, filtered and dried in vacuo to afford Example 35 (1.7 mg, 3% yield) as a white solid.

UPLC-MS: $t_R$=0.51 (M+H$^+$)=413.4

$^1$H NMR (600 MHz, DMSO-d$_6$) δ 11.68 (br s, 1H), 8.45 (br s, 1H), 8.12 (s, 1H), 7.83 (d, J=8.8 Hz, 1H), 7.17 (dd, J=3.6, 2.0 Hz, 1H), 6.63 (dd, J=3.7, 1.5 Hz, 1H), 6.54 (br s, 1H), 4.12-3.94 (m, 2H), 3.84-3.65 (m, 4H), 3.52-3.35 (m, 2H), 3.11 (s, 3H), 2.24 (br s, 1H), 1.92-1.85 (m, 1H), 1.55-1.47 (m, 1H), 1.12 (s, 3H).

Example 36

[2-[(3aS*,7aS*)-3a-methyl-5-(7H-pyrrolo[2,3-d]pyrimidin-4-yl)-1,3,4,6,7,7a-hexahydropyrrolo[3,4-c]pyridin-2-yl]-3-pyridyl]methanol (Compound 36)

Example 37

[2-[(3aS*,7aS*)-3a-methyl-5-(7H-pyrrolo[2,3-d]pyrimidin-4-yl)-1,3,4,6,7,7a-hexahydropyrrolo[3,4-c]pyridin-2-yl]-5-bromo-3-pyridyl]methanol (Compound 37)

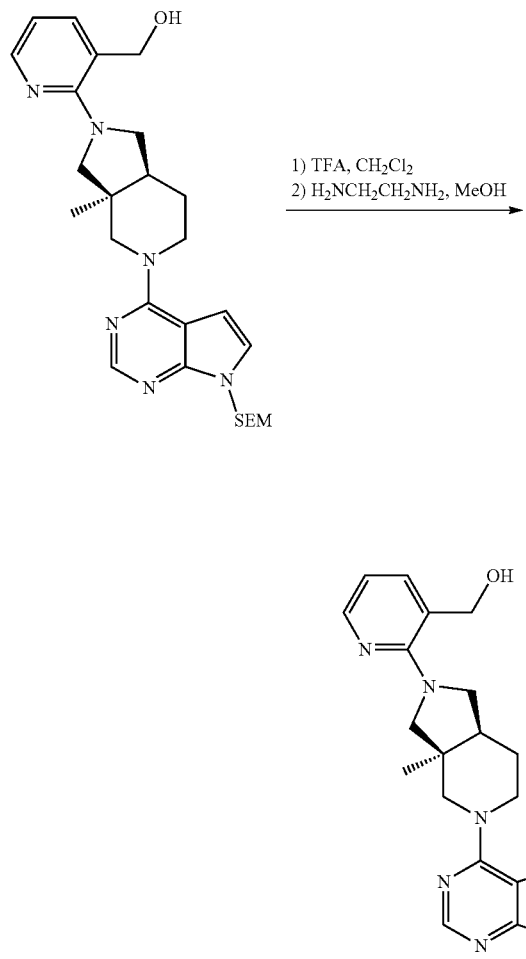

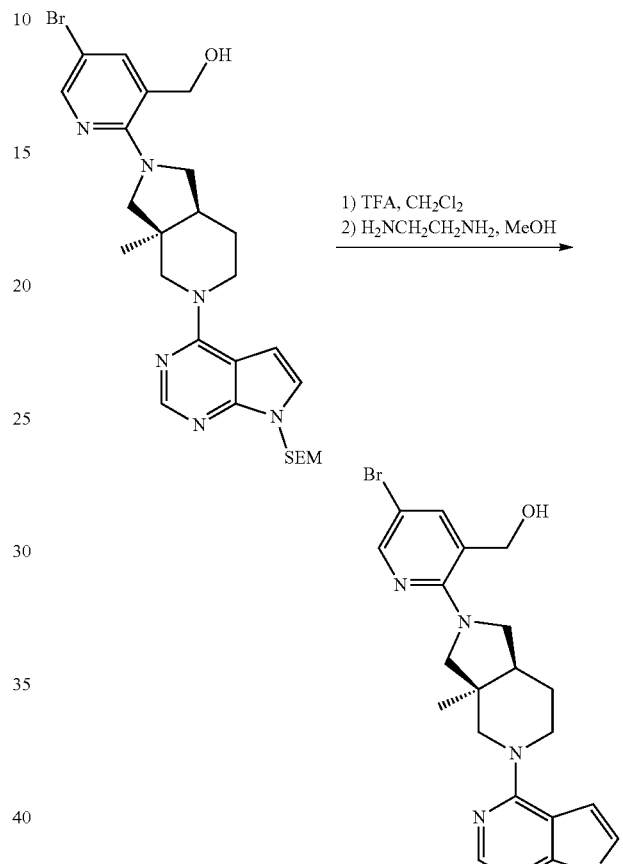

To a solution of intermediate 28 (5 mg, 0.016 mmol) in DCM (0.6 mL) was added TFA (0.2 mL) and the mixture was shaken at rt overnight. Volatiles were evaporated and the residue was dissolved in methanol (0.5 mL) and ethylenediamine (0.15 mL). After shaking for 1 h at rt the mixture was evaporated to dryness and the residue was purified by prep. HPLC (acidic) to afford Example 36 (0.7 mg, 18% yield).

UPLC-MS: $t_R$=0.36 (M+H$^+$)=365.5

$^1$H NMR (600 MHz, DMSO-d$_6$) δ 11.66 (br s, 1H), 8.11 (s, 1H), 7.94 (dd, J=4.9, 1.9 Hz, 1H), 7.50 (dd, J=7.2, 1.9 Hz, 1H), 7.16 (d, J=3.5 Hz, 1H), 6.64-6.60 (m, 2H), 4.49 (d, J=13.3 Hz, 1H), 4.45 (d, J=13.3 Hz, 1H), 4.03-3.97 (m, 1H), 3.92 (d, J=13.7 Hz, 1H), 3.83-3.77 (m, 2H), 3.74 (d, J=13.6 Hz, 1H), 3.57 (dd, J=10.4, 5.5 Hz, 1H), 3.50 (d, J=10.6 Hz, 1H), 3.25 (d, J=10.6 Hz, 1H), 2.12-2.06 (m, 1H), 1.89-1.81 (m, 1H), 1.58-1.49 (m, 1H), 1.09 (s, 3H).

To a solution of intermediate 27 (9 mg, 0.016 mmol) in DCM (0.6 mL) was added TFA (0.2 mL) and the mixture was shaken at rt for 2.5 h. Volatiles were evaporated and the residue was dissolved in methanol (0.5 mL) and ethylenediamine (0.15 mL). After shaking for 1.5 h at rt, the mixture was evaporated to dryness and the residue was purified by prep. HPLC (acidic) to afford Example 37 (3.8 mg, 55% yield).

UPLC-MS: $t_R$=0.61 (M+H$^+$)=443.4

1H NMR (600 MHz, DMSO-d$_6$) δ 11.67 (br s, 1H), 8.11 (s, 1H), 8.00 (d, J=2.4 Hz, 1H), 7.64 (d, J=2.5 Hz, 1H), 7.16 (d, J=3.6 Hz, 1H), 6.61 (d, J=3.6 Hz, 1H), 4.50 (d, J=13.7 Hz, 1H), 4.47 (d, J=13.6 Hz, 1H), 4.02-3.96 (m, 1H), 3.91 (d, J=13.6 Hz, 1H), 3.83-3.76 (m, 2H), 3.73 (d, J=13.6 Hz, 1H), 3.56 (dd, J=10.5, 5.5 Hz, 1H), 3.49 (d, J=10.6 Hz, 1H), 3.24 (d, J=10.6 Hz, 1H), 2.13-2.07 (m, 1H), 1.88-1.80 (m, 1H), 1.55-1.46 (m, 1H), 1.09 (s, 3H).

Examples 38-45 and 47

These examples are prepared according to the below general procedure for nucleophilic aromatic substitution and SEM deprotection

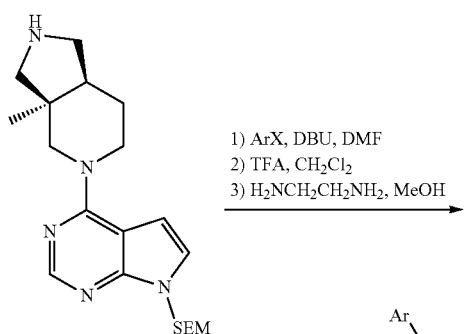

1) ArX, DBU, DMF
2) TFA, CH₂Cl₂
3) H₂NCH₂CH₂NH₂, MeOH

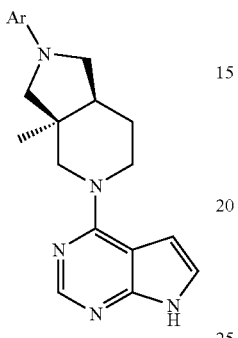

The compounds of examples 38-45 and 47 were prepared according to the following method: A solution of intermediate 23 (20 mg, 0.052 mmol) and DBU (16 µL, 0.11 mmol) in DMF (0.5 mL) was added to the respective heteroaryl halide (1.2 equiv.) in a 4 mL screwcap vial, and the mixture was shaken at the temperature and time indicated below. The reaction mixture was purified by prep HPLC (basic) to afford the SEM-protected intermediates, which were dissolved in CH₂Cl₂ (0.5 mL) and TFA (0.5 mL). After standing for 1 h at rt volatiles were evaporated and the residue was dissolved in methanol (0.5 mL) and ethylenediamine (0.1 mL). After standing at rt for 6 h, a precipitate had formed. This was collected by filtration, washed with a drop of methanol and vacuum dried to afford the pure products as white or yellow solids. Alternatively, in those cases were no precipitate formed, the reaction mixture was purified by prep HPLC (basic) to afford pure products.

Example 38

4-[(3aR*,7aS*)-3a-methyl-2-(4-methylsulfonylphenyl)-1,3,4,6,7,7a-hexahydropyrrolo[3,4-c]pyridin-5-yl]-7H-pyrrolo[2,3-d]pyrimidine (Compound 38)

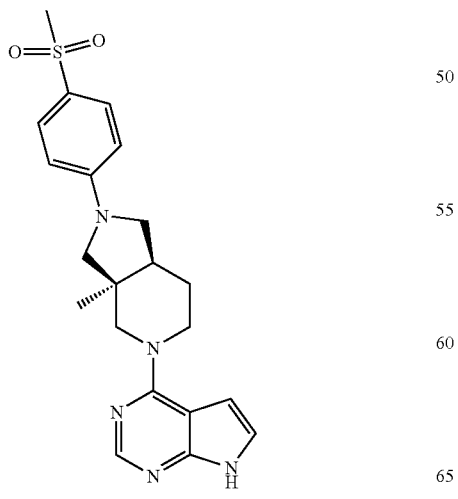

Prepared from intermediate 23 and 1-fluoro-4-methylsulfonyl-benzene (11 mg, 0.063 mmol) heated at 80° C. for 2 h, then at 100° C. overnight. The title compound was purified by prep HPLC (basic). Yield: 9.7 mg, 46%.

¹H NMR (300 MHz, DMSO-d₆) δ 11.66 (br s, 1H), 8.13 (s, 1H), 7.61 (d, J=8.8 Hz, 2H), 7.17 (d, J=3.6 Hz, 1H), 6.62 (d, J=3.6 Hz, 1H), 6.59 (d, J=8.9 Hz, 2H), 4.04-3.96 (m, 1H), 3.92 (d, J=13.8 Hz, 1H), 3.88-3.80 (m, 1H), 3.76 (d, J=13.7 Hz, 1H), 3.58 (dd, J=10.2, 7.2 Hz, 1H), 3.39-3.25 (m, 2H), 3.09 (d, J=10.0 Hz, 1H), 3.03 (s, 3H), 2.30-2.19 (m, 1H), 1.96-1.83 (m, 1H), 1.59-1.46 (m, 1H), 1.12 (s, 3H).

Example 39

4-[(3aR*,7aS*)-3a-methyl-2-pyrimidin-4-yl-1,3,4,6,7,7a-hexahydropyrrolo[3,4-c]pyridin-5-yl]-7H-pyrrolo[2,3-d]pyrimidine (Compound 39)

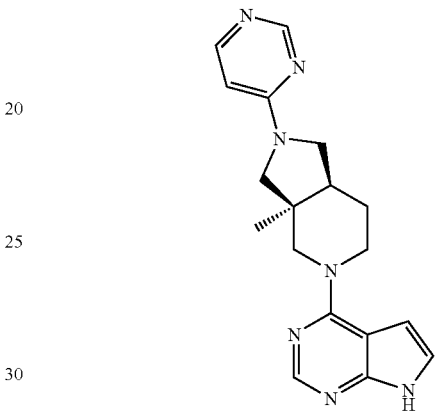

Prepared from intermediate 23 and 4-chloropyrimidine (7.1 mg, 0.062 mmol) heated at 30° C. for 1 h 45 min, then at 50° C. for 2 h. The title compound was purified by prep HPLC (basic). Yield: 13.5 mg, 78%.

¹H NMR (300 MHz, DMSO-d₆) δ 11.62 (br s, 1H), 8.41 (br s, 1H), 8.12 (s, 1H), 8.10 (d, J=6.2 Hz, 1H), 7.17 (d, J=3.6 Hz, 1H), 6.62 (d, J=3.6 Hz, 1H), 6.43 (br s, 1H), 4.13-3.87 (m, 2H), 3.83-3.53 (m, 4H), 3.48-2.98 (m, 2H), 2.29-2.14 (m, 1H), 1.94-1.81 (m, 1H), 1.56-1.42 (m, 1H), 1.10 (s, 3H).

Example 40

6-[(3aR*,7aS*)-3a-methyl-5-(7H-pyrrolo[2,3-d]pyrimidin-4-yl)-1,3,4,6,7,7a-hexahydropyrrolo[3,4-c]pyridin-2-yl]-4-methyl-pyridine-3-carbonitrile (Compound 40)

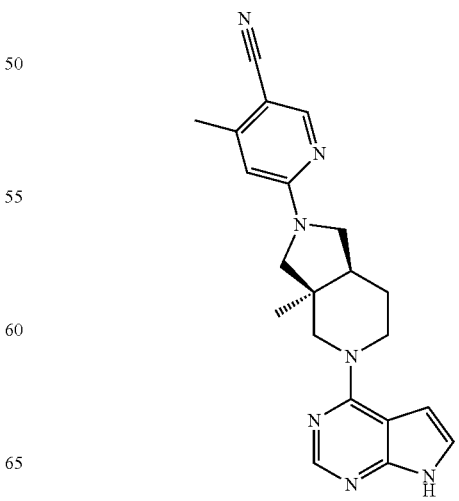

Prepared from intermediate 23 and 6-chloro-4-methylpyridine-3-carbonitrile (9.4 mg, 0.062 mmol) heated at 30° C. for 1 h 45 min, then at 50° C. for 2 h. Yield: 11.5 mg, 60%.

¹H NMR (600 MHz, DMSO-d₆) δ 11.72 (br s, 1H), 8.32 (br d, 1H), 8.12 (s, 1H), 7.18 (d, J=3.6 Hz, 1H), 6.62 (d, J=3.6 Hz, 1H), 6.43 (br d, 1H), 4.11-4.02 (m, 1H), 3.99 (d, J=13.8 Hz, 1H), 3.80-3.73 (m, 2H), 3.70 (d, J=13.8 Hz, 1H), 3.66-3.53 (m, 1H), 3.47-3.39 (m, 1H), 3.30-3.21 (m, 1H), 2.38-2.12 (m, 4H), 1.92-1.82 (m, 1H), 1.54-1.43 (m, 1H), 1.10 (s, 3H).

Example 41

2-[(3aS*,7aS*)-3a-methyl-5-(7H-pyrrolo[2,3-d]pyrimidin-4-yl)-1,3,4,6,7,7a-hexahydropyrrolo[3,4-c]pyridin-2-yl]pyrimidine-5-carbonitrile (Compound 41)

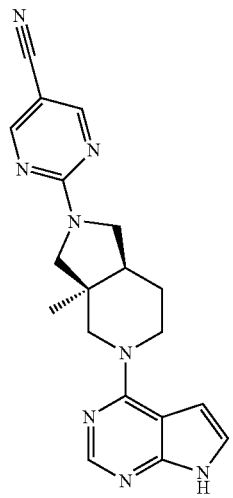 [SMILES: C[C@]12CN(c3ncc(C#N)cn3)C[C@H]1CCN(c1ncnc3[nH]ccc13)C2]

Prepared from intermediate 23 and 2-chloropyrimidine-5-carbonitrile (8.6 mg, 0.062 mmol) heated at 30° C. for 1 h 15 min. Yield: 13.8 mg, 74%.

¹H NMR (600 MHz, DMSO-d₆) δ 11.72 (br s, 1H), 8.74 (d, J=2.9 Hz, 1H), 8.68 (d, J=2.9 Hz, 1H), 8.12 (s, 1H), 7.18 (d, J=3.6 Hz, 1H), 6.63 (d, J=3.6 Hz, 1H), 4.13-4.06 (m, 1H), 4.05 (d, J=13.8 Hz, 1H), 3.78 (dd, J=12.1, 7.0 Hz, 1H), 3.75-3.71 (m, 1H), 3.69 (d, J=13.9 Hz, 1H), 3.57 (dd, J=12.1, 5.0 Hz, 1H), 3.46 (d, J=12.0 Hz, 1H), 3.31 (d, J=12.0 Hz, 1H), 2.26-2.19 (m, 1H), 1.90-1.82 (m, 1H), 1.52-1.44 (m, 1H), 1.12 (s, 3H).

Example 42

6-[(3aS*,7aS*)-3a-methyl-5-(7H-pyrrolo[2,3-d]pyrimidin-4-yl)-1,3,4,6,7,7a-hexahydropyrrolo[3,4-c]pyridin-2-yl]pyridazine-3-carbonitrile (Compound 42)

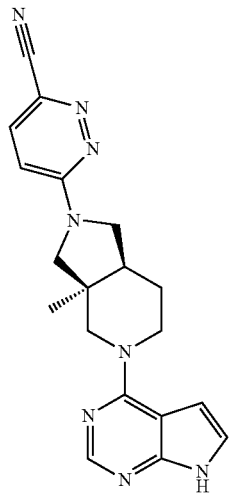 [SMILES: C[C@]12CN(c3ccc(C#N)nn3)C[C@H]1CCN(c1ncnc3[nH]ccc13)C2]

Prepared from intermediate 23 and 6-fluoropyridazine-3-carbonitrile (7.6 mg, 0.062 mmol) heated at 30° C. for 1 h. Yield: 8.4 mg, 45%.

¹H NMR (300 MHz, DMSO-d₆) δ 11.66 (br s, 1H), 8.13 (s, 1H), 7.79 (d, J=9.5 Hz, 1H), 7.17 (d, J=3.6 Hz, 1H), 6.91 (br d, J=9.5 Hz, 1H), 6.62 (d, J=3.6 Hz, 1H), 4.12-3.91 (m, 2H), 3.89-3.13 (m, 6H), 2.35-2.20 (m, 1H), 1.99-1.82 (m, 1H), 1.63-1.47 (m, 1H), 1.14 (s, 3H).

Example 43

5-[(3aS*,7aS*)-3a-methyl-5-(7H-pyrrolo[2,3-d]pyrimidin-4-yl)-1,3,4,6,7,7a-hexahydropyrrolo[3,4-c]pyridin-2-yl]pyrazine-2-carbonitrile (Compound 43)

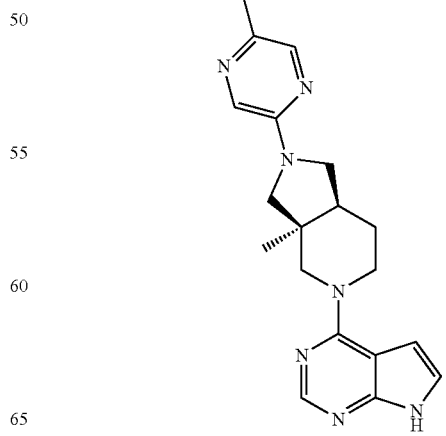

Prepared from intermediate 23 and 5-chloropyrazine-2-carbonitrile (8.6 mg, 0.062 mmol) heated at 30° C. for 2 h 20 min, then at 50° C. for 1 h. Yield: 10.6 mg, 57%.

$^1$H NMR (300 MHz, DMSO-$d_6$) δ 11.65 (br s, 1H), 8.50 (br s, 1H), 8.12 (s, 1H), 8.03 (br s, 1H), 7.17 (d, J=3.6 Hz, 1H), 6.62 (d, J=3.6 Hz, 1H), 4.18-3.88 (m, 2H), 3.87-3.64 (m, 2H), 3.64-3.41 (m, 2H), 3.38-3.22 (m, 2H), 2.39-2.13 (m, 1H), 1.97-1.82 (m, 1H), 1.64-1.45 (m, 1H), 1.12 (s, 3H).

Example 44

6-[(3aS*,7aS*)-3a-methyl-5-(7H-pyrrolo[2,3-d]pyrimidin-4-yl)-1,3,4,6,7,7a-hexahydropyrrolo[3,4-c]pyridin-2-yl]-5-methyl-pyridine-3-carbonitrile (Compound 44)

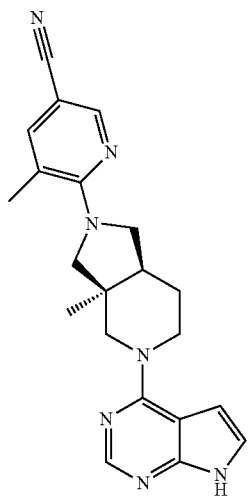 [SMILES: Cc1cc(C#N)cnc1N1C[C@H]2CCN(c3ncnc4[nH]ccc34)C[C@@]2(C)C1]

Prepared from intermediate 23 and 6-chloro-5-methyl-pyridine-3-carbonitrile (9.4 mg, 0.062 mmol) heated at 30° C. for 1 h. Yield: 9.2 mg, 48%.

$^1$H NMR (300 MHz, DMSO-$d_6$) δ 11.66 (br s, 1H), 8.27 (d, J=2.3 Hz, 1H), 8.12 (s, 1H), 7.58 (dd, J=2.2, 0.9 Hz, 1H), 7.17 (d, J=3.6 Hz, 1H), 6.62 (d, J=3.6 Hz, 1H), 4.09-3.88 (m, 3H), 3.87-3.68 (m, 3H), 3.64 (d, J=11.2 Hz, 1H), 3.38 (d, J=11.2 Hz, 1H), 2.36 (s, 3H), 2.19-2.06 (m, 1H), 1.93-1.77 (m, 1H), 1.59-1.42 (m, 1H), 1.10 (s, 3H).

Example 45

6-[(3aR*,7aS*)-3a-methyl-5-(7H-pyrrolo[2,3-d]pyrimidin-4-yl)-1,3,4,6,7,7a-hexahydropyrrolo[3,4-c]pyridin-2-yl]-2-methyl-pyridine-3-carbonitrile (Compound 45)

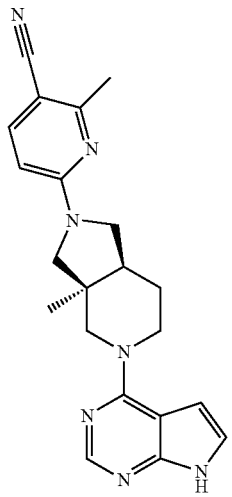 [SMILES: Cc1nc(N2C[C@H]3CCN(c4ncnc5[nH]ccc45)C[C@@]3(C)C2)ccc1C#N]

Prepared from intermediate 23 and 6-chloro-2-methyl-pyridine-3-carbonitrile (9.4 mg, 0.062 mmol) heated at 30° C. for 2 h 20 min, then at 50° C. for 1 h. Yield: 8.1 mg, 42%.

$^1$H NMR (300 MHz, DMSO-$d_6$) δ 11.66 (br s, 1H), 8.12 (s, 1H), 7.69 (d, J=8.8 Hz, 1H), 7.17 (d, J=3.6 Hz, 1H), 6.62 (d, J=3.6 Hz, 1H), 6.34 (br s, 1H), 4.15-3.87 (m, 2H), 3.86-3.54 (m, 2H), 3.47-3.07 (m, 4H), 2.43 (s, 3H), 2.30-2.11 (m, 1H), 1.95-1.80 (m, 1H), 1.58-1.43 (m, 1H), 1.10 (s, 3H).

Example 47

6-[(3aS*,7aS*)-3a-methyl-5-(7H-pyrrolo[2,3-d]pyrimidin-4-yl)-1,3,4,6,7,7a-hexahydropyrrolo[3,4-c]pyridin-2-yl]pyridine-3-carbonitrile (Compound 47)

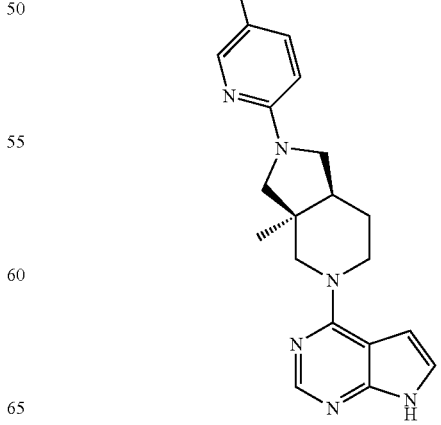

Prepared from intermediate 23 and 6-chloropyridine-3-carbonitrile (7.9 mg, 0.057 mmol) heated at 30° C. for 1 h. The crude solid was triturated with MeCN to afford the title compound. Yield: 2.4 mg, 13%.

UPLC-MS: $t_R$=0.59 (M+H$^+$)=360.3

$^1$H NMR (600 MHz, DMSO-d$_6$) δ 11.68 (br s, 1H), 8.42 (br s, 1H), 8.12 (s, 1H), 7.78 (br d, J=7.8 Hz, 1H), 7.17 (d, J=3.5 Hz, 1H), 6.62 (d, J=3.6 Hz, 1H), 6.51 (br s, 1H), 4.15-3.89 (m, 2H), 3.85-3.53 (m, 3H), 3.50-3.12 (m, 3H), 2.30-2.16 (m, 1H), 1.91-1.84 (m, 1H), 1.55-1.45 (m, 1H), 1.11 (s, 3H).

Example 46

1-[(3aS*,7aS*)-3a-methyl-5-(7H-pyrrolo[2,3-d]pyrimidin-4-yl)-1,3,4,6,7,7a-hexahydropyrrolo[3,4-c]pyridine-2-carbonyl]cyclopentanecarbonitrile (Compound 46)

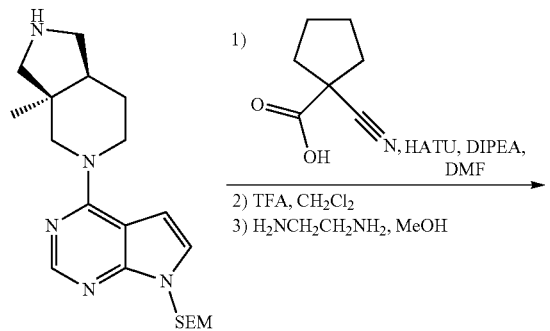

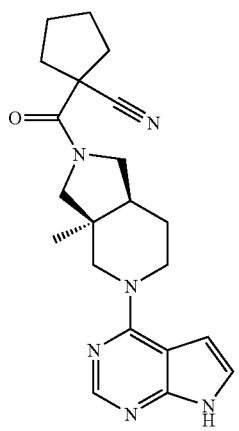

To a solution of intermediate 23 (20 mg, 0.052 mmol) in DMF (0.6 mL) was added 1-cyanocyclopentanecarboxylic acid (10.8 mg, 0.0774 mmol), DIPEA (27 µL, 0.15 mmol) and HATU (29 mg, 0.077 mmol). The mixture was shaken at 30° C. for 1 h, volatiles were evaporated and the residue was dissolved in DCM (0.5 mL) and TFA (0.1 mL). The mixture was shaken at rt overnight, volatiles were evaporated and the residue was coevaporated from methanol to remove excess TFA. The residue was then dissolved in methanol (0.5 mL), ethylenediamine (0.1 mL) was added and the mixture was shaken at rt for 1 h. Volatiles were evaporated and the residue was purified by prep HPLC (acidic) to afford Example 46 (1.3 mg, 6% yield). The $^1$H NMR spectrum shows two sets of peaks in a ca. 1:1 ratio corresponding to two amide bond rotamers.

UPLC-MS: $t_R$=0.58 (M+H$^+$)=379.4

$^1$H NMR (600 MHz, DMSO-d$_6$) δ 11.69 (br s, 0.5H), 11.67 (br s, 0.5H), 8.12 (s, 0.5H), 8.11 (s, 0.5H), 7.17 (dd, J=3.7, 1.8 Hz, 1H), 6.66 (d, J=3.6 Hz, 0.5H), 6.61 (d, J=3.6 Hz, 0.5H), 4.21-4.13 (m, 1H), 4.10 (d, J=13.8 Hz, 0.5H), 3.98-3.87 (m, 1.5H), 3.81-3.73 (m, 0.5H), 3.72-3.67 (m, 1H), 3.67-3.57 (m, 1.5H), 3.54 (d, J=13.8 Hz, 0.5H), 3.47-3.39 (m, 1H), 3.29 (d, J=12.2 Hz, 0.5H), 3.14 (d, J=12.2 Hz, 0.5H), 2.35-2.26 (m, 1H), 2.25-2.05 (m, 4H), 1.91-1.80 (m, 1H), 1.76-1.58 (m, 4H), 1.57-1.49 (m, 0.5H), 1.48-1.40 (m, 0.5H), 1.09 (s, 1.5H), 1.08 (s, 1.5H).

JAK Kinase Assays:

Human baculovirus-expressed JAK1, 2, 3 and TYK2 were purchased from Carna Biosciences, Inc. All four purified enzymes contain only the catalytic domain. JAK1 (aa 850-1154) and TYK2 (aa 871-1187) are expressed with an N-terminally fused GST-tag, and JAK2 and JAK3 with an N-terminally fused His-tag.

Inhibition of phosphorylation of a synthetic peptide was measured in an HTRF-based assay using the TK substrate-Biotin from the Cisbio HTRFKinEASE TK kit. First, 2 µl of TK solution (TK substrate-biotin in kinase buffer [1× enzymatic buffer from HTRFKinEASE TK kit, 1 mM DTT]) is added to a plate containing 1 µl prediluted compound (final assay concentration DMSO: 0.75%). Then, 5 µl kinase-ATP mix (prepared in kinase buffer) is added to the wells and the plates are incubated at RT for 20-30 min. For all four kinases a concentration of ATP that corresponded to the Km for ATP was used. The final concentrations of buffers, substrate, kinase and ATP were: JAK1: 50 mM Hepes buffer pH 7.0, 0.01% BSA, 10 mM MgCl$_2$, 1 mM DTT, 7 µM ATP, 50 nM SEB, 1 µM TK Substrate-Biotin and 5 ng JAK1; JAK2: 50 mM Hepes buffer pH 7.0, 0.01% BSA, 5 mM MgCl$_2$, 1 mM DTT, 4 µM ATP, 1 µM TK Substrate-Biotin and 0.1 ng JAK2; JAK3: 50 mM Hepes buffer pH 7.0, 0.01% BSA, 5 mM MgCl$_2$, 1 mM DTT, 2 µM ATP, 1 µM TK Substrate-Biotin and 0.3 ng JAK3; TYK2: 50 mM Hepes buffer pH 7.0, 0.01% BSA, 5 mM MgCl$_2$, 1 mM DTT, 13 µM ATP, 50 nM SEB, 1 µM TK Substrate-Biotin and 0.8 ng TYK2. Thereafter, the kinase reaction is stopped by adding 4 µl detection mix (final concentrations: 50 mM Hepes buffer pH 7.0, 0.01% BSA, 0.8 M KF, 20 mM EDTA, 42 nM Streptavidin-XL665 and 1:400 STK Ab Cryptate) and the plates are incubated overnight in the dark. The HTRF signal is read using an Envision plate reader.

TABLE 1

JAK kinase inhibitory data
In Table 1 selected JAK kinase inhibitory activities are listed.

| Example # | IUPAC name | Structure | JAK1 EC50 nM | JAK2 EC50 nM | JAK3 EC50 nM | TYK2 EC50 nM |
|---|---|---|---|---|---|---|
| 1 | (4aR,8aS)-8a-methyl-7-(7H-pyrrolo[2,3-d]pyrimidin-4-yl)-3,4,4a,5,6,8-hexahydro-1H-2,7-naphthyridine-2-carbonitrile | 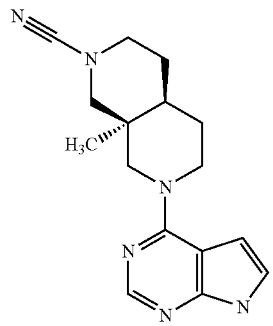 [SMILES: C[C@]12CN(C#N)CC[C@H]1CCN(c1ncnc3[nH]ccc13)C2] | 1 | 4 | 15 | 13 |
| 2 | (4aR*,8aS*)-8a-methyl-7-(7H-pyrrolo[2,3-d]pyrimidin-4-yl)-3,4,4a,5,6,8-hexahydro-1H-2,7-naphthyridine-2-carbonitrile | 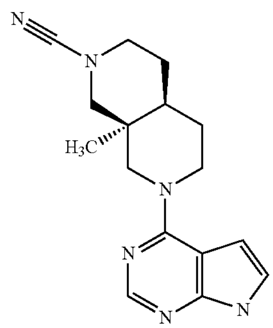 [SMILES: C[C@]12CN(C#N)CC[C@H]1CCN(c1ncnc3[nH]ccc13)C2] | 1 | 6 | 25 | 27 |
| 3 | (4aS,8aR)-8a-methyl-7-(7H-pyrrolo[2,3-d]pyrimidin-4-yl)-3,4,4a,5,6,8-hexahydro-1H-2,7-naphthyridine-2-carbonitrile | 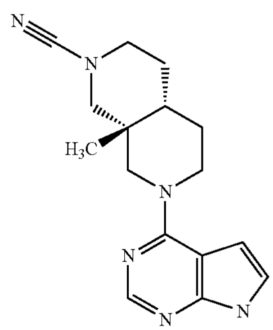 [SMILES: C[C@@]12CN(C#N)CC[C@@H]1CCN(c1ncnc3[nH]ccc13)C2] | 237 | 428 | 924 | 1480 |
| 4 | 5-[(4aR*,8aS*)-8a-methyl-7-(7H-pyrrolo[2,3-d]pyrimidin-4-yl)-3,4,4a,5,6,8-hexahydro-1H-2,7-naphthyridin-2-yl]pyrazine-2-carbonitrile | 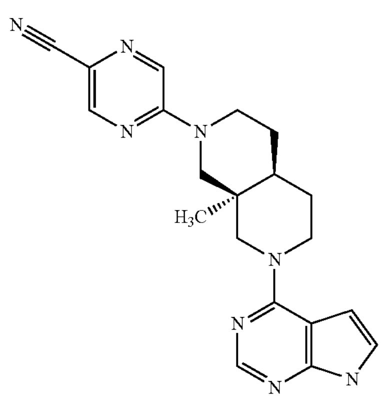 [SMILES: C[C@]12CN(c3cnc(C#N)cn3)CC[C@H]1CCN(c1ncnc3[nH]ccc13)C2] | 4 | 25 | 4 | 148 |

TABLE 1-continued

JAK kinase inhibitory data
In Table 1 selected JAK kinase inhibitory activities are listed.

| Example # | IUPAC name | Structure | JAK1 EC50 nM | JAK2 EC50 nM | JAK3 EC50 nM | TYK2 EC50 nM |
|---|---|---|---|---|---|---|
| 5 | 6-[(4aR*,8aS*)-8a-methyl-7-(7H-pyrrolo[2,3-d]pyrimidin-4-yl)-3,4,4a,5,6,8-hexahydro-1H-2,7-naphthyridin-2-yl]pyridine-3-carbonitrile | 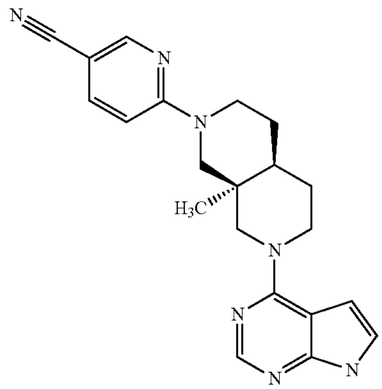 [SMILES: C[C@]12CN(c3ccc(C#N)cn3)CC[C@H]1CCN(c1ncnc3[nH]ccc13)C2] | 10 | 80 | 7 | 453 |
| 6 | 6-[(4aR*,8aS*)-8a-methyl-7-(7H-pyrrolo[2,3-d]pyrimidin-4-yl)-3,4,4a,5,6,8-hexahydro-1H-2,7-naphthyridin-2-yl]pyridazine-3-carbonitrile | 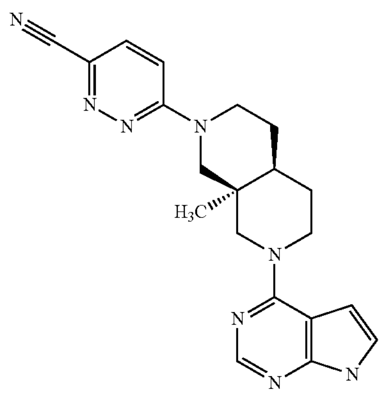 [SMILES: C[C@]12CN(c3ccc(C#N)nn3)CC[C@H]1CCN(c1ncnc3[nH]ccc13)C2] | 17 | 64 | 9 | 634 |
| 7 | 2-[(4aR*,8aS*)-8a-methyl-7-(7H-pyrrolo[2,3-d]pyrimidin-4-yl)-3,4,4a,5,6,8-hexahydro-1H-2,7-naphthyridin-2-yl]pyrimidine-5-carbonitrile | 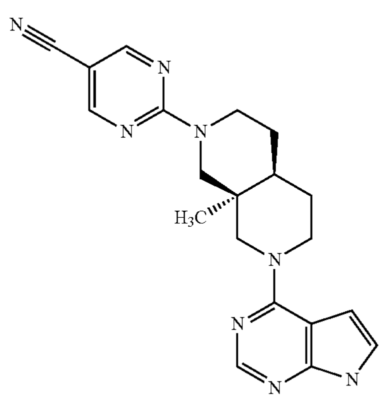 [SMILES: C[C@]12CN(c3ncc(C#N)cn3)CC[C@H]1CCN(c1ncnc3[nH]ccc13)C2] | 46 | 140 | 5 | 740 |

TABLE 1-continued

JAK kinase inhibitory data
In Table 1 selected JAK kinase inhibitory activities are listed.

| Example # | IUPAC name | Structure | JAK1 EC50 nM | JAK2 EC50 nM | JAK3 EC50 nM | TYK2 EC50 nM |
|---|---|---|---|---|---|---|
| 8 | 6-[(4aS*,8aR*)-8a-methyl-7-(7H-pyrrolo[2,3-d]pyrimidin-4-yl)-3,4,4a,5,6,8-hexahydro-1H-2,7-naphthyridin-2-yl]-4-methyl-pyridine-3-carbonitrile | 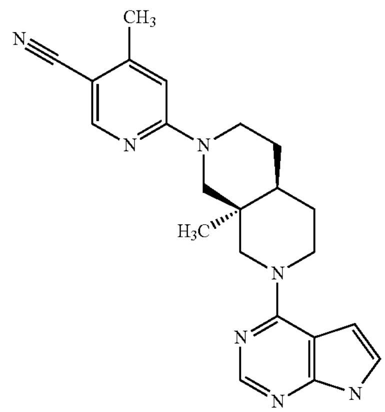 [SMILES: Cc1cc(N2CC[C@H]3CCN(c4ncnc5[nH]ccc45)C[C@@]3(C)C2)ncc1C#N] | 86 | 269 | 21 | 2110 |
| 9 | (4aR*,8aS*)-8a-methyl-7-(7H-pyrrolo[2,3-d]pyrimidin-4-yl)-3,4,4a,5,6,8-hexahydro-1H-2,7-naphthyridine-2-sulfonamide | 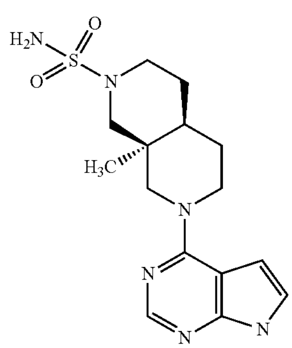 [SMILES: C[C@@]12CN(c3ncnc4[nH]ccc34)CC[C@@H]1CCN(S(N)(=O)=O)C2] | 39 | 58 | 8 | 241 |
| 10 | 6-[(4aS*,8aR*)-8a-methyl-7-(7H-pyrrolo[2,3-d]pyrimidin-4-yl)-3,4,4a,5,6,8-hexahydro-1H-2,7-naphthyridin-2-yl]-2-methyl-pyridine-3-carbonitrile | 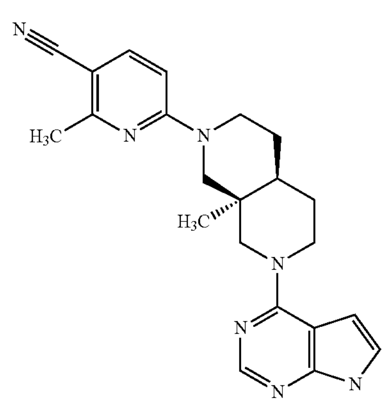 [SMILES: Cc1nc(N2CC[C@H]3CCN(c4ncnc5[nH]ccc45)C[C@@]3(C)C2)ccc1C#N] | 112 | 469 | 204 | 3880 |

TABLE 1-continued

JAK kinase inhibitory data
In Table 1 selected JAK kinase inhibitory activities are listed.

| Example # | IUPAC name | Structure | JAK1 EC50 nM | JAK2 EC50 nM | JAK3 EC50 nM | TYK2 EC50 nM |
|---|---|---|---|---|---|---|
| 11 | 6-[(4aS*,8aR*)-8a-methyl-7-(7H-pyrrolo[2,3-d]pyrimidin-4-yl)-3,4,4a,5,6,8-hexahydro-1H-2,7-naphthyridin-2-yl]-5-methyl-pyridine-3-carbonitrile | 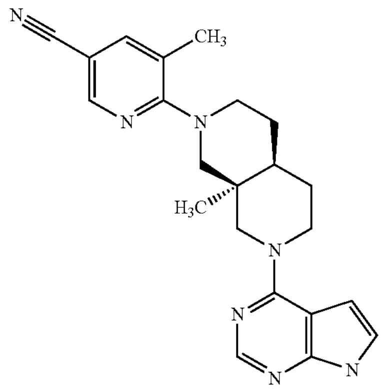 [SMILES: Cc1cc(C#N)cnc1N1CC[C@H]2CCN(c3ncnc4[nH]ccc34)C[C@@]2(C)C1] | 86 | 380 | 85 | 976 |
| 12 | (4aS*,8aR*)-2-(5-bromo-4-methyl-2-pyridyl)-8a-methyl-7-(7H-pyrrolo[2,3-d]pyrimidin-4-yl)-3,4,4a,5,6,8-hexahydro-1H-2,7-naphthyridine | 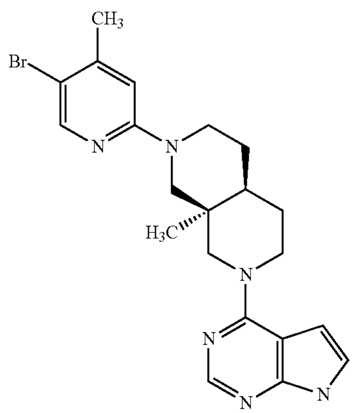 [SMILES: Cc1cc(N2CC[C@H]3CCN(c4ncnc5[nH]ccc45)C[C@@]3(C)C2)ncc1Br] | 203 | 937 | 60 | 4270 |
| 13 | (4aR*,8aS*)-8a-methyl-2-methylsulfonyl-7-(7H-pyrrolo[2,3-d]pyrimidin-4-yl)-3,4,4a,5,6,8-hexahydro-1H-2,7-naphthyridine | 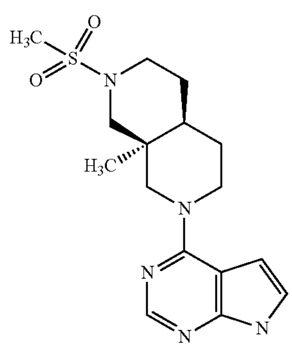 [SMILES: C[C@@]12CN(c3ncnc4[nH]ccc34)CC[C@@H]1CCN(S(C)(=O)=O)C2] | 72 | 90 | 75 | 326 |
| 14 | (4aS*,8aR*)-2-(5-bromo-6-methyl-2-pyridyl)-8a-methyl-7-(7H-pyrrolo[2,3-d]pyrimidin-4-yl)-3,4,4a,5,6,8-hexahydro-1H-2,7-naphthyridine | 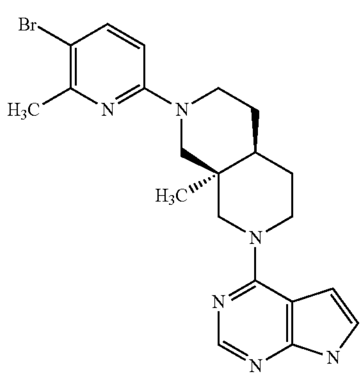 [SMILES: Cc1nc(N2CC[C@H]3CCN(c4ncnc5[nH]ccc45)C[C@@]3(C)C2)ccc1Br] | 301 | 990 | 604 | 5780 |

TABLE 1-continued

JAK kinase inhibitory data
In Table 1 selected JAK kinase inhibitory activities are listed.

| Example # | IUPAC name | Structure | JAK1 EC50 nM | JAK2 EC50 nM | JAK3 EC50 nM | TYK2 EC50 nM |
|---|---|---|---|---|---|---|
| 15 | 1-[(4aR*,8aS*)-8a-ethyl-7-(7H-pyrrolo[2,3-d]pyrimidin-4-yl)-3,4,4a,5,6,8-hexahydro-1H-2,7-naphthyridin-2-yl]ethanone | 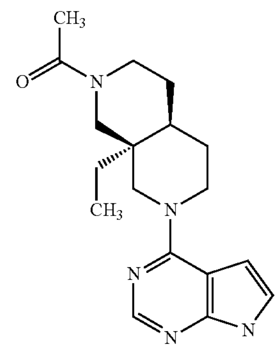 [SMILES: CC[C@]12CN(C(C)=O)CC[C@H]1CCN(c1ncnc3[nH]ccc13)C2] | 121 | 453 | 69 | 1040 |
| 16 | (4aR*,8aS*)-8a-ethyl-7-(7H-pyrrolo[2,3-d]pyrimidin-4-yl)-3,4,4a,5,6,8-hexahydro-1H-2,7-naphthyridine-2-carbaldehyde | 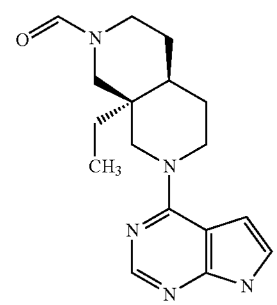 [SMILES: CC[C@]12CN(C=O)CC[C@H]1CCN(c1ncnc3[nH]ccc13)C2] | 13 | 41 | 43 | 176 |
| 17 | (4aR*,8aS*)-8a-ethyl-7-(7H-pyrrolo[2,3-d]pyrimidin-4-yl)-3,4,4a,5,6,8-hexahydro-1H-2,7-naphthyridine-2-sulfonamide | 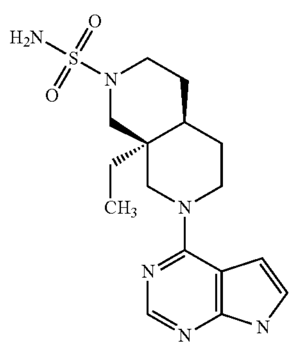 [SMILES: CC[C@@]12CN(c3ncnc4[nH]ccc34)CC[C@@H]1CCN(S(N)(=O)=O)C2] | 2 | 7 | 3 | 45 |
| 18 | (4aR,8aS)-8a-ethyl-7-(7H-pyrrolo[2,3-d]pyrimidin-4-yl)-3,4,4a,5,6,8-hexahydro-1H-2,7-naphthyridine-2-sulfonamide | 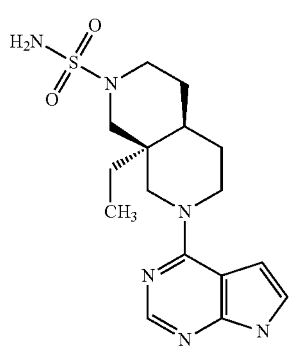 [SMILES: CC[C@@]12CN(c3ncnc4[nH]ccc34)CC[C@@H]1CCN(S(N)(=O)=O)C2] | 2 | 3 | 2 | 17 |

TABLE 1-continued

JAK kinase inhibitory data
In Table 1 selected JAK kinase inhibitory activities are listed.

| Example # | IUPAC name | Structure | JAK1 EC50 nM | JAK2 EC50 nM | JAK3 EC50 nM | TYK2 EC50 nM |
|---|---|---|---|---|---|---|
| 19 | (4aS,8aR)-8a-ethyl-7-(7H-pyrrolo[2,3-d]pyrimidin-4-yl)-3,4,4a,5,6,8-hexahydro-1H-2,7-naphthyridine-2-sulfonamide | 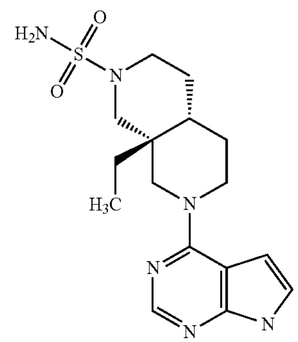 [SMILES: CC[C@]12CN(c3ncnc4[nH]ccc34)CC[C@H]1CCN(S(N)(=O)=O)C2] | 146 | 208 | 151 | 1880 |
| 20 | 2-[(4aR*,8aS*)-8a-ethyl-7-(7H-pyrrolo[2,3-d]pyrimidin-4-yl)-3,4,4a,5,6,8-hexahydro-1H-2,7-naphthyridin-2-yl]-5-bromo-1,3,4-thiadiazole | 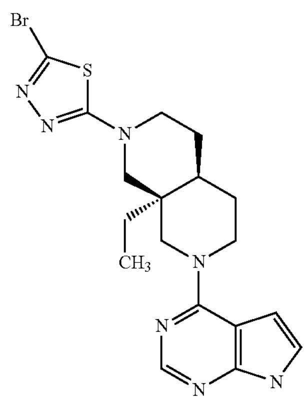 [SMILES: CC[C@]12CN(c3nnc(Br)s3)CC[C@H]1CCN(c1ncnc3[nH]ccc13)C2] | 4 | 17 | 5 | 269 |
| 21 | (4aS,8aR)-8a-ethyl-7-(7H-pyrrolo[2,3-d]pyrimidin-4-yl)-3,4,4a,5,6,8-hexahydro-1H-2,7-naphthyridine-2-carbonitrile | 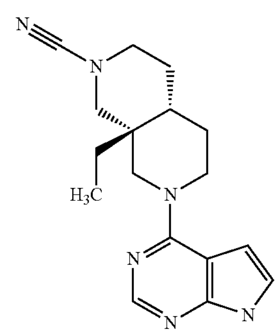 [SMILES: CC[C@@]12CN(C#N)CC[C@@H]1CCN(c1ncnc3[nH]ccc13)C2] | 80 | 187 | 578 | 988 |
| 22 | (4aR,8aS)-8a-ethyl-7-(7H-pyrrolo[2,3-d]pyrimidin-4-yl)-3,4,4a,5,6,8-hexahydro-1H-2,7-naphthyridine-2-carbonitrile | 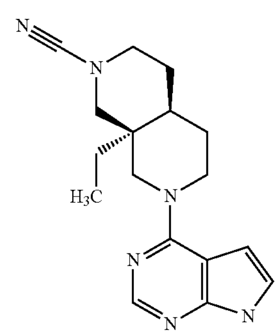 [SMILES: CC[C@]12CN(C#N)CC[C@H]1CCN(c1ncnc3[nH]ccc13)C2] | 1 | 2 | 6 | 6 |

TABLE 1-continued

JAK kinase inhibitory data
In Table 1 selected JAK kinase inhibitory activities are listed.

| Example # | IUPAC name | Structure | JAK1 EC50 nM | JAK2 EC50 nM | JAK3 EC50 nM | TYK2 EC50 nM |
|---|---|---|---|---|---|---|
| 23 | (4aR*,8aS*)-8a-ethyl-7-(7H-pyrrolo[2,3-d]pyrimidin-4-yl)-3,4,4a,5,6,8-hexahydro-1H-2,7-naphthyridine-2-carbonitrile | 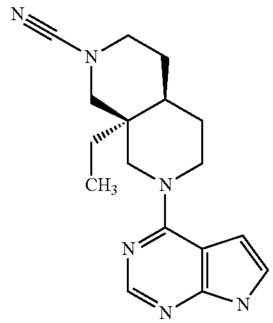 [SMILES: CC[C@]12CN(C#N)CC[C@H]1CCN(c1ncnc3[nH]ccc13)C2] | 2 | 4 | 14 | 11 |
| Intermediate 10 | 8a-ethyl-7-(7H-pyrrolo[2,3-d]pyrimidin-4-yl)-1,2,3,4,4a,5,6,8-octahydro-2,7-naphthyridine | 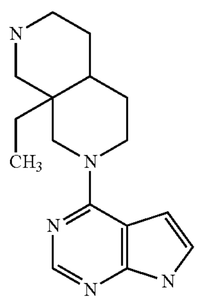 [SMILES: CCC12CNCCC1CCN(c1ncnc3[nH]ccc13)C2] | 16 | 25 | 157 | 1980 |
| 25 | 2-[(4aR*,8aS*)-8a-ethyl-7-(7H-pyrrolo[2,3-d]pyrimidin-4-yl)-3,4,4a,5,6,8-hexahydro-1H-2,7-naphthyridin-2-yl]thiazole-4-carbonitrile | 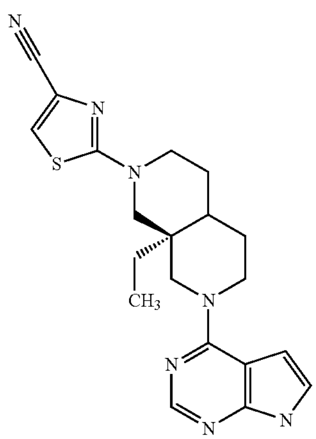 | 46 | 139 | 29 | 1110 |
| 26 | 4-[(3aS*,7aS*)-3a-methyl-2-methylsulfonyl-1,3,4,6,7,7a-hexahydropyrrolo[3,4-c]pyridin-5-yl]-7H-pyrrolo[2,3-d]pyrimidine | 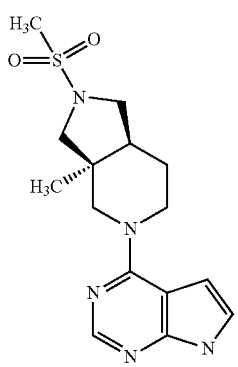 [SMILES: C[C@@]12CN(c3ncnc4[nH]ccc34)CC[C@@H]1CN(S(C)(=O)=O)C2] | 93 | 154 | 243 | 898 |

TABLE 1-continued

JAK kinase inhibitory data
In Table 1 selected JAK kinase inhibitory activities are listed.

| Example # | IUPAC name | Structure | JAK1 EC50 nM | JAK2 EC50 nM | JAK3 EC50 nM | TYK2 EC50 nM |
|---|---|---|---|---|---|---|
| 27 | (3aS*,7aS*)-3a-methyl-5-(7H-pyrrolo[2,3-d]pyrimidin-4-yl)-1,3,4,6,7,7a-hexahydro-pyrrolo[3,4-c]pyridine-2-sulfonamide | 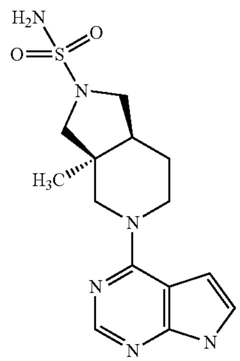 [SMILES: C[C@@]12CN(c3ncnc4[nH]ccc34)CC[C@@H]1CN(S(N)(=O)=O)C2] | 40 | 80 | 54 | 473 |
| 28 | (3aR,7aR)-3a-methyl-5-(7H-pyrrolo[2,3-d]pyrimidin-4-yl)-1,3,4,6,7,7a-hexahydro-pyrrolo[3,4-c]pyridine-2-carbonitrile | 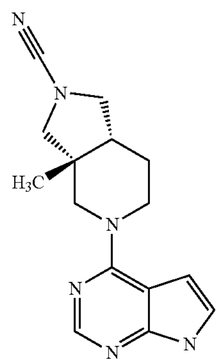 [SMILES: C[C@@]12CN(C#N)C[C@@H]1CCN(c1ncnc3[nH]ccc13)C2] | 240 | 827 | 2180 | 2470 |
| 29 | (3aS,7aS)-3a-methyl-5-(7H-pyrrolo[2,3-d]pyrimidin-4-yl)-1,3,4,6,7,7a-hexahydro-pyrrolo[3,4-c]pyridine-2-carbonitrile | 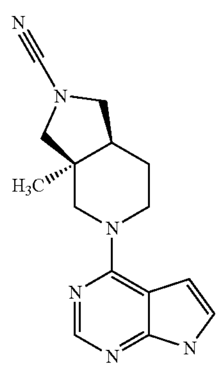 [SMILES: C[C@]12CN(C#N)C[C@H]1CCN(c1ncnc3[nH]ccc13)C2] | 10 | 35 | 118 | 123 |
| 30 | (3aS*,7aS*)-N-(cyanomethyl)-3a-methyl-5-(7H-pyrrolo[2,3-d]pyrimidin-4-yl)-1,3,4,6,7,7a-hexahydro-pyrrolo[3,4-c]pyridine-2-sulfonamide | 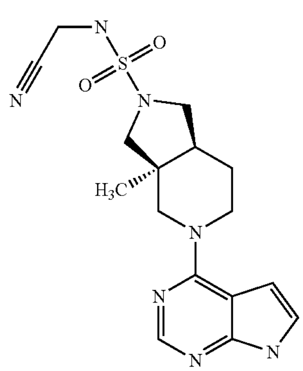 [SMILES: C[C@@]12CN(c3ncnc4[nH]ccc34)CC[C@@H]1CN(S(=O)(=O)NCC#N)C2] | 29 | 56 | 91 | 364 |

TABLE 1-continued

JAK kinase inhibitory data
In Table 1 selected JAK kinase inhibitory activities are listed.

| Example # | IUPAC name | Structure | JAK1 EC50 nM | JAK2 EC50 nM | JAK3 EC50 nM | TYK2 EC50 nM |
|---|---|---|---|---|---|---|
| 31 | 4-[(3aS*,7aS*)-3a-methyl-2-(2,2,2-trifluoroethyl-sulfonyl)-1,3,4,6,7,7a-hexahydro-pyrrolo[3,4-c]pyridin-5-yl]-7H-pyrrolo[2,3-d]pyrimidine | 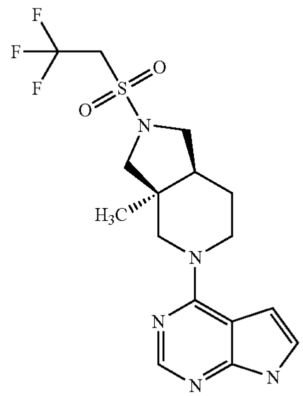 [SMILES: C[C@@]12CN(c3ncnc4[nH]ccc34)CC[C@@H]1CN(S(=O)(=O)CC(F)(F)F)C2] | 133 | 455 | 274 | 3180 |
| 32 | 3-[(3aS*,7aS*)-3a-methyl-5-(7H-pyrrolo[2,3-d]pyrimidin-4-yl)-1,3,4,6,7,7a-hexahydro-pyrrolo[3,4-c]pyridin-2-yl]-3-oxo-propanenitrile | 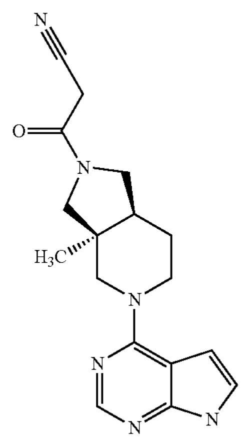 [SMILES: C[C@]12CN(C(=O)CC#N)C[C@H]1CCN(c1ncnc3[nH]ccc13)C2] | 16 | 67 | 162 | 307 |
| 33 | 6-[(3aS,7aS)-3a-methyl-5-(7H-pyrrolo[2,3-d]pyrimidin-4-yl)-1,3,4,6,7,7a-hexahydro-pyrrolo[3,4-c]pyridin-2-yl]pyridine-3-carbonitrile | 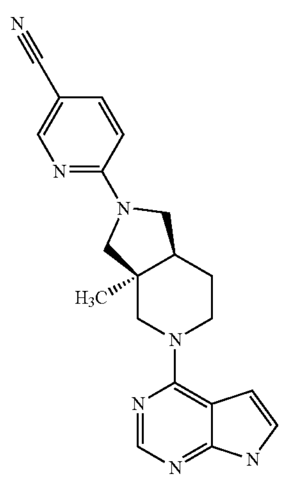 [SMILES: C[C@]12CN(c3ccc(C#N)cn3)C[C@H]1CCN(c1ncnc3[nH]ccc13)C2] | 1 | 5 | 8 | 59 |

TABLE 1-continued

JAK kinase inhibitory data
In Table 1 selected JAK kinase inhibitory activities are listed.

| Example # | IUPAC name | Structure | JAK1 EC50 nM | JAK2 EC50 nM | JAK3 EC50 nM | TYK2 EC50 nM |
|---|---|---|---|---|---|---|
| 34 | 6-[(3aR,7aR)-3a-methyl-5-(7H-pyrrolo[2,3-d]pyrimidin-4-yl)-1,3,4,6,7,7a-hexahydro-pyrrolo[3,4-c]pyridin-2-yl]pyridine-3-carbonitrile | 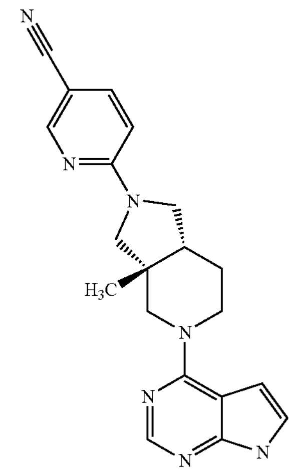 [SMILES: C[C@@]12CN(c3ccc(C#N)cn3)C[C@@H]1CCN(c1ncnc3[nH]ccc13)C2] | 192 | 927 | 1170 | 7010 |
| 35 | 4-[(3aS*,7aS*)-3a-methyl-2-(5-methylsulfonyl-2-pyridyl)-1,3,4,6,7,7a-hexahydro-pyrrolo[3,4-c]pyridin-5-yl]-7H-pyrrolo[2,3-d]pyrimidine | 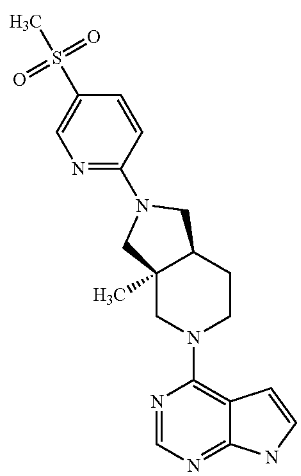 [SMILES: C[C@]12CN(c3ccc(S(C)(=O)=O)cn3)C[C@H]1CCN(c1ncnc3[nH]ccc13)C2] | 13 | 131 | 95 | 2440 |
| 36 | [2-[(3aS*,7aS*)-3a-methyl-5-(7H-pyrrolo[2,3-d]pyrimidin-4-yl)-1,3,4,6,7,7a-hexahydro-pyrrolo[3,4-c]pyridin-2-yl]-3-pyridyl]methanol | 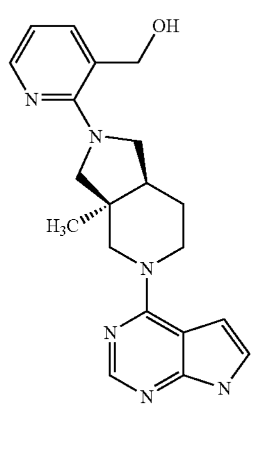 [SMILES: C[C@]12CN(c3ncccc3CO)C[C@H]1CCN(c1ncnc3[nH]ccc13)C2] | 69 | 120 | 235 | 1110 |

TABLE 1-continued

JAK kinase inhibitory data
In Table 1 selected JAK kinase inhibitory activities are listed.

| Example # | IUPAC name | Structure | JAK1 EC50 nM | JAK2 EC50 nM | JAK3 EC50 nM | TYK2 EC50 nM |
|---|---|---|---|---|---|---|
| 37 | [2-[(3aS*,7aS*)-3a-methyl-5-(7H-pyrrolo[2,3-d]pyrimidin-4-yl)-1,3,4,6,7,7a-hexahydro-pyrrolo[3,4-c]pyridin-2-yl]-5-bromo-3-pyridyl]methanol | 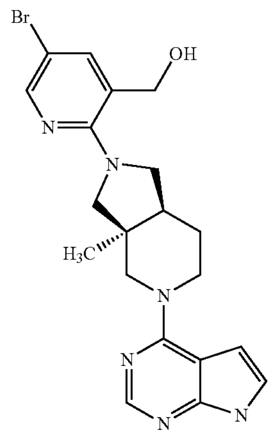 [SMILES: C[C@]12CN(c3ncc(Br)cc3CO)C[C@H]1CCN(c1ncnc3[nH]ccc13)C2] | 12 | 48 | 38 | 611 |
| 38 | 4-[(3aR*,7aS*)-3a-methyl-2-(4-methylsulfonylphenyl)-1,3,4,6,7,7a-hexahydro-pyrrolo[3,4-c]pyridin-5-yl]-7H-pyrrolo[2,3-d]pyrimidine | 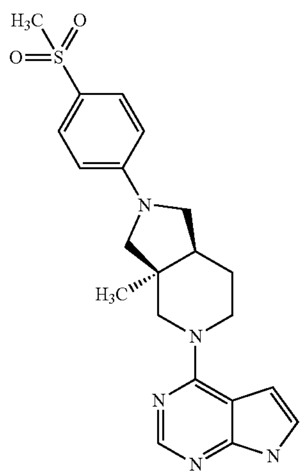 [SMILES: C[C@]12CN(c3ccc(S(C)(=O)=O)cc3)C[C@H]1CCN(c1ncnc3[nH]ccc13)C2] | 7 | 32 | 71 | 335 |
| 39 | 4-[(3aR*,7aS*)-3a-methyl-2-pyrimidin-4-yl-1,3,4,6,7,7a-hexahydro-pyrrolo[3,4-c]pyridin-5-yl]-7H-pyrrolo[2,3-d]pyrimidine | 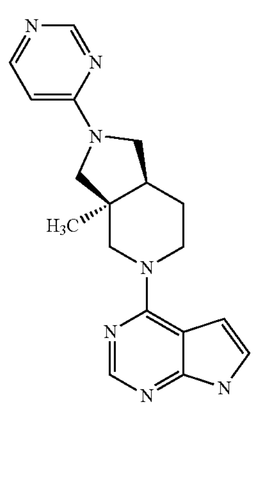 [SMILES: C[C@]12CN(c3ccncn3)C[C@H]1CCN(c1ncnc3[nH]ccc13)C2] | 18 | 72 | 199 | 775 |

TABLE 1-continued

JAK kinase inhibitory data
In Table 1 selected JAK kinase inhibitory activities are listed.

| Example # | IUPAC name | Structure | JAK1 EC50 nM | JAK2 EC50 nM | JAK3 EC50 nM | TYK2 EC50 nM |
|---|---|---|---|---|---|---|
| 40 | 6-[(3aR*,7aS*)-3a-methyl-5-(7H-pyrrolo[2,3-d]pyrimidin-4-yl)-1,3,4,6,7,7a-hexahydro-pyrrolo[3,4-c]pyridin-2-yl]-4-methyl-pyridine-3-carbonitrile | 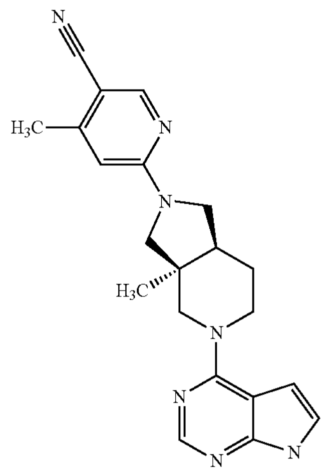 [SMILES: Cc1cc(N2C[C@H]3CCN(c4ncnc5[nH]ccc45)C[C@@]3(C)C2)ncc1C#N] | 3 | 28 | 46 | 722 |
| 41 | 2-[(3aS*,7aS*)-3a-methyl-5-(7H-pyrrolo[2,3-d]pyrimidin-4-yl)-1,3,4,6,7,7a-hexahydro-pyrrolo[3,4-c]pyridin-2-yl]pyrimidine-5-carbonitrile | 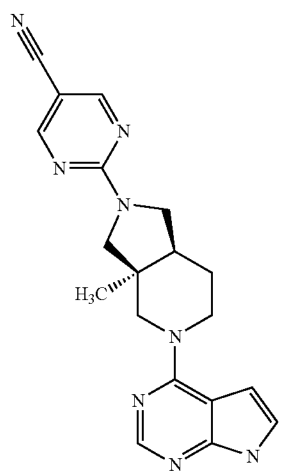 [SMILES: C[C@]12CN(c3ncc(C#N)cn3)C[C@H]1CCN(c1ncnc3[nH]ccc13)C2] | 49 | 216 | 70 | 2040 |
| 42 | 6-[(3aS*,7aS*)-3a-methyl-5-(7H-pyrrolo[2,3-d]pyrimidin-4-yl)-1,3,4,6,7,7a-hexahydro-pyrrolo[3,4-c]pyridin-2-yl]pyridazine-3-carbonitrile | 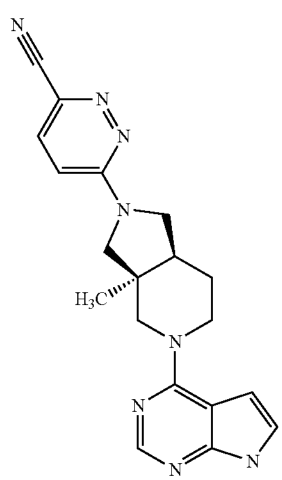 [SMILES: C[C@]12CN(c3ccc(C#N)nn3)C[C@H]1CCN(c1ncnc3[nH]ccc13)C2] | 10 | 53 | 78 | 574 |

TABLE 1-continued

JAK kinase inhibitory data
In Table 1 selected JAK kinase inhibitory activities are listed.

| Example # | IUPAC name | Structure | JAK1 EC50 nM | JAK2 EC50 nM | JAK3 EC50 nM | TYK2 EC50 nM |
|---|---|---|---|---|---|---|
| 43 | 5-[(3aS*,7aS*)-3a-methyl-5-(7H-pyrrolo[2,3-d]pyrimidin-4-yl)-1,3,4,6,7,7a-hexahydro-pyrrolo[3,4-c]pyridin-2-yl]pyrazine-2-carbonitrile | 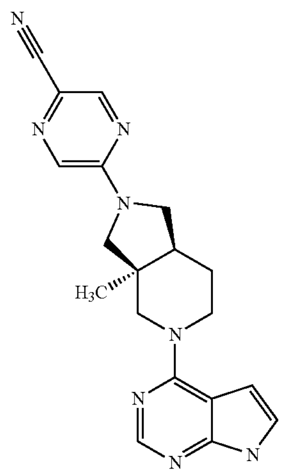 [SMILES: C[C@]12CN(c3cnc(C#N)cn3)C[C@H]1CCN(c1ncnc3[nH]ccc13)C2] | 3 | 22 | 37 | 232 |
| 44 | 6-[(3aS*,7aS*)-3a-methyl-5-(7H-pyrrolo[2,3-d]pyrimidin-4-yl)-1,3,4,6,7,7a-hexahydro-pyrrolo[3,4-c]pyridin-2-yl]-5-methyl-pyridine-3-carbonitrile | 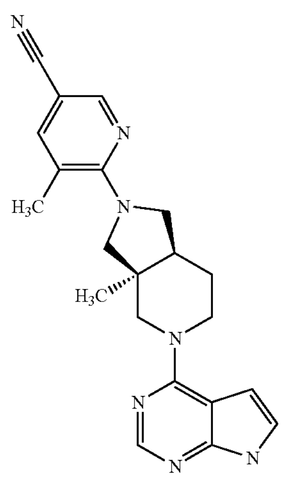 [SMILES: Cc1cc(C#N)cnc1N1C[C@H]2CCN(c3ncnc4[nH]ccc34)C[C@@]2(C)C1] | 65 | 179 | 99 | 2020 |
| 45 | 6-[(3aR*,7aS*)-3a-methyl-5-(7H-pyrrolo[2,3-d]pyrimidin-4-yl)-1,3,4,6,7,7a-hexahydro-pyrrolo[3,4-c]pyridin-2-yl]-2-methyl-pyridine-3-carbonitrile | 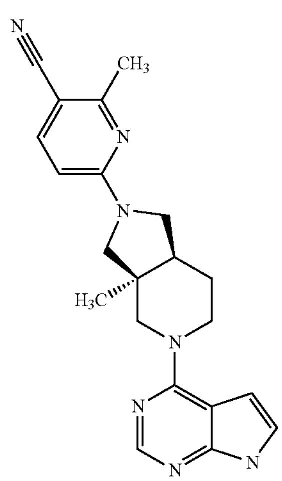 [SMILES: Cc1nc(N2C[C@H]3CCN(c4ncnc5[nH]ccc45)C[C@@]3(C)C2)ccc1C#N] | 30 | 103 | 120 | 1190 |

TABLE 1-continued

JAK kinase inhibitory data
In Table 1 selected JAK kinase inhibitory activities are listed.

| Example # | IUPAC name | Structure | JAK1 EC50 nM | JAK2 EC50 nM | JAK3 EC50 nM | TYK2 EC50 nM |
|---|---|---|---|---|---|---|
| 46 | 1-[(3aS*,7aS*)-3a-methyl-5-(7H-pyrrolo[2,3-d]pyrimidin-4-yl)-1,3,4,6,7,7a-hexahydropyrrolo[3,4-c]pyridine-2-carbonyl]cyclopentanecarbonitrile | 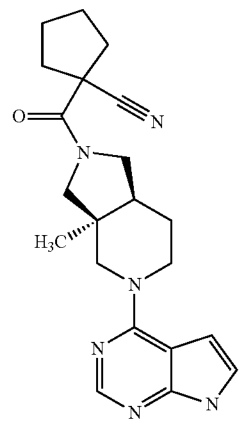 [SMILES: C[C@]12CN(C(=O)C3(C#N)CCCC3)C[C@H]1CCN(c1ncnc3[nH]ccc13)C2] | 97 | 625 | 705 | 1510 |
| 47 | 6-[(3aS*,7aS*)-3a-methyl-5-(7H-pyrrolo[2,3-d]pyrimidin-4-yl)-1,3,4,6,7,7a-hexahydropyrrolo[3,4-c]pyridin-2-yl]pyridine-3-carbonitrile | 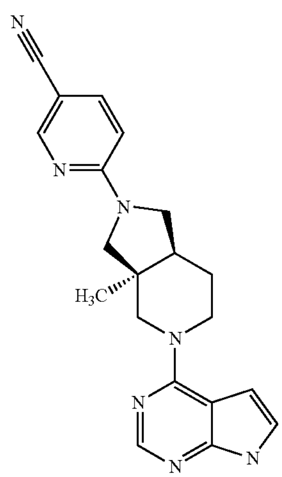 [SMILES: C[C@]12CN(c3ccc(C#N)cn3)C[C@H]1CCN(c1ncnc3[nH]ccc13)C2] | 5 | 30 | 26 | 159 |

To assess the in vitro metabolic stability, the compounds (0.5 µM) were incubated in duplicates with human liver microsomes (0.5 mg/mL) in phosphate buffer and NADPH, in 96-well plates for 40 min (37° C.), using a liquid handling robot (Hamilton Microlab Star). Sample aliquots were taken at 0, 5, 10, 20 and 40 min, and dispensed into cold acetonitrile, in order to stop the reactions. The plates were centrifuged for 30 minutes before the samples were analyzed using liquid chromatography coupled to a time-of-flight mass spectrometer (AB Sciex API5600). The compound depletion over time was used to estimate the elimination rate constant, from which the apparent intrinsic clearance, Clapp, was calculated and the values are listed in table 2.

TABLE 2

Human liver microsome $Cl_{app}$ data

| Example # | $Cl_{app}$ mL/min/kg |
|---|---|
| 1 | 54 |
| 2 | 62 |
| 3 | 60 |
| 8 | 200 |
| 16 | 116 |
| 17 | 197 |
| 18 | 127 |
| 20 | 200 |
| 22 | 185 |
| 23 | 200 |
| 29 | 10 |
| 33 | 166 |
| 34 | 136 |
| 40 | 200 |
| 42 | 53 |
| 43 | 55 |
| 47 | 133 |

The invention claimed is:
1. A compound according to general formula I

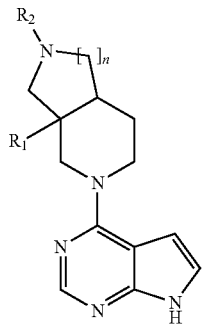

wherein
R₁ is methyl or ethyl;
n is 1 or 2;
R₂ is selected from the group consisting of hydrogen, cyano, —SO₂R$_a$, —SO₂NR$_b$R$_c$, —C(O)R$_b$, phenyl, and 5- and 6-membered heteroaryl, wherein said phenyl, 5- and 6-membered heteroaryl are optionally substituted with one or more substituents independently selected from R₃,
R₃ is selected from the group consisting of hydroxyl, cyano, halogen, (C₁-C₄)alkyl, hydroxyl(C₁-C₄)alkyl, halo(C₁-C₄)alkyl, cyano(C₁-C₄)alkyl, (C₁-C₄)alkoxy, halo(C₁-C₄)alkoxy, —SO₂R$_a$, and —SO₂NR$_b$R$_c$;
R$_a$ is selected from the group consisting of (C₁-C₄)alkyl, (C₃-C₆)cycloalkyl, halo(C₁-C₄)alkyl, and cyano(C₁-C₄)alkyl;
R$_b$ and R$_c$ are each independently selected from the group consisting of hydrogen, (C₁-C₄)alkyl, halo(C₁-C₄)alkyl, cyano(C₁-C₄)alkyl, (C₃-C₆)cycloalkyl, halo(C₃-C₆)cycloalkyl, and cyano(C₃-C₆)cycloalkyl;
or a pharmaceutically acceptable salt, hydrate, or solvate thereof.

2. The compound according to claim 1 of general formula I(a),

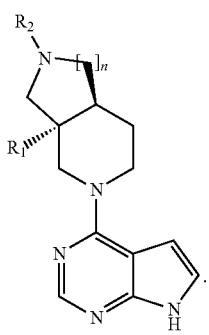

3. The compound according to claim 1, wherein R₁ is ethyl and n is 2.
4. The compound according to claim 1, wherein R₂ is selected from the group consisting of hydrogen, cyano, —SO₂R$_a$, —SO₂NR$_b$R$_c$, —C(O)R$_b$, phenyl, pyridyl, pyrimidinyl, pyrazinyl, pyridazinyl, thiazolyl, and thiadiazolyl, wherein said phenyl, pyridyl, pyrimidinyl, pyrazinyl, pyridazinyl, thiazolyl, and thiadiazolyl are optionally substituted with one or more substituents independently selected from R₃.

5. The compound according to claim 1, wherein R₂ is selected from the group consisting of cyano and —SO₂NH₂.
6. The compound according to claim 1, wherein R₃ is selected from the group consisting of cyano, halogen, methyl, hydroxymethyl, and —SO₂CH₃.
7. The compound according to claim 1, wherein R$_a$ is selected from methyl and trifluoroethyl.
8. The compound according to claim 1, wherein R$_b$ and R$_c$ each independently are selected from hydrogen, methyl, and cyanomethyl.
9. A compound according to claim 1 selected from the group consisting of:
(i) (4aR,8aS)-8a-methyl-7-(7H-pyrrolo[2,3-d]pyrimidin-4-yl)-3,4,4a,5,6,8-hexahydro-1H-2,7-naphthyridine-2-carbonitrile,
(ii) (4aR*,8aS*)-8a-methyl-7-(7H-pyrrolo[2,3-d]pyrimidin-4-yl)-3,4,4a,5,6,8-hexahydro-1H-2,7-naphthyridine-2-carbonitrile,
(iii) (4aS,8aR)-8a-methyl-7-(7H-pyrrolo[2,3-d]pyrimidin-4-yl)-3,4,4a,5,6,8-hexahydro-1H-2,7-naphthyridine-2-carbonitrile,
(iv) 5-[(4aR*,8aS*)-8a-methyl-7-(7H-pyrrolo[2,3-d]pyrimidin-4-yl)-3,4,4a,5,6,8-hexahydro-1H-2,7-naphthyridin-2-yl]pyrazine-2-carbonitrile,
(v) 6-[(4aR*,8aS*)-8a-methyl-7-(7H-pyrrolo[2,3-d]pyrimidin-4-yl)-3,4,4a,5,6,8-hexahydro-1H-2,7-naphthyridin-2-yl]pyridine-3-carbonitrile,
(vi) 6-[(4aR*,8aS*)-8a-methyl-7-(7H-pyrrolo[2,3-d]pyrimidin-4-yl)-3,4,4a,5,6,8-hexahydro-1H-2,7-naphthyridin-2-yl]pyridazine-3-carbonitrile,
(vii) 2-[(4aR*,8aS*)-8a-methyl-7-(7H-pyrrolo[2,3-d]pyrimidin-4-yl)-3,4,4a,5,6,8-hexahydro-1H-2,7-naphthyridin-2-yl]pyrimidine-5-carbonitrile,
(viii) 6-[(4aS*,8aR*)-8a-methyl-7-(7H-pyrrolo[2,3-d]pyrimidin-4-yl)-3,4,4a,5,6,8-hexahydro-1H-2,7-naphthyridin-2-yl]-4-methyl-pyridine-3-carbonitrile,
(ix) (4aR*,8aS*)-8a-methyl-7-(7H-pyrrolo[2,3-d]pyrimidin-4-yl)-3,4,4a,5,6,8-hexahydro-1H-2,7-naphthyridine-2-sulfonamide,
(x) 6-[(4aS*,8aR*)-8a-methyl-7-(7H-pyrrolo[2,3-d]pyrimidin-4-yl)-3,4,4a,5,6,8-hexahydro-1H-2,7-naphthyridin-2-yl]-2-methyl-pyridine-3-carbonitrile,
(xi) 6-[(4aS*,8aR*)-8a-methyl-7-(7H-pyrrolo[2,3-d]pyrimidin-4-yl)-3,4,4a,5,6,8-hexahydro-1H-2,7-naphthyridin-2-yl]-5-methyl-pyridine-3-carbonitrile,
(xii) (4aS*,8aR*)-2-(5-bromo-4-methyl-2-pyridyl)-8a-methyl-7-(7H-pyrrolo[2,3-d]pyrimidin-4-yl)-3,4,4a,5,6,8-hexahydro-1H-2,7-naphthyridine,
(xiii) (4aR*,8aS*)-8a-methyl-2-methylsulfonyl-7-(7H-pyrrolo[2,3-d]pyrimidin-4-yl)-3,4,4a,5,6,8-hexahydro-1H-2,7-naphthyridine,
(xiv) (4aS*,8aR*)-2-(5-bromo-6-methyl-2-pyridyl)-8a-methyl-7-(7H-pyrrolo[2,3-d]pyrimidin-4-yl)-3,4,4a,5,6,8-hexahydro-1H-2,7-naphthyridine,
(xv) 1-[(4aR*,8aS*)-8a-ethyl-7-(7H-pyrrolo[2,3-d]pyrimidin-4-yl)-3,4,4a,5,6,8-hexahydro-1H-2,7-naphthyridin-2-yl]ethanone,
(xvi) (4aR*,8aS*)-8a-ethyl-7-(7H-pyrrolo[2,3-d]pyrimidin-4-yl)-3,4,4a,5,6,8-hexahydro-1H-2,7-naphthyridine-2-carbaldehyde,
(xvii) (4aR*,8aS*)-8a-ethyl-7-(7H-pyrrolo[2,3-d]pyrimidin-4-yl)-3,4,4a,5,6,8-hexahydro-1H-2,7-naphthyridine-2-sulfonamide, (xviii) (4aR,8aS)-8a-ethyl-7-(7H-pyrrolo[2,3-d]pyrimidin-4-yl)-3,4,4a,5,6,8-hexahydro-1H-2,7-naphthyridine-2-sulfonamide,
(xix) (4aS,8aR)-8a-ethyl-7-(7H-pyrrolo[2,3-d]pyrimidin-4-yl)-3,4,4a,5,6,8-hexahydro-1H-2,7-naphthyridine-2-sulfonamide,
(xx) 2-[(4aR*,8aS*)-8a-ethyl-7-(7H-pyrrolo[2,3-d]pyrimidin-4-yl)-3,4,4a,5,6,8-hexahydro-1H-2,7-naphthyridin-2-yl]-5-bromo-1,3,4-thiadiazole,
(xxi) (4aS,8aR)-8a-ethyl-7-(7H-pyrrolo[2,3-d]pyrimidin-4-yl)-3,4,4a,5,6,8-hexahydro-1H-2,7-naphthyridine-2-carbonitrile,
(xxii) (4aR,8aS)-8a-ethyl-7-(7H-pyrrolo[2,3-d]pyrimidin-4-yl)-3,4,4a,5,6,8-hexahydro-1H-2,7-naphthyridine-2-carbonitrile,
(xxiii) (4aR*,8aS*)-8a-ethyl-7-(7H-pyrrolo[2,3-d]pyrimidin-4-yl)-3,4,4a,5,6,8-hexahydro-1H-2,7-naphthyridine-2-carbonitrile,
(xxiv) 8a-ethyl-7-(7H-pyrrolo[2,3-d]pyrimidin-4-yl)-1,2,3,4,4a,5,6,8-octahydro-2,7-naphthyridine,
(xxv) 2 [(4aR*,8aS*)-8a-ethyl-7-(7H-pyrrolo[2,3-d]pyrimidin-4-yl)-3,4,4a,5,6,8-hexahydro-1H-2,7-naphthyridin-2-yl]thiazole-4-carbonitrile,
(xxiv) 4-[(3aS*,7aS*)-3a-methyl-2-m ethylsulfonyl-1,3,4,6,7,7a-hexahydropyrrolo[3,4-c]pyridin-5-yl]-7H-pyrrolo[2,3-d]pyrimidine,
(xxvii) (3aS*,7aS*)-3a-methyl-5-(7H-pyrrolo[2,3-d]pyrimidin-4-yl)-1,3,4,6,7,7a-hexahydropyrrolo[3,4-c]pyridine-2-sulfonamide,
(xxviii) (3aR,7aR)-3a-methyl-5-(7H-pyrrolo[2,3-d]pyrimidin-4-yl)-1,3,4,6,7,7a-hexahydropyrrolo[3,4-c]pyridine-2-carbonitrile,
(xxix) (3aS,7aS)-3a-methyl-5-(7H-pyrrolo[2,3-d]pyrimidin-4-yl)-1,3,4,6,7,7a-hexahydropyrrolo[3,4-c]pyridine-2-carbonitrile,
(xxx) (3aS*,7aS*)-N-(cyanomethyl)-3a-methyl-5-(7H-pyrrolo[2,3-d]pyrimidin-4-yl)-1,3,4,6,7,7a-hexahydropyrrolo[3,4-c]pyridine-2-sulfonamide,
(xxxi) 4-[(3aS*,7aS*)-3a-methyl-2-(2,2,2-trifluoroethylsulfonyl)-1,3,4,6,7,7a-hexahydropyrrolo[3,4-c]pyridin-5-yl]-7H-pyrrolo[2,3-d]pyrimidine,
(xxxii) 3-[(3aS*,7aS*)-3a-methyl-5-(7H-pyrrolo[2,3-d]pyrimidin-4-yl)-1,3,4,6,7,7a-hexahydropyrrolo[3,4-c]pyridin-2-yl]-3-oxo-propanenitrile,
(xxxiii) 6-[(3aS,7aS)-3a-methyl-5-(7H-pyrrolo[2,3-d]pyrimidin-4-yl)-1,3,4,6,7,7a-hexahydropyrrolo[3,4-c]pyridin-2-yl]pyridine-3-carbonitrile,
(xxxiv) 6-[(3aR,7aR)-3a-methyl-5-(7H-pyrrolo[2,3-d]pyrimidin-4-yl)-1,3,4,6,7,7a-hexahydropyrrolo[3,4-c]pyridin-2-yl]pyridine-3-carbonitrile,
(xxxv) 4-[(3aS*,7aS*)-3a-methyl-2-(5-methylsulfonyl-2-pyridyl)-1,3,4,6,7,7a-hexahydropyrrolo[3,4-c]pyridin-5-yl]-7H-pyrrolo[2,3-d]pyrimidine,
(xxxvi) [2-[(3aS*,7aS*)-3a-methyl-5-(7H-pyrrolo[2,3-d]pyrimidin-4-yl)-1,3,4,6,7,7a-hexahydropyrrolo[3,4-c]pyridin-2-yl]-3-pyridyl]methanol,
(xxxvii) [2-[(3aS*,7aS*)-3a-methyl-5-(7H-pyrrolo[2,3-d]pyrimidin-4-yl)-1,3,4,6,7,7a-hexahydropyrrolo[3,4-c]pyridin-2-yl]-5-bromo-3-pyridyl]methanol,
(xxxviii) 4-[(3aR*,7aS*)-3a-methyl-2-(4-methylsulfonylphenyl)-1,3,4,6,7,7a-hexahydropyrrolo[3,4-c]pyridin-5-yl]-7H-pyrrolo[2,3-d]pyrimidine,
(xxxix) 4-[(3aR*,7aS*)-3a-methyl-2-pyrimidin-4-yl-1,3,4,6,7,7a-hexahydropyrrolo[3,4-c]pyridin-5-yl]-7H-pyrrolo[2,3-d]pyrimidine, (xl) 6-[(3aR*,7aS*)-3a-methyl-5-(7H-pyrrolo[2,3-d]pyrimidin-4-yl)-1,3,4,6,7,7a-hexahydropyrrolo[3,4-c]pyridin-2-yl]-4-methyl-pyridine-3-carbonitrile,
(xli) 2-[(3aS*,7aS*)-3a-methyl-5-(7H-pyrrolo[2,3-d]pyrimidin-4-yl)-1,3,4,6,7,7a-hexahydropyrrolo[3,4-c]pyridin-2-yl]pyrimidine-5-carbonitrile,
(xlii) 6-[(3aS*,7aS*)-3a-methyl-5-(7H-pyrrolo[2,3-d]pyrimidin-4-yl)-1,3,4,6,7,7a-hexahydropyrrolo[3,4-c]pyridin-2-yl]pyridazine-3-carbonitrile,
(xliii) 5-[(3aS*,7aS*)-3a-methyl-5-(7H-pyrrolo[2,3-d]pyrimidin-4-yl)-1,3,4,6,7,7a-hexahydropyrrolo[3,4-c]pyridin-2-yl]pyrazine-2-carbonitrile,
(xliv) 6-[(3aS*,7aS*)-3a-methyl-5-(7H-pyrrolo[2,3-d]pyrimidin-4-yl)-1,3,4,6,7,7a-hexahydropyrrolo[3,4-c]pyridin-2-yl]-5-methyl-pyridine-3-carbonitrile,
(xlv) 6-[(3aR*,7aS*)-3a-methyl-5-(7H-pyrrolo[2,3-d]pyrimidin-4-yl)-1,3,4,6,7,7a-hexahydropyrrolo[3,4-c]pyridin-2-yl]-2-methyl-pyridine-3-carbonitrile,
(xlvi) 1-[(3aS*,7aS*)-3a-methyl-5-(7H-pyrrolo[2,3-d]pyrimidin-4-yl)-1,3,4,6,7,7a-hexahydropyrrolo[3,4-c]pyridine-2-carbonyl]cyclopentanecarbonitrile, and
(xlvii) 6-[(3aS*,7aS*)-3a-methyl-5-(7H-pyrrolo[2,3-d]pyrimidin-4-yl)-1,3,4,6,7,7a-hexahydropyrrolo[3,4-c]pyridin-2-yl]pyridine-3-carbonitrile,
or a pharmaceutically acceptable salt, hydrate, or solvate thereof.

10. The compound according to claim 1, wherein the compound is (4aR,8aS)-8a-ethyl-7-(7H-pyrrolo[2,3-d]pyrimidin-4-yl)-3,4,4a,5,6,8-hexahydro-1H-2,7-naphthyridine-2-sulfonamide or a pharmaceutically acceptable salt, hydrate, or solvate thereof.

11. The compound according to claim 1, wherein the compound is (4aR,8aS)-8a-ethyl-7-(7H-pyrrolo[2,3-d]pyrimidin-4-yl)-3,4,4a,5,6,8-hexahydro-1H-2,7-naphthyridine-2-carbonitrile or a pharmaceutically acceptable salt, hydrate, or solvate thereof.

12. A pharmaceutical composition comprising a compound according to claim 1 and one or more pharmaceutically acceptable vehicles, excipients, and/or pharmaceutically acceptable carriers.

13. The pharmaceutical composition according to claim 12, further comprising one or more other therapeutically active compounds.

14. A method of treatment of one or more proliferative or inflammatory skin disorders, comprising administering to a person suffering from at least one of said skin diseases an effective amount of one or more compounds according to according to claim 1.

15. The method of claim 14, wherein the proliferative or inflammatory skin disorder is psoriasis, atopic dermatitis, scleroderma, rosacea, skin cancer, dermatitis, dermatitis herpetiformis, dermatomyositis, vitiligo, alopecia areata, contact dermatitis, eczema, xerosis, urticaria, or chronic idiopathic pruritus.

16. The method of claim 14, wherein the proliferative or inflammatory skin disorder is psoriasis or atopic dermatitis.

17. The method of claim 14, wherein the proliferative or inflammatory skin disorders is responsive to the inhibition of protein tyrosine kinases of the JAK family of protein tyrosine kinases or TYK2 protein tyrosine kinases.

18. The method of claim 17, wherein the protein tyrosine kinases of the JAK family of protein tyrosine kinases are JAK1, JAK2, and/or JAK3.

19. A method of treatment of one or more proliferative or inflammatory skin disorders, comprising administering to a person suffering from at least one of said skin diseases an effective amount of the pharmaceutical composition according to claim 12.

20. The method of claim 19, wherein the proliferative or inflammatory skin disease is psoriasis, atopic dermatitis, scleroderma, rosacea, skin cancer, dermatitis, dermatitis herpetiformis, dermatomyositis, vitiligo, alopecia areata, contact dermatitis, eczema, xerosis, urticaria, or chronic idiopathic pruritus.

* * * * *

UNITED STATES PATENT AND TRADEMARK OFFICE
CERTIFICATE OF CORRECTION

| | | |
|---|---|---|
| PATENT NO. | : 10,851,116 B2 | Page 1 of 1 |
| APPLICATION NO. | : 16/479375 | |
| DATED | : December 1, 2020 | |
| INVENTOR(S) | : Daniel Greve | |

It is certified that error appears in the above-identified patent and that said Letters Patent is hereby corrected as shown below:

On the Title Page

Item (30), under "Foreign Application Priority Data," "17152447" should read --17152447.3--.

In the Claims

Claim 9, Column 113, Line 25, "(xxiv)" should read --(xxvi)--.

Claim 9, Column 113, Line 25, "m ethylsulfonyl" should read --methylsulfonyl--.

Signed and Sealed this
Twenty-fourth Day of January, 2023

Katherine Kelly Vidal
*Director of the United States Patent and Trademark Office*